(12) United States Patent
Nguyen

(10) Patent No.: US 9,295,731 B2
(45) Date of Patent: Mar. 29, 2016

(54) CLEAVABLE DRUG CONJUGATES, COMPOSITIONS THEREOF AND METHODS OF USE

(71) Applicant: Mark Quang Nguyen, San Jose, CA (US)

(72) Inventor: Mark Quang Nguyen, San Jose, CA (US)

(73) Assignee: Mark Quang Nguyen, San Jose, CA (US)

( * ) Notice: Subject to any disclaimer, the term of this patent is extended or adjusted under 35 U.S.C. 154(b) by 0 days.

(21) Appl. No.: 13/854,296

(22) Filed: Apr. 1, 2013

(65) Prior Publication Data

US 2014/0294851 A1 Oct. 2, 2014

(51) Int. Cl.
*A61K 47/48* (2006.01)
*A61K 45/06* (2006.01)

(52) U.S. Cl.
CPC ........... *A61K 47/48284* (2013.01); *A61K 45/06* (2013.01); *A61K 47/4843* (2013.01); *A61K 47/48061* (2013.01); *A61K 47/48092* (2013.01); *A61K 47/48246* (2013.01)

(58) Field of Classification Search
None
See application file for complete search history.

(56) References Cited

U.S. PATENT DOCUMENTS

2003/0022876 A1 * 1/2003 Ashton et al. ................. 514/176

\* cited by examiner

*Primary Examiner* — Alicia L Otton

(57) ABSTRACT

Base-labile crosslinkers, base-labile conjugates comprising such crosslinkers, methods of their synthesis and use are disclosed.

10 Claims, No Drawings

CLEAVABLE DRUG CONJUGATES, COMPOSITIONS THEREOF AND METHODS OF USE

FIELD

The disclosure relates to multi-functional crosslinkers capable of coupling primary or secondary amine-containing therapeutic agents to ligands. The multi-functional crosslinkers are cleavable upon exposure to esterases or to basic conditions to release the amine-containing therapeutic agents. The disclosure also relates to conjugates comprising the crosslinkers, a therapeutic agent, and a ligand.

BACKGROUND

Drugs can often cause severe side effects and/or require multiple dosing regimens. Some of these side effects and inconvenient dosing regimens can be controlled or reduced by the use of improved formulations and/or improved delivery methods.

Paclitaxel, for example, is highly effective in treating breast and lung cancers by inhibiting the growth of cancer cells by binding to microtubules. However, because the drug has a low aqueous solubility, paclitaxel is typically formulated using the toxic solvent Cremophor® EL (polyoxyethylated castor oil), which limits the amount of drug that can be administered to a patient. Patients taking the drug often require premedication with steroids or antihistamines for hypersensitivity reactions caused by the solvent.

Abraxane®, a new paclitaxel formulation, does not employ a toxic solvent. When formulated with human serum albumin, the drug can be suspended in aqueous media. Thus, patients can better tolerate higher paclitaxel doses (up to 260 mg/m$^2$ vs. 175 g/m$^2$) and thereby achieve an improved response rate.

Doxorubicin is another highly effective cancer drug belonging to a class of anthracycline compounds. However, the drug can cause severe cardiotoxicity and death. Patients taking a cumulative dose of 300 mg/m$^2$ have a 1-2% chance of developing cardiomyopathy, with the incidence increasing with increasing dose (400 mg/m$^2$, 3-5%; 450 mg/m$^2$, 5 to 8%; 500 mg/m$^2$, 6-20%). The use of Doxil®, a pegylated liposomal formulation of doxorubicin, results in a reduced incidence of cardiotoxicity. Doxil® has a half-life in the blood of about 50 hours compared to about 10 minutes for doxorubicin. The slow-release of doxorubicin may explain the lower toxicity of the Doxil® formulation. Myocet®, a non-pegylated liposomal formulation of doxorubicin, also reduces the incidence of cardiotoxicity. Furthermore, its use also reduces the incidence of hand-foot syndrome associated with Doxil®. Myocet® is approved in Europe and is being evaluated in the United States.

Mitoxantrone is used for the treatment of acute non-lymphocytic leukemia. It is also indicated for reducing neurologic disability and/or the frequency of clinical relapses in patients with secondary (chronic) progressive, progressive relapsing, or worsening relapsing-remitting multiple sclerosis (MS). Although one of the most effective drugs for treating MS, mitoxantrone is not recommended for long-term use. Patients who exceed a cumulative dose of 140 mg/m$^2$ have an increased risk of acquiring irreversible cardiotoxicity and death. There is no liposomal formulation of this drug.

Bleomycin, in combination with other chemotherapeutic agents, is effective in treating squamous cell carcinoma, non-Hodgkin's lymphoma, and testicular carcinoma. However, patients taking a cumulative dose of 400 units (~400 mg) risk developing pulmonary fibrosis.

Mertansine, a derivative of maytansine, is an experimental cytotoxic agent. Because of its extreme toxicity, it is not used as a stand-alone therapeutic agent. To minimize side effects and to maximize efficacy, the compound is conjugated to tumor-targeting monoclonal antibodies such as lorvotuzumab and trastuzumab.

Vedotin, an auristatin, is another potent cytotoxic agent. To minimize side effects and to maximize efficacy, it is conjugated to tumor-targeting monoclonal antibody brentuximab.

Recombinant interferon alfa-2a (Roferon® A) is used for the treatment of chronic hepatitis C, hairy cell leukemia, and chronic myelogenous leukemia. The recommended dosing regimen for Roferon® A for the treatment of chronic hepatitis C is three times per week administered subcutaneously for 12 months.

Pegasys®, a pegylated formulation of interferon alfa-2a, requires less frequent dosing. The recommended dosing regimen for Pegasys® for treating chronic hepatitis C is once weekly for 48 weeks by subcutaneous administration.

Zalbin®, an interferon alfa-2b conjugated to human serum albumin, is an alternative to unconjugated interferon alfa-2b (Intron® A). Instead of subcutaneously or intramuscularly dosing the non-conjugated drug three times a week for up to 24 months, Zalbin® is administered only once every two weeks.

Enfuvirtide, an FDA-approved HIV drug, is a fusion inhibitor having a linear 36-amino acid synthetic peptide. Due to its short half-life of four hours, treatment requires twice-daily subcutaneous injections. This inconvenient dosing schedule discourages its widespread use.

SUMMARY

Thus, there is a need for improved drug formulations that can reduce or eliminate severe side effects and enhance the tolerability, efficacy, and/or compliance of the drug. More specifically, many pharmacological compounds having amine groups can benefit from conjugation to other molecules or moieties provided that the crosslinking group is cleavable in vivo to release the drug. Thus, there is a need for new crosslinkers having a functional group that can form a cleavable bond with amine-containing molecules upon exposure to esterases and/or under mild basic conditions (e.g., pH 7.4 to 9) in vivo.

Cleavable cross-linkers, intermediates of cleavable cross-linkers, cleavable conjugates comprising the cleavable cross-linkers, and methods of synthesizing the cross-linkers, intermediates, and conjugates are disclosed. Therapeutic conjugates provided by the present disclosure comprising the cleavable cross-linkers can reduce the side effects, enhance the efficacy, and/or improve the convenience of treatment for the parent drug.

In a first aspect, compounds of Formula (II) are disclosed:

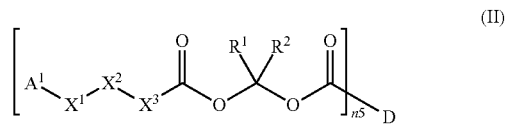

or a salt thereof, wherein:
each $A^1$ is independently selected from a thiol-reactive group, an amine-reactive group, an avidin-binding group, a photoreactive group, an alkyne-reactive group, and an azide-reactive group;

each $X^1$ and $X^3$ is independently selected from a covalent bond, $C_{1-20}$ alkanediyl, substituted $C_{1-20}$ alkanediyl, $C_{1-20}$ heteroalkanediyl, substituted $C_{1-20}$ heteroalkanediyl, $C_{3-12}$ cycloalkanediyl, substituted $C_{3-12}$ cycloalkanediyl, $C_{3-12}$ heterocycloalkanediyl, substituted $C_{3-12}$ heterocycloalkanediyl, $C_{4-20}$ alkanecycloalkanediyl, substituted $C_{4-20}$ alkanecycloalkanediyl, $C_{4-20}$ heteroalkanecycloalkanediyl, substituted $C_{4-20}$ heteroalkanecycloalkanediyl, $C_{6-20}$ arenediyl, substituted $C_{6-20}$ arenediyl, $C_{6-20}$ heteroarenediyl, substituted $C_{6-20}$ heteroarenediyl, $C_{7-20}$ alkanearenediyl, substituted $C_{7-20}$ alkanearenediyl, $C_{6-20}$ heteroalkanearenediyl, substituted $C_{6-20}$ heteroalkanearenediyl, and —$(CH_2)_{n1}$—$(CH_2$—$CH_2$—$O)_{n2}$—$(CH_2)_{n3}$—, wherein:
each n1 and n3 is independently an integer selected from 0 to 5; and
each n2 is independently an integer selected from 1 to 25;

each $X^2$ is independently selected from a covalent bond, —O—, —S—, —N—, —N=, —N=N—, —N=C—, —SO—, —SO$_2$—, —SO$_2$N—, —SS—, —C(O)—, —C(O)O—, —C(O)N—, —C(O)S—, —C(O)N—N=, —OP(O)(OH)O—, —OC(O)O—, —OC(O)N—, —NC(O)N—, and —NC(S)N;

each $R^1$ and $R^2$ is independently selected from hydrogen, $C_{1-6}$ alkyl, substituted $C_{1-6}$ alkyl, $C_{1-6}$ heteroalkyl, substituted $C_{1-6}$ heteroalkyl, $C_{6-10}$ aryl, substituted $C_{6-10}$ aryl, $C_{6-10}$ heteroaryl, and substituted $C_{6-10}$ heteroaryl;

D is selected from a therapeutic agent having at least one primary amine group, a therapeutic agent having at least one secondary amine group, a therapeutic agent having at least one hydroxy group, and a therapeutic agent having at least one thiol group; and n5 is an integer selected from 1 to 20.

In a second aspect, compounds of Formula (III) are disclosed:

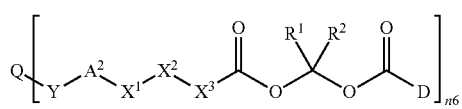

(III)

or a pharmaceutically acceptable salt thereof, wherein:
Q is selected from a ligand having at least one thiol group, a ligand having at least one primary amine group, a ligand having at least one secondary amine group, ligand having at least one biotin-binding group, a ligand having at least one photoreactive group, a ligand having at least one alkyne group, and a ligand having at least one azide group;

each Y is independently selected from a covalent bond and a hydrogen bond;

each $A^2$ is independently selected from a covalent bond, an amide group, an avidin-binding group, a carbamate group, a carbonyl group, a disulfide group, an ester group, a hydrazone group, an imine group, a succinimide group, a sulfonamide group, a sulfone group, a sulfoxide group, a thioether group, a triazole group, and a urea group;

each $X^1$ and $X^3$ is independently selected from a covalent bond, $C_{1-20}$ alkanediyl, substituted $C_{1-20}$ alkanediyl, $C_{1-20}$ heteroalkanediyl, substituted $C_{1-20}$ heteroalkanediyl, $C_{3-12}$ cycloalkanediyl, substituted $C_{3-12}$ cycloalkanediyl, $C_{3-12}$ heterocycloalkanediyl, substituted $C_{3-12}$ heterocycloalkanediyl, $C_{4-20}$ alkanecycloalkanediyl, substituted $C_{4-20}$ alkanecycloalkanediyl, $C_{4-20}$ heteroalkanecycloalkanediyl, substituted $C_{4-20}$ heteroalkanecycloalkanediyl, $C_{6-20}$ arenediyl, substituted $C_{6-20}$ arenediyl, $C_{6-20}$ heteroarenediyl, substituted $C_{6-20}$ heteroarenediyl, $C_{7-20}$ alkanearenediyl, substituted $C_{7-20}$ alkanearenediyl, $C_{6-20}$ heteroalkanearenediyl, substituted $C_{6-20}$ heteroalkanearenediyl, and —$(CH_2)_{n1}$—$(CH_2$—$CH_2$—$O)_{n2}$—$(CH_2)_{n3}$—, wherein:
each n1 and n3 is independently an integer selected from 0 to 5; and
each n2 is independently an integer selected from 1 to 25;

each $X^2$ is independently selected from a covalent bond, —O—, —S—, —N—, —N=, —N=N—, —N=C—, —SO—, —SO$_2$—, —SO$_2$N—, —SS—, —C(O)—, —C(O)O—, —C(O)N—, —C(O)S—, —C(O)N—N=, —OP(O)(OH)O—, —OC(O)O—, —OC(O)N—, —NC(O)N—, and —NC(S)N;

each $R^1$ and $R^2$ is independently selected from hydrogen, $C_{1-6}$ alkyl, substituted $C_{1-6}$ alkyl, $C_{1-6}$ heteroalkyl, substituted $C_{1-6}$ heteroalkyl, $C_{6-10}$ aryl, substituted $C_{6-10}$ aryl, $C_{6-10}$ heteroaryl, and substituted $C_{6-10}$ heteroaryl;

each D is independently selected from therapeutic agent having at least one primary amine group, a therapeutic agent having at least one secondary amine group, a therapeutic agent having at least one hydroxy group, and a therapeutic agent having at least one thiol group; and n6 is an integer selected from 1 to 20.

In a third aspect, pharmaceutical compositions are disclosed comprising a compound of Formula (II), a compound of Formula (III), or a pharmaceutically acceptable salt of any of the foregoing, and a pharmaceutically acceptable carrier.

In a fourth aspect, methods of treating cancer, an autoimmune disease, or an infectious disease are disclosed, comprising administering to a patient in need of such treatment a therapeutically effective amount of a compound of Formula (II), Formula (III), a pharmaceutical salt of any of the foregoing, or a pharmaceutical composition comprising any one of the foregoing.

In a fifth aspect, methods of synthesizing compounds of Formula (I), Formula (II), and Formula (III), or a pharmaceutically acceptable salt of any of the foregoing are disclosed.

DETAILED DESCRIPTION

Definitions

A dash ("-") that is not between two letters or symbols is used to indicate a point of attachment for a substituent. For example, —CONH$_2$ is attached through the carbon atom.

Compounds provided by the present disclosure are encompassed by structural formulae disclosed herein and include any specific compounds within these formulae. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to one skilled in the art. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{13}$C, $^{14}$C, $^{15}$N, $^{18}$O, $^{17}$O, etc. Compounds may exist in unsolvated forms as well as solvated forms, including hydrated forms and as N-oxides. Accordingly, compounds may be hydrated, solvated, or N-oxides. Certain compounds may exist in multiple crystalline or amorphous forms. In general, all physical forms are equivalent for the uses contemplated herein and are intended to be within the scope of the present disclosure. Further, it should be understood, when partial structures of the compounds are illustrated, that brackets indicate the point of attachment of the partial structure to the rest of the molecule.

The term "acyl" means an H—C(O)—, alkyl-C(O)—, or cycloalkyl-C(O)— group wherein alkyl and cycloalkyl are as defined herein. In certain embodiments, an acyl group is $C_{1-8}$ acyl, $C_{1-6}$ acyl, $C_{1-4}$ acyl, and in certain embodiments, $C_{1-3}$ acyl.

The term "alkanearene" refers to a hydrocarbon group in which an alkyl group is bonded to an aromatic group, wherein alkyl and aromatic group are as defined herein. In certain embodiments, an alkanearene group is $C_{7-20}$ alkanearene, $C_{7-12}$ alkanearene, and in certain embodiments $C_{7-10}$ alkanearenediyl.

The term "alkanearenediyl" refers to a diradical hydrocarbon group derived by the removal of two hydrogen atoms from a single carbon atom or by the removal of a single hydrogen atom from two carbon atoms from a parent alkanearene group. In certain embodiments, an alkanearenediyl group is $C_{7-20}$ alkanearenediyl, $C_{7-12}$ alkanearenediyl, and in certain embodiments $C_{7-10}$ alkanearenediyl.

The term "alkanediyl" refers to a diradical of a saturated or unsaturated, branched, or straight-chain acyclic hydrocarbon group, having, for example, from 1 to 20 carbon atoms, from 1-10 carbon atoms, from 1-6 carbon atoms, from 1 to 4 carbon atoms, or from 1 to 3 hydrocarbon atoms. Examples of alkanediyl groups include methane-diyl (—CH$_2$—), ethane-1,2-diyl (—CH$_2$CH$_2$—), propane-1,3-diyl and iso-propane-1,2-diyl (e.g., —CH$_2$CH$_2$CH$_2$— and —CH(CH$_3$)CH$_2$—), butane-1,4-diyl (—CH$_2$CH$_2$CH$_2$CH$_2$—), pentane-1,5-diyl (—CH$_2$CH$_2$CH$_2$CH$_2$CH$_2$—), hexane-1,6-diyl (—CH$_2$CH$_2$CH$_2$CH$_2$CH$_2$CH$_2$—), heptane-1,7-diyl, octane-1,8-diyl, nonane-1,9-diyl, decane-1,10-diyl, dodecane-1,12-diyl, and the like.

The term "alkanecycloalkane" refers to a hydrocarbon group in which an alkyl group is bonded to a cycloalkane group, wherein alkyl and cycloalkane are as defined herein. In certain embodiments, an alkanecycloalkane group is $C_{7-20}$ alkanecycloalkane, $C_{7-12}$ alkanecycloalkane, and in certain embodiments $C_{7-10}$ alkanecycloalkane. In certain embodiments an alkanecycloalkane is selected from methylcyclohexane:

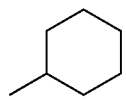

The term "alkanecycloalkanediyl" refers to a diradical hydrocarbon group derived by the removal of two hydrogen atoms from a single carbon atom or by the removal of a single hydrogen atom from two carbon atoms from a parent alkanecycloalkane group. In certain embodiments an alkanecycloalkanediyl is selected from 4-methylcyclohexane-diyl:

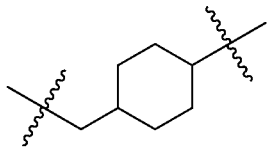 [SMILES: *CC1CCC(*)CC1]

The term "alkoxy" refers to an alkyl-O— group where alkyl is as defined herein. Examples of alkoxy groups include methoxy, ethoxy, n-propoxy, isopropoxy, and n-butoxy. In certain embodiments, an alkoxy group is $C_{1-8}$ alkoxy, $C_{1-6}$ alkoxy, $C_{1-4}$ alkoxy, and in certain embodiments $C_{1-3}$ alkoxy.

The term "alkyl" refers to a monoradical of a saturated or unsaturated, branched, or straight-chain acyclic hydrocarbon group having, for example, from 1 to 20 carbon atoms, from 1 to 10 carbon atoms, from 1 to 6 carbon atoms, from 1 to 4 carbon atoms, or from 1 to 3 carbon atoms. Examples of alkyl groups include methyl, ethyl, n-propyl, iso-propyl, n-butyl, iso-butyl, n-hexyl, n-decyl, tetradecyl, and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds.

The term "alkyne-reactive group" as used herein refers to a functional group capable of reacting with an alkyne in the presence or absence of a catalyst to form a triazole. Example of a catalyst includes Copper(I). Examples of alkyne-reactive groups include an azide group. In certain embodiments, an alkyne-reactive group is selected from Formula (A$^1$e1), Formula (A$^1$e2), and Formula (A$^1$d3):

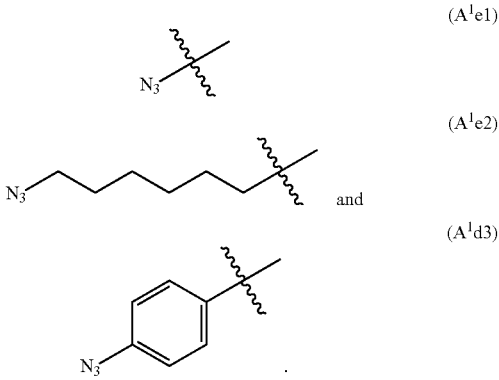

The term "amine-reactive group" as used herein refers to a functional group capable of reacting with a primary amine group, a secondary amine group, a hydrazine group, or a substituted hydrazine group to form an amide bond, a urea bond, a thiourea bond, a sulfonamide bond, a carbamate bond, an imine, or a hydrazone. Examples of an amine-reactive group include an aldehyde group, a ketone group, an NHS-ester group, a substituted phenylester group, an isocyanate group, an isothiocyanate group, and an alkyl imidate group. In certain embodiments, an amine-reactive group is selected from Formula (A¹b1), Formula (A¹b2), Formula (A¹b3), and Formula (A¹b4):

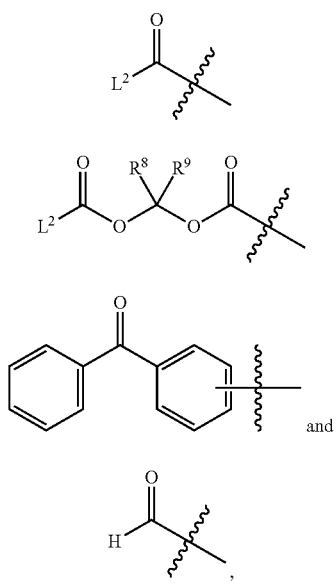

wherein each $R^8$ and $R^9$ is independently selected from hydrogen, $C_{1-4}$ alkyl, substituted $C_{1-4}$ alkyl, $C_{1-4}$ heteroalkyl, substituted $C_{1-4}$ heteroalkyl, $C_{6-10}$ aryl, substituted $C_{6-10}$ aryl, $C_{6-10}$ heteroaryl, and substituted $C_{6-10}$ heteroaryl; and $L^2$ is a leaving group such as a halogen, an N-hydroxysuccinimidyl, a substituted N-hydroxysuccinimidyl, a phenol-yl, a substituted phenol-yl, a hydroxybenzotriazolyl, a substituted hydroxybenzotriazolyl, an imidazolyl, and a substituted imidazolyl.

The term "amino acid side chain" includes the side chains of naturally occurring standard amino acids, side chains of naturally occurring non-standard amino acids, and side chains of non-naturally occurring amino acid derivatives. In certain embodiments, amino acid side chain includes naturally occurring standard amino acid side chains.

The term "anthracycline derivative" refers to a compound having the basic structural scaffold:

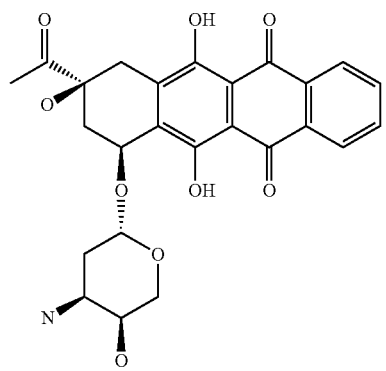 [SMILES: CC(=O)[C@]1(O)Cc2c(O)c3c(c(O)c2[C@@H](O[C@H]2C[C@H](N)[C@H](O)CO2)C1)C(=O)c1ccccc1C3=O]

and is effective in treating leukemias, lymphomas, and breast, uterine, ovarian, and/or lung cancers. Anthracycline derivatives interchelate with DNA and RNA, inhibit the enzyme topoisomerase II, and generate DNA-damaging free oxygen radicals. Examples of anthracycline derivatives include berubicin, daunorubicin, doxorubicin, epirubicin, idarubicin, amrubicin, pirarubicin, zorubicin, mitoxantrone, banoxantrone, and sabarubicin.

The term "anthracenedione derivative" refers to a compound having the basic structural scaffolds:

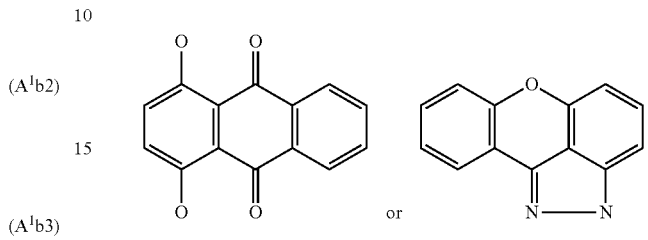

and is effective in treating metastatic breast cancer, acute lymphoblastic leukaemia, acute myeloid leukemia, non-Hodgkin's lymphoma, and/or multiple sclerosis. Anthracenedione derivatives interchelate with DNA and inhibit the enzyme topoisomerase II. Examples of anthracenedione derivatives include to ledoxantrone, mitoxantrone, nortopixantrone, pixantrone, piroxantrone, and topixantrone.

The term "antibiotic" refers to a compound that kills or slows the growth of bacteria, fungi, and/or other microorganisms. Examples of antibiotics include amikacin, amphotericin B, arbekacin, astromicin, bacitracin, balofloxacin, bederocin, bekanamycin, besifloxacin, brodimoprim, ciprofloxacin, clinafloxacin, colistin, daptomycin, dibekacin, enoxacin, framycetin, garenoxacin, gatifloxacin, gemifloxacin, gentamicin, gentamicin, grepafloxacin, hamycin, hexetidine, hygromycin B, ibacitabine, iclaprim, isepamicin, kanamycin, lomefloxacin, lucimycin, lymecycline, mepartricin, moxifloxacin, natamycin, nemonoxacin, neomycin B, neomycin C, netilmicin, norfloxacin, nystatin, omadacycline, oritavancin, paromomycin, pazufloxacin, perimycin A, perimycin B, perimycin C, pipemidic acid, polymyxin B, puromycin, radezolid, retaspimycin, ribostamycin, rimocidin, sisomicin, sitafloxacin, sparfloxacin, spectinomycin, streptomycin, sulfacetamide, sulfadiazine, sulfadimethoxine, sulfadimidine, sulfafurazole, sulfalene, sulfamazone, sulfameerazine, sulfamethizole, sulfamethoxazole, sulfamethoxypyridazine, sulfametomidine, sulfametoxydiazine, sulfametrole, sulfamoxole, sulfanilamide, sulfaperin, sulfaphenazole, sulfapyridine, sulfathiazole, sulfathiourea, sulfisomidine, teicoplanin, telavancin, tanespimycin, temafloxacin, tetroxoprim, tigecycline, tobramycin, tosufloxacin, trimethoprim, trimethoprim, trovafloxacin, tyrothricin, ulifloxacin, valnemulin, vancomycin, verdamicin, and zabofloxacin.

The term "antifolate" refers to a compound that is an analog of folic acid that inhibits the enzyme dihydrofolate reductase, thymidylate synthase, and/or other enzyme associated with the metabolism of nucleotides. Antifolates are known to be useful in treating cancer, rheumatoid arthritis, lupus, scleroderma, psoriasis, asthma, sarcoidosis, primary biliary cirrhosis, polymyositis, and/or inflammatory bowel disease. Examples of antifolates include aminopterin, folitixorin, methotrexate, pemetrexed, pralatrexate, raltitrexed, pelitrexol, pyrimethamine, talotrexin, and trimethoprim.

The term "arenediyl" refers to an aromatic hydrocarbon diradical derived by the removal of two hydrogen atoms from a single carbon atom or by the removal of a single hydrogen atom from two carbon atoms of a parent aromatic ring system.

In certain embodiments, an arenediyl group is $C_{6-20}$ arenediyl, $C_{6-12}$ arenediyl, $C_{6-10}$ arenediyl, and in certain embodiments, $C_{6-8}$ arenediyl. Examples of arenediyl groups include benzene-1,2-diyl, benzene-1,3-diyl, benzene-1,4-diyl, naphthalene-1,6-diyl, and the like.

The term "aryl" refers to a monovalent aromatic hydrocarbon radical derived by the removal of one hydrogen atom from a single carbon atom of a parent aromatic ring system. Aryl benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5-to 7-membered heterocycloalkyl ring containing one or more heteroatoms chosen from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can have from 6 to 20 carbon atoms ($C_{6-20}$), from 6 to 12 carbon atoms ($C_{6-12}$), from 6 to 10 carbon atoms ($C_{6-10}$), and in certain embodiments from 6 to 8 carbon atoms ($C_{6-8}$). Aryl, however, does not encompass or overlap in any way with heteroaryl, separately defined herein.

The term "aurora kinase inhibitor" refers to a compound that inhibits the enzyme aurora kinase, which regulates cellular mitosis. Aurora kinase inhibitors are being investigated for the treatment of cancer. Examples of aurora kinase inhibitors include barasertib, hesperadin, and tozasertib.

The term "avidin-binding group" as used herein refers to a biotin, a biotin derivative such as desthiobiotin, iminobiotin, bisnorbiotin, tetranorbiotin, biotin sulfoxide, biotin sulfone, and iminobiotin trifluoroacetamide, or a Strep-tag (a synthetic peptide consisting of an N-terminal or C-terminal eight amino acid sequence: Trp-Ser-His-Pro-Gln-Phe-Glu-Lys) capable of binding to avidin, deglycosylated avidin, streptavidin, Strep-Tactin or related proteins. In certain embodiments, an avidin-binding group is selected from Formula ($A^1c1$), Formula ($A^1c2$), and Formula ($A^1c3$):

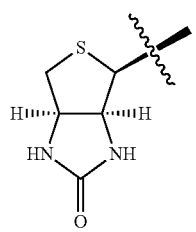

(A¹c1)

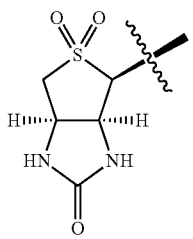

(A¹c2)

and

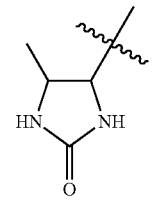

(A¹c3)

The term "azide-reactive group" as used herein refers to a functional group capable of reacting with an azide in the presence or absence of a catalyst to form a triazole. Example of a catalyst includes Copper(I). Examples of azide-reactive groups include a terminal alkyne group and an internal alkyne group. In certain embodiments, an azide-reactive group is selected from Formula ($A^1f1$), Formula ($A^1f2$), Formula ($A^1f3$), Formula ($A^1f4$), and Formula ($A^1f5$):

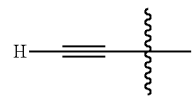

(A¹f1)

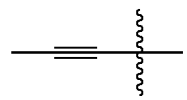

(A¹f2)

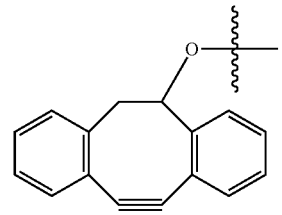

(A¹f3)

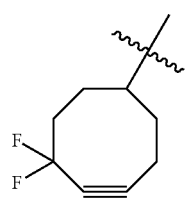

(A¹f4)

and

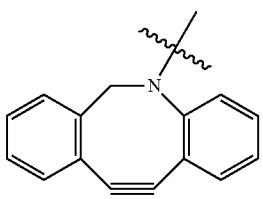

(A¹f5)

The term "camptotheca derivative" refers to a compound having the basic structural scaffold:

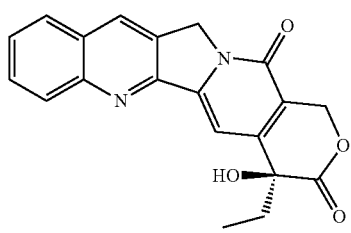 [SMILES: CC[C@@]1(O)C(=O)OCc2c1cc1n(c2=O)Cc2cc3ccccc3nc2-1]

and is effective in treating colon, ovarian, and/or lung cancers. Camptotheca derivatives inhibit the enzyme topoisomerase I and interfere with the unwinding of DNA. Examples of camptotheca derivatives include belotecan, atiratecan, exatecan, namitecan, 7-nbutyl-10-amino-camptothecin, and 7-n-butyl-9-amino-10,11-methylenedixoy-camptothecin.

The term "cathepsin K inhibitor" refers to a compound that inhibits the enzyme cathepsin K, which is associated with bone resorption. Cathepsin K inhibitors are being investigated for the treatment of bone cancer metastases. Examples of cathepsin K inhibitors include dutacatib and odanacatib.

The term "colchicine derivative" refers to a compound having the basic structural scaffold:

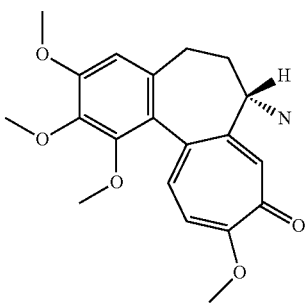 [SMILES: COc1cc2c(c(OC)c1OC)-c1ccc(OC)c(=O)cc1[C@@H](N)CC2]

and is potentially effective in treating cancer. Colchicine derivatives bind to tubulin P subunit and inhibit microtubule assembly. Examples of colchicine derivatives include demecolcine.

The term "crosslinker" as used herein refers to any chemical agent that joins two or more molecules through covalent bond(s) or through strong hydrogen-bonding(s).

The term "cyclin-dependent kinase inhibitor" refers to a compound that inhibits the enzyme cyclin-dependent kinase, which regulates cellular mitosis and transcription. Cyclin-dependent kinase inhibitors are being investigated for the treatment of cancer. Examples of cyclin-dependent kinase inhibitors include dinaciclib and seliciclib.

The term "cycloalkane" refers to a saturated or partially saturated cyclic or polycyclic hydrocarbon group. In certain embodiments, a cycloalkane group is $C_{3-12}$ cycloalkane, $C_{3-8}$ cycloalkane, $C_{3-6}$ cycloalkane, and in certain embodiments, $C_{5-6}$ cycloalkane.

The term "cycloalkanediyl" refers to a diradical cyclic or polycyclic hydrocarbon group. In certain embodiments, a cycloalkane-diyl group is $C_{3-12}$ cycloalkane-diyl, $C_{3-8}$ cycloalkane-diyl, $C_{3-6}$ cycloalkanediyl, and in certain embodiments, $C_{5-6}$ cycloalkanediyl. Examples of cycloalkanediyl groups include cyclohexane-1,4-diyl, cyclohexane-1,3-diyl, and cyclohexane-1,2-diyl.

The term "cycloalkyl" refers to a saturated or unsaturated cyclic or polycyclic hydrocarbon monoradical group. In certain embodiments, a cycloalkyl group is $C_{3-12}$ cycloalkyl, $C_{3-8}$ cycloalkyl, $C_{3-6}$ cycloalkyl, and in certain embodiments, $C_{5-6}$ cycloalkyl.

The term "dipeptidyl peptidase IV inhibitor" refers to a compound that inhibits the enzyme dipeptidyl peptidase IV, which is expressed on the surface of most cell types and is associated with immune regulation, signal transduction and apoptosis. Examples of dipeptidyl peptidase IV inhibitors include talabostat.

The term "dolastatin derivative" refers to a compound that is isolated or derived from the sea hare *Dolabella auricularia* or a structural analog thereof that binds to tubulin β subunit and inhibits microtubule assembly. Dolastatin derivatives are potentially effective in treating cancer. Examples of dolastatin derivatives include auristatin E, monomethyl auristatin E, auristatin F, monomethyl auristatin F, dolastatin 10, monomethyl dolastatin 10, dolastatin 12, dolastatin 15, soblidotin, monomethyl and dolastatin 16.

The term "duocarmycin derivative" refers to a compound that is isolated or derived from *Streptomyces* sp. or a structural analog thereof that alkylates DNA at minor groove sites. Duocarmycin derivatives are potentially effective in treating cancer. Examples of duocarmycin derivatives include duocarmycin A, duocarmycin SA, duocarmycin B, and duocarmycin B1.

The term "ecteinascidin derivative" refers to a compound that is isolated or derived from the sea squirt *Ecteinascidia turbinata* or a structural analog thereof that produces superoxide, resulting in DNA cleavage. Ectienascidin derivatives are potentially effective in treating cancer. Examples of ecteinascidin derivatives include trabectedin.

The term "enediyne derivative" refers to a compound that is isolated or derived from a bacterial natural product or a structural analog thereof characterized by either nine- and ten-membered rings containing two triple bonds separated by a double bond. Enediyne derivatives bind to and cleave DNA and are potentially effective in treating cancer. Examples of enediyne derivatives include calicheamicin γ1, calicheamicin T, esperamicin A1, esperamicin C, esperamicin D, dynemicin A, dynemicin H, dynemicin M, dynemicin N, dynemicin O, dynemicin P, dynemicin Q, dynemicin S, neocarzinostatin chromophore, and uncialamycin.

The term "epothilone derivative" refers to a compound that is isolated or derived from a myxobacterium *Sorangium cellulosum* or a structural analog thereof that interferes with mitotic spindle assembly. Epothilone derivatives are potentially effective in treating cancer, such as breast cancer. Examples of epothilone derivatives include ixabepilone and 21-aminoepothilone B.

The term "halichondrin derivative" refers to a compound isolated or derived from the marine sponge *Halichondria okadai* or a structural analog thereof that interferes with formation of microtubules. Halichondrin derivatives are effective in treating breast cancer. Examples of halichondrin derivatives include eribulin.

The term "heat shock protein 90 (Hsp90) inhibitor" refers to a compound that binds to and interferes with Hsp90, which plays an important role in oncogenesis. Examples of Hsp90 inhibitors include geldanamycin and alvespimycin.

The term "hemiasterlin derivative" refers to a compound that is isolated or derived from marine sponges (*Cymbastela* sp., *Hemiasterella minor*, *Siphonochalina* sp., and *Auletta* sp.) or a structural analog thereof that depolymerizes microtubules and interferes with cell division. Hemiasterlin derivatives are potentially effective in treating cancer. Examples of hemiasterlin derivatives include taltobulin and HTI-286.

The term "heteroalkanearenediyl" refers to an alkanenearenediyl group in which one or more of the carbon atoms are replaced with a heteroatom (e.g., N, O, S, P, or Si).

The term "heteroalkanecycloalkanediyl" refers to an alkanecycloalkanediyl group in which one or more of the carbon atoms are replaced with a heteroatom (e.g., N, O, S, P, or Si).

The term "heteroalkanediyl" refers to an alkanediyl group in which one or more of the carbon atoms is replaced with a heteroatom (e.g., N, O, S, P, or Si).

The term "heteroalkyl" refers to an alkyl group in which one or more of the carbon atoms are replaced with a heteroatom (e.g., N, O, S, P, or Si).

The term "heteroarenediyl" refers to an arenediyl group wherein one or more of the carbon atoms are replaced with a heteroatom (e.g., N, O, S, P, or Si). Examples of heteroarenediyl groups include furane-diyl and pyridine-diyl.

The term "heteroaryl" refers to an aryl group wherein one or more of the ring carbon atoms are replaced with a heteroatom (e.g., N, O, S, P, or Si). Examples of heteroaryl groups include, but are not limited to, monoradicals of acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is $C_{5-20}$ heteroaryl, $C_{5-12}$ heteroaryl, $C_{5-8}$ heteroaryl, and in certain embodiments, $C_{5-6}$ heteroaryl. In certain embodiments heteroaryl groups are those derived from thiophene, pyrrole, benzothiophene, benzofuran, indole, pyridine, quinoline, imidazole, oxazole, and pyrazine.

The term "heterocycloalkanediyl" refers to a cycloalkanediyl group in which one or more of the carbon atoms are replaced with a heteroatom (e.g., N, O, S, P, or Si).

The term "heterocycloalkyl" refers to a cycloalkyl group in which one or more of the carbon atoms are replaced with a heteroatom (e.g., N, O, S, P, or Si).

The term "histone deacetylase inhibitor" refers to a compound that interferes with the enzyme histone deacetylase, which involves with the coiling of DNA around histones. Histone diacetylase inhibitors are being investigated for the treatment of lymphoma, breast, and lung cancers. Examples of histone deacetylase inhibitors include entinostat, mocetinostat, panobinostat, and tacedinaline.

The term "immunomodulator" refers to a compound that stimulates and/or suppresses the immune system. Examples of immunomodulators include apilimod, balamapimod, dilmapimod, epetirimod, fingolimod, golotimod, imiquimod, lenalidomide, losmapimod, myriocin, pamapimod, resiquimod, gusperimus, pomalidomide, and sotirimod.

The term "kahalalide derivative" refers to a compound that is isolated or derived from to the marine mollusk *Elysia rufescens* or a structural analog thereof that is active against certain human prostate and breast cancer cell lines. Kahalalide derivatives are potentially effective in treating cancer. Examples of kahalalide derivatives include kahalalide F and elisidepsin.

The term "kinesin-related motor protein Eg5 inhibitor" refers to a compound that inhibits the motor protein Eg5, which is involved in the regulation of spindle formation during mitosis. Kinesin-related motor protein Eg5 inhibitors are being investigated for the treatment of cancer. Examples of kinesin-related motor protein Eg5 inhibitor include litronesib.

The term "kinesin spindle protein inhibitor" refers to a compound that inhibits the kinesin spindle protein, which involves in the assembly of the bipolar spindle during cell division. Kinesin spindle protein inhibitors are being investigated for the treatment of cancer. Examples of kinesin spindle protein inhibitor include ispinesib.

The term "ligand" as used herein refers to an organic compound or inorganic substrate that contains or is functionalized to contain at least one thiol group, at least one primary amine group, at least one secondary amine group, at least one biotin-binding group, at least one photoreactive group, at least one alkyne group, at least one azide group, or a combination of any of the foregoing. The function of the ligand, for example, is to prolong the in-vivo half-life of the drug, reduce dosing frequency, lower toxicity, enhance the targeted delivery of the drug, and/or enable parallel in-vitro analysis. The inorganic substrate may be, for example, a glass bead or surface and a gold bead or surface, The organic compound may be, for example, a $C_{6-20}$ hydrocarbon, a natural or modified peptide, a natural or modified protein, a natural or modified antibody, a natural or modified nucleoside, a natural or modified nucleotide, a natural or modified oligonucleotide, a sugar, a natural or modified oligosaccharide, an aminoglycoside (antibiotic), or a natural or modified polymer or copolymer such as a polylactide, a polystyrene surface, a polystyrene bead, a dendrimer, a polyalkylene oxide, or a polyethylene oxide. A ligand can contain a thiol group, an amine group, a biotin-binding group, an alkyne group, an azide group, and/or a photoreactive group, or may be functionalized to contain thiol group, an amine group, a biotin-binding group, an alkyne group, an azide group, and/or a photoreactive group.

Examples of peptides include glutathione, carnosine, and pantetheine.

Examples of proteins include bovine serum albumin, human serum albumin, avidin, and strepavidin.

Examples of antibodies include polyclonal antibodies, monoclonal antibodies, murine monoclonal antibodies, chimeric monoclonal antibodies, fusion proteins, humanized monoclonal antibodies, and human monoclonal antibodies. In certain embodiments, an antibody is a humanized monoclonal antibody and is selected from Afutuzumab, Alemtuzumab, Bevacizumab, Bivatuzumab, Cantuzumab, Citatuzumab, Dacetuzumab, Elotuzumab, Etaracizumab, Farletuzumab, Gemtuzumab ozogamicin, Inotuzumab ozogamicin, Labetuzumab, Lintuzumab, Matuzumab§, Milatuzumab, Nimotuzumab, Oportuzumab monatox, Pertuzumab, Sibrotuzumab, Tacatuzumab tetraxetan, Tigatuzumab, Trastuzumab, Tucotuzumab celmoleukin, Veltuzumab, Aselizumab, Apolizumab, Benralizumab, Cedelizumab, Certolizumab, Daclizumab, Eculizumab, Efalizumab, Epratuzumab, Erlizumab, Fontolizumab, Mepolizumab, Natalizumab, Ocrelizumab, Omalizumab, Pascolizumab, Pexelizumab, PRO 140, Reslizumab, Rontalizumab, Rovelizumab, Ruplizumab, Siplizumab, Talizumab, Teplizumab, Tocilizumab, Toralizumab, Vedolizumab, Visilizumab, TGN1412, Ibalizumab, Tefibazumab, Alacizumab pegol, Bevacizumab/Ranibizumab, Etaracizumab, Tadocizumab, Bapineuzumab, Solanezumab, Tanezumab, Urtoxazumab, Felvizumab, Motavizumab, Palivizumab, Lebrikizumab, and Ranibizumab. In certain embodiments, an antibody is a murine monoclonal antibody and is selected from Abagovomab, Igovomab, Oregovomab, Afelimomab, Elsilimomab, Faralimomab, Gavilimomab, Inolimomab, Maslimomab, Nerelimomab, Odulimomab, Telimomab aritox, Vepalimomab, Zolimomab aritox, Altumomab pentetate, Anatumomab mafenatox, Arcitumomab, Bectumomab, Blinatumomab, CC49, Detumomab, Ibritumomab tiuxetan, Minretumomab, Mitumomab, Naptumomab estafenatox, Nofetumomab merpentan, Pemtumomab, Pintumomab, Satumomab pendetide, Taplitumomab paptox, Tenatumomab, Tositumomab, 3F8, Besilesomab, Fanolesomab, Lemalesomab, Sulesomab, Biciromab, Imciromab, Capromab pendetide, Edobacomab, Edrecolomab, and Nacolomab tafenatox. In certain embodiments, an antibody is a chimeric monoclonal antibody and is selected from Bavituximab, Brentuximab vedotin, Cetuximab, Siltuximab, Rituximab, Abciximab, Volociximab, Basiliximab, Clenoliximab, Galiximab, Gomiliximab, Infliximab, Keliximab, Lumiliximab, Priliximab, Teneliximab, Vapaliximab, Ecromeximab, and Pagibaximab. In certain embodiments, an antibody is a human monoclonal antibody and is selected from Adalimumab, Atorolimumab, Fresolimumab, Golimumab, Lerdelimumab, Metelimumab, Morolimumab, Ipilimumab, Tremelimumab, Bertilimumab, Zanolimumab, Briakinumab, Canakinumab, Ustekinumab, Adecatumumab, Belimumab, Cixutumumab, Conatumumab, Figitumumab, Iratumumab, Lexatumumab, Lucatumumab, Mapatumumab, Necitumumab, Ofatumumab, Olaratumab, Panitumumab, Pritumumab, Robatumumab, Votumumab, Zalutumumab, Denosumab, Stamulumab, Efungumab, Exbivirumab, Foravirumab, Libivirumab, Rafivirumab, Regavirumab, Sevirumab, Tuvirumab, Nebacumab, Panobacumab, Raxibacumab, Ramucirumab, Gantenerumab, and Glembatumumab.

Examples of nucleosides include thymidine, cytidine, uridine, adenosine, and guanosine.

Examples of oligonucleotides include single-stranded and double-stranded oligoribonucleotides, oligoribonucleotide derivatives, oligodeoxyribonucleotides, and oligodeoxyribonucleotide derivatives such as phosphorothioates, phosphoramidates, and phosphorothioamidates.

Examples of oligonucleotides also include oblimersen and imetelstat.

Examples of sugars include glucosamine.

Examples of aminoglycosides include streptomycin, neomycin, framycetin, paromomycin, ribostamycin, kanamycin, amikacin, arbekacin, bekanamycin, dibekacin, tobramycin, spectinomycin, hygromycin B, paromomycin sulfate, gentamicin, netilmicin, sisomicin, isepamicin, verdamicin, and astromicin.

Examples of oligosaccharides include polyglucosamine (chitosan).

Examples of polymers include polyethylene glycol (PEG), monomethyl polyethylene glycol (MPEG), polypropylene glycol (PPG), polylactide, N-(2-hydroxypropyl)methacrylamide (HPMA) copolymer, and poly(styrene-co-maleic acid). In certain embodiments, the polymer is MPEG having a number average molecular weight from about 200 to about 60,000 Daltons, from about 1,000 to about 40,000 Daltons, and in certain embodiments, from about 2,000 to about 12,500 Daltons.

Examples of dendrimers include poly(amidoamine) dentrimers (PAMAM) and poly(propylenimine) dentrimers (PPI).

The term "microtubule interference compounds" refers to a class of compounds that disrupt the polymerization or depolymerization of microtubules during mitosis. Microtublue interference compounds are being used and investigated for the treatment of various cancers. Examples of microtubule interference compounds include vinca alkaloid derivatives, cevipabulin, denibulin, and ombrabulin.

The term "parent aromatic ring system" refers to an unsaturated cyclic or polycyclic ring system having a conjugated π electron system. Included within the definition of "parent aromatic ring system" are fused ring systems in which one or more of the rings are aromatic and one or more of the rings are saturated or unsaturated, such as, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene.

The term "parent heteroaromatic ring system" refers to a parent aromatic ring system in which one or more carbon atoms (and any associated hydrogen atoms) are independently replaced with the same or different heteroatom. Examples of heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, and xanthene.

The term "patient" includes mammals, such as for example, humans. The terms "patient" and "patient" are used interchangeably.

The term "pharmaceutical composition" refers to at least one compound and a pharmaceutically acceptable vehicle with which the compound is administered to a patient.

The term "pharmaceutically acceptable" refers to approved or approvable by a regulatory agency of the Federal or a state government or listed in the U.S. Pharmacopoeia or other generally recognized pharmacopoeia for use in animals, including humans.

The term "pharmaceutically acceptable salt" refers to a salt of a compound, which possesses the desired pharmacological activity of the parent compound. Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, a pharmaceutically acceptable salt is the hydrochloride salt. In certain embodiments, a pharmaceutically acceptable salt is the sodium salt. The term "pharmaceutically acceptable salt" includes hydrates and other solvates, as well as salts in crystalline or non-crystalline form.

The term "pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound can be administered to a patient and which does not destroy the pharmacological activity thereof and which is nontoxic when administered in doses sufficient to provide a therapeutically effective amount of the compound.

The term "photoreactive group" as used herein refers to a functional group capable of reacting with a primary, secondary or tertiary amine upon exposure to actinic radiation, such as ultraviolet light, to form at least one covalent bond. Examples of photoreactive groups include an azide group, a diaziridine group, a coumarin group, and a psoralen group. In certain embodiments, a photoreactive group is selected from Formula ($A^1d1$), Formula ($A^1d2$), Formula ($A^1d3$), Formula ($A^1d4$), Formula ($A^1d5$), Formula ($A^1d6$), Formula ($A^1d7$), and Formula ($A^1d8$):

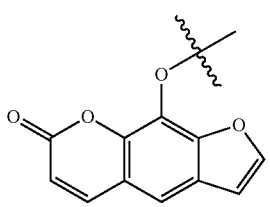

($A^1d1$)

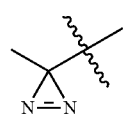

($A^1d2$)

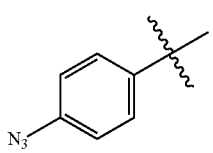

($A^1d3$)

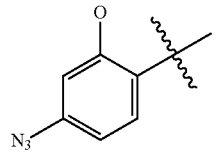

($A^1d4$)

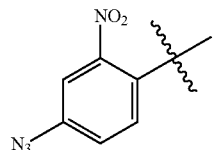

($A^1d5$)

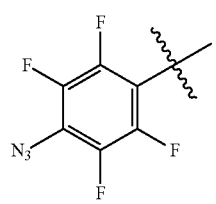

($A^1d6$)

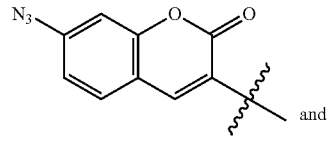

($A^1d7$)

and

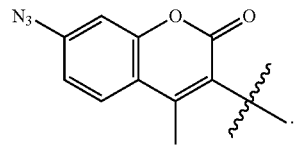

($A^1d8$)

Examples of photoreactive groups are also disclosed in U.S. Publication No. 2001/00022761.

The term "poly (ADP-ribose) polymerase (PARP) inhibitor" refers to a compound that inhibits the enzyme PARP, which is associated with DNA repair and programmed cell death. Examples of a PARP inhibitors include veliparib.

The term "purine analog" refers to a compound that mimics the nucleoside adenosine, nucleoside guanosine, nucleobase adenine, or nucleobase guanine and interferes with the DNA replication. Purine analogs are effective in treating certain cancers. Examples of purine analogs include deoxycoformycin, cladribine, clofarabine, fludarabine, thioguanine, and mercaptopurine.

The term "pyrimidine analog" refers to a compound that mimics the deoxynucleoside thymidine, nucleoside cytidine, nucleoside uridine, nucleobase thymine, nucleobase cytosine or nucleobase uracil and interferes with the DNA replication. Pyrimidine analogs are effective in treating certain cancers. Examples of pyrimidine analogs include azacitidine, cytarabine, decitabine, and gemcitabine.

The term "pyrrolobenzodiazepine" refers to a compound that is isolated or derived from *Streptomyces* sp. or a structural analog thereof that alkylates DNA at minor groove sites. Pyrrolobenzodiazepine is potentially effective in treating cancer. Examples of pyrrolobenzodiazepine include abbeymycin, anthramycin, centanamycin, chicamycin, mazethramycin, porothramycin A, porothramycin B, sibanomycin, and sibiromycin.

The term "*streptomyces*" refers to a compound that is isolated or derived from the bacteria *Streptomyces* or a structural analog thereof that has antibacterial, antifungal, anti-parasitic, and/or antineoplastic properties. Examples of *streptomyces* include actinomycin D, 7-aminoactinomycin D, bleomycin, mitomycin, and staurosporine.

The term "substituted" refers to a group in which one or more hydrogen atoms are each independently replaced with the same or different substituent(s). In certain embodiments, a substituent is selected from halogen, —S(O)$_2$OH, —S(O)$_2$—C$_{1-6}$ alkyl, —SH, —S—C$_{1-6}$ alkyl, —COOH, —CONH$_2$, —N$_3$, —NO$_2$, —NH$_2$, —NH(C$_{1-6}$ alkyl), —N(C$_{1-6}$ alkyl)$_2$, —CN, =O, C$_{1-6}$ alkyl, —CF$_3$, —OH, C$_{6-8}$ aryl, C$_{1-6}$ heteroalkyl, C$_{5-8}$ heteroaryl, C$_{1-6}$ alkoxy, C$_{1-6}$ acyl, and —COR where R is C$_{1-6}$ alkyl. In certain embodiments, a substituent is chosen from —OH, —NH$_2$, and C$_{1-6}$ alkyl.

The term "therapeutic agent" or "drug" refers to a compound known to be or believed to be effective in treating a disease in a patient.

The term "therapeutically effective amount" refers to the amount of a compound that, when administered to a patient for treating a disease in a patient, is sufficient to reduce, minimize, and/or prevent the disease. A "therapeutically effective amount" can vary depending, for example, on the compound, the nature or cause of the disease, severity of the disease, the age, weight, and/or health of the patient to be treated, and the judgment of the prescribing physician. An appropriate amount in any given instance can be ascertained by those skilled in the art or capable of determination by routine experimentation. The terms "therapeutically effective amount" and "prophylactically effective amount" are used interchangeably. A therapeutically effective amount can also mean a dose that has been recommended or approved by any of the various regulatory or advisory organizations in the medical or pharmaceutical arts (e.g., FDA, AMA) or by the manufacturer or supplier.

The term "therapeutically effective dose" refers to a dose that provides effective treatment of a disease or disorder in a patient. A therapeutically effective dose can vary from compound to compound, and from patient to patient, and can depend upon factors such as the condition of the patient and the route of delivery. A therapeutically effective dose can be determined in accordance with routine pharmacological procedures known to those skilled in the art.

The term "thiol-reactive group" as used herein refers to a functional group capable of reacting with a thiol group to form a thiol ether bond, a disulfide bond, or a thiourea bond. Examples of a thiol-reactive group include a vinyl group (—CH=CH$_2$), a haloalkyl group, a haloacetyl group, and an isocyanate group (—NCO). In certain embodiments a thiol-reactive group is selected from Formula (A$^1$a1), Formula (A$^1$a2), Formula (A$^1$a3), and Formula (A$^1$a4):

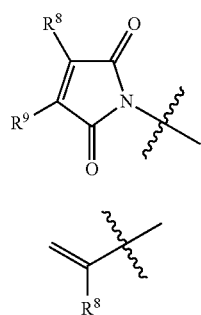
(A$^1$a1)

(A$^1$a2)

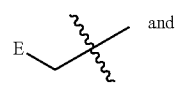
(A$^1$a3)

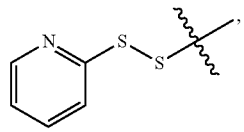
(A$^1$a4)

wherein each R$^8$ and R$^9$ is independently selected from hydrogen, C$_{1-4}$ alkyl, substituted C$_{1-4}$ alkyl, C$_{1-4}$ heteroalkyl, substituted C$_{1-4}$ heteroalkyl, C$_{6-10}$ aryl, substituted C$_{6-10}$ aryl, C$_{6-10}$ heteroaryl, and substituted C$_{6-10}$ heteroaryl; and each E is selected from F, Cl, Br, and I.

The term "topoisomerase inhibitor" refers to a compound that inhibits the enzyme topoisomerase, which involves in the unwinding and winding of DNA during transcription and replication. Topoisomerase inhibitors are being used and investigated for the treatment of various cancers. Examples of topoisomerase inhibitors include camptotheca derivatives and edotecarin.

The term "treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, and to inhibiting at least one physical parameter which may or may not be discernible to the patient. In certain embodiments, "treating" or "treatment" refers to delaying the onset of the disease or disorder or at least one or more symptoms thereof in a patient which may be exposed to or predisposed to a disease or disorder even though that patient does not yet experience or display symptoms of the disease or disorder.

The term "tubulysin derivative" refers to a compound having the basic structural scaffold:

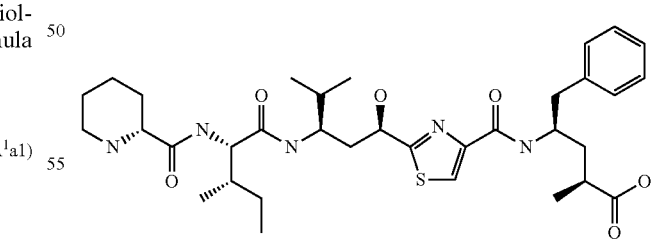

and is potentially effective in treating cancer. Tubulysin derivatives depolymerize microtubules and induce mitotic arrest. Examples of tubulysin derivatives include tubulysin A, tubulysin B, and tubulysin D.

The term "tyrosine kinase inhibitor" refers to a compound that inhibits the enzyme tyrosine kinase, which regulates cellular activity through the phosphorylation of the amino acid tyrosine of a signaling protein. Tyrosine kinase inhibitors are effective in treating chronic myelogenous leukemia and are being for the treatment of other cancers. Examples of tyrosine kinase inhibitors include afatinib, bosutinib, canertinib, crizotinib, dacomitinib, dasatinib, dovitinib, erlotinib, fostamatinib, gefitinib, imatinib, intedanib, lapatinib, linifanib, masitinib, motesanib, neratinib, nilotinib, pazopanib, saracatinib, selumetinib, telatinib, tipifarnib, vandetanib, and vatalanib.

The term "vinca alkaloid derivative" refers to a compound isolated or derived from a plant Madagascar Periwinkle or a structural analog thereof that inhibits microtubule polymerization. Examples of vinca alkaloid derivatives include desacetylvinblastine hydrazide, vinblastine, vincristine, vindestine, vinflunine, and vinorelbine.

Compounds are named using Symyx Draw 3.3, Symyx Solutions Inc., 2010.

Reference is now made in detail to certain embodiments of compounds, compositions, and methods. The disclosed embodiments are not intended to be limiting of the claims. To the contrary, the claims are intended to cover all alternatives, modifications, and equivalents.

Cleavable Conjugates

In certain embodiments, a compound provided by the present disclosure has the structure of Formula (II):

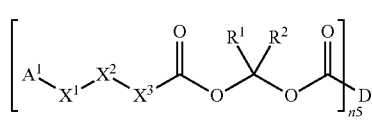
(II)

or a salt thereof, wherein:
each $A^1$ is independently selected from a thiol-reactive group, an amine-reactive group, an avidin-binding group, a photoreactive group, an alkyne-reactive group, and an azide-reactive group;
each $X^1$ and $X^3$ is independently selected from a covalent bond, $C_{1-20}$ alkanediyl, substituted $C_{1-20}$ alkanediyl, $C_{1-20}$ heteroalkanediyl, substituted $C_{1-20}$ heteroalkanediyl, $C_{3-12}$ cycloalkanediyl, substituted $C_{3-12}$ cycloalkanediyl, $C_{3-12}$ heterocycloalkanediyl, substituted $C_{3-12}$ heterocycloalkanediyl, $C_{4-20}$ alkanecycloalkanediyl, substituted $C_{4-20}$ alkanecycloalkanediyl, $C_{4-20}$ heteroalkanecycloalkanediyl, substituted $C_{4-20}$ heteroalkanecycloalkanediyl, $C_{6-20}$ arenediyl, substituted $C_{6-20}$ arenediyl, $C_{6-20}$ heteroarenediyl, substituted $C_{6-20}$ heteroarenediyl, $C_{7-20}$ alkanearenediyl, substituted $C_{7-20}$ alkanearenediyl, $C_{6-20}$ heteroalkanearenediyl, substituted $C_{6-20}$ heteroalkanearenediyl, and —(CH$_2$)$_{n1}$—(CH$_2$—CH$_2$—O)$_{n2}$—(CH$_2$)$_{n3}$—,
wherein:
each n1 and n3 is independently an integer selected from 0 to 5; and
each n2 is independently an integer selected from 1 to 25;
each $X^2$ is independently selected from a covalent bond, —O—, —S—, —N—, —N=, —N=N—, —N=C—, —SO—, —SO$_2$—, —SO$_2$N—, —SS—, —C(O)—, —C(O)O—, —C(O)N—, —C(O)S—, —C(O)N—N=, —OP(O)(OH)O—, —OC(O)O—, —OC(O)N—, —NC(O)N—, and —NC(S)N;
each $R^1$ and $R^2$ is independently selected from hydrogen, $C_{1-6}$ alkyl, substituted $C_{1-6}$ alkyl, $C_{1-6}$ heteroalkyl, substituted $C_{1-6}$ heteroalkyl, $C_{6-10}$ aryl, substituted $C_{6-10}$ aryl, $C_{6-10}$ heteroaryl, and substituted $C_{6-10}$ heteroaryl;
D is selected from a therapeutic agent having at least one primary amine group, a therapeutic agent having at least one secondary amine group, a therapeutic agent having at least one hydroxy group, and a therapeutic agent having at least one thiol group; and
n5 is an integer selected from 1 to 20.

In certain embodiments of a compound of Formula (II), each $A^1$ is the same, and in certain embodiments, at least some $A^1$ are different.

In certain embodiments of a compound of Formula (II), each $X^1$ is the same, and in certain embodiments, at least some $X^1$ are different.

In certain embodiments of a compound of Formula (II), each $X^2$ is the same, and in certain embodiments, at least some $X^2$ are different.

In certain embodiments of a compound of Formula (II), each $X^3$ is the same, and in certain embodiments, at least some $X^3$ are different.

In certain embodiments of a compound of Formula (II), each $R^1$ is the same, and in certain embodiments, at least some $R^1$ are different.

In certain embodiments of a compound of Formula (II), each $R^2$ is the same, and in certain embodiments, at least some $R^2$ are different.

In certain embodiments of a compound of Formula (II), each group within the brackets is the same, and in certain embodiments, at least one group within the brackets is different.

In certain embodiments of a compound of Formula (II), each $A^1$ is independently a moiety selected from Formula ($A^1$a1), Formula ($A^1$a2), Formula ($A^1$a3), Formula ($A^1$b1), Formula ($A^1$b2), Formula ($A^1$c1), Formula ($A^1$c2), Formula ($A^1$c3), Formula ($A^1$d1), Formula ($A^1$d2), Formula ($A^1$d3), Formula ($A^1$e1), Formula ($A^1$f1), and Formula ($A^1$f2):

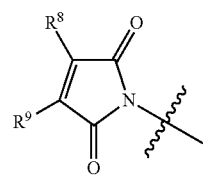
($A^1$a1)

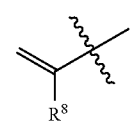
($A^1$a2)

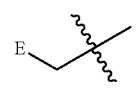
($A^1$a3)

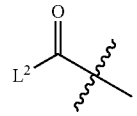
($A^1$b1)

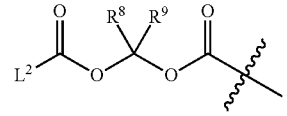
($A^1$b2)

(A¹c1)
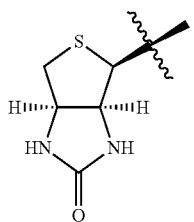

(A¹c2)
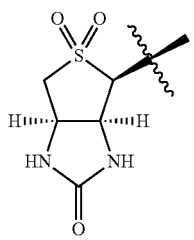

(A¹c3)
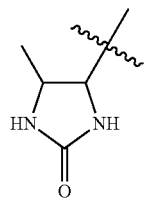

(A¹d1)
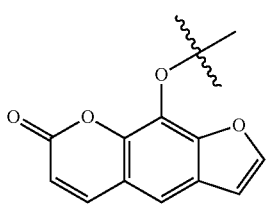

(A¹d2)
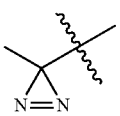

(A¹d3)
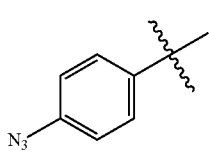

(A¹e1)

(A¹f1)
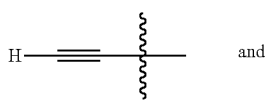

and (A¹f2)
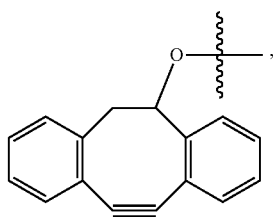

wherein:

each $R^8$ and $R^9$ is independently selected from hydrogen, $C_{1-4}$ alkyl, substituted $C_{1-4}$ alkyl, $C_{1-4}$ heteroalkyl, substituted $C_{1-4}$ heteroalkyl, $C_{6-10}$ aryl, substituted $C_{6-10}$ aryl, $C_{6-10}$ heteroaryl, and substituted $C_{6-10}$ heteroaryl;

each E is selected from F, Cl, Br, and I; and each $L^2$ is selected from halogen, N-hydroxysuccinimidyl, substituted N-hydroxysuccinimidyl, phenol-yl, substituted phenol-yl, hydroxybenzotriazolyl, substituted hydroxybenzotriazolyl, imidazolyl, and substituted imidazolyl.

In certain embodiments of a compound of Formula (II), each $A^1$ is independently selected from a thiol-reactive group, each $A^1$ is independently selected from an amine-reactive group, each $A^1$ is independently selected from an avidin-binding group, and in certain embodiments, each $A^1$ is independently selected from a photoreactive group, each $A^1$ is independently selected from an alkyne-reactive group, and each $A^1$ is independently selected from an azide-reactive group.

In certain embodiments of a compound of Formula (II), each $A^1$ is a thiol-reactive group and is independently selected from Formula ($A^1$a1), Formula ($A^1$a2), and Formula ($A^1$a3). In certain embodiments of a compound of Formula (II), each $A^1$ is an amine-reactive group and is independently selected from Formula ($A^1$b1) and Formula ($A^1$b2). In certain embodiments of Formula (II), each $A^1$ is an avidin-binding group and is independently selected from Formula ($A^1$c1), Formula ($A^1$c2), and Formula ($A^1$c3). In certain embodiments of a compound of Formula (II), each $A^1$ is a photoreactive group and is independently selected from Formula ($A^1$d1), Formula ($A^1$d2), and Formula ($A^1$d3). In certain embodiments of a compound of Formula (II), each $A^1$ is an alkyne-reactive group of Formula ($A^1$e1). In certain embodiments of a compound of Formula (II), each $A^1$ is an azide-reactive group and is independently selected from Formula ($A^1$f1) and Formula ($A^1$f2).

In certain embodiments of a compound of Formula (II), each $A^1$ is Formula ($A^1$a1). In certain embodiments of a compound of Formula (II), each $A^1$ is Formula ($A^1$a1), wherein each $R^8$ and $R^9$ is independently selected from hydrogen, $C_{1-4}$ alkyl and $C_{6-8}$ aryl; in certain embodiments, each $R^8$ and $R^9$ is independently selected from hydrogen, $C_{1-2}$ alkyl, and $C_6$ aryl; and in certain embodiments, each $R^8$ and $R^9$ is hydrogen.

In certain embodiments of a compound of Formula (II), each $A^1$ is Formula ($A^1$a2). In certain embodiments of a compound of Formula (II), each $A^1$ is Formula ($A^1$a2), wherein each $R^8$ is selected from hydrogen and $C_{1-4}$ alkyl; and in certain embodiments, each $R^8$ is selected from hydrogen and methyl.

In certain embodiments of a compound of Formula (II), each $A^1$ is Formula ($A^1$a3). In certain embodiments of a compound of Formula (II), each $A^1$ is Formula ($A^1$a3), wherein each E is selected from F, Cl, Br, and I; and in certain embodiments each E is selected from Br and I.

In certain embodiments of a compound of Formula (II), each $A^1$ is Formula ($A^1$b1). In certain embodiments of a compound of Formula (II) wherein each $A^1$ is Formula ($A^1$b1), each $L^2$ is selected from Cl, N-hydroxysuccinimidyl, sulfo-N hydroxysuccinimidyl, 4-nitrophenol-yl, pentafluorophenol-yl, 4-methylsulfonylphenol-yl, and trichlorophenol-yl.

In certain embodiments of a compound of Formula (II), each $A^1$ is Formula ($A^1$b2). In certain embodiments of a compound of Formula (II) wherein each $A^1$ is Formula ($A^1$b2), each $R^8$ and $R^9$ is independently selected from hydrogen, $C_{1-4}$ alkyl, and $C_{6-8}$ aryl, and each $L^2$ is selected from Cl, N-hydroxysuccinimidyl, sulfo-N hydroxysuccinimidyl, 4-nitrophenol-yl, pentafluorophenol-yl, 4-methylsulfonylphenol-yl, and trichlorophenol-yl. In certain embodiments of a compound of Formula (II) wherein each $A^1$ is Formula ($A^1$b2), each $R^8$ and $R^9$ is independently selected from hydrogen, methyl, ethyl, propyl, isopropyl, and phenyl, and each $L^2$ is selected from Cl, N-hydroxysuccinimidyl, sulfo-N hydroxysuccinimidyl, 4-nitrophenol-yl, pentafluorophenol-yl, 4-methylsulfonylphenol-yl, and trichlorophenol-yl. In certain embodiments of a compound of Formula (II) wherein each $A^1$ is Formula ($A^1$b2), each $R^8$ and $R^9$ is hydrogen, and each $L^2$ is selected from Cl, N-hydroxysuccinimidyl, sulfo-N hydroxysuccinimidyl, 4-nitrophenol-yl, pentafluorophenol-yl, 4-methylsulfonylphenol-yl, and trichlorophenol-yl.

In certain embodiments of a compound of Formula (II), each $A^1$ is Formula ($A^1$c1). In certain embodiments of a compound of Formula (II), each $A^1$ is Formula ($A^1$c2). In certain embodiments of a compound of Formula (II), each $A^1$ is Formula ($A^1$c3). In certain embodiments of a compound of Formula (II), each $A^1$ is Formula ($A^1$d1). In certain embodiments of a compound of Formula (II), each $A^1$ is Formula ($A^1$d2). In certain embodiments of a compound of Formula (II), each $A^1$ is Formula ($A^1$d3). In certain embodiments of a compound of Formula (II), each $A^1$ is Formula ($A^1$e1). In certain embodiments of a compound of Formula (II), each $A^1$ is Formula ($A^1$f1). In certain embodiments of a compound of Formula (II), each $A^1$ is Formula ($A^1$f2).

In certain embodiments of a compound of Formula (II), each $X^1$ and $X^3$ is independently selected from a covalent bond, $C_{1-20}$ alkanediyl, substituted $C_{1-20}$ alkanediyl, $C_3$-12 cycloalkanediyl, substituted $C_{3-12}$ cycloalkanediyl, substituted $C_{3-12}$ heterocycloalkanediyl, $C_{6-20}$ arenediyl, substituted $C_{6-20}$ arenediyl, $C_{7-20}$ alkanearenediyl, substituted $C_{7-20}$ alkanearenediyl, and —$(CH_2)_{n1}$—$(CH_2$—$CH_2$—$O)_{n2}$—$(CH_2)_{n3}$—, wherein each n1 and n3 is independently an integer selected from 0 to 5 and each n2 is independently an integer selected from 1 to 25.

In certain embodiments of a compound of Formula (II), each $X^1$ and $X^3$ is independently selected from a covalent bond, $C_{1-16}$ alkanediyl, substituted $C_{1-16}$ alkanediyl, $C_{3-6}$ cycloalkanediyl, benzene-diyl, substituted benzene-diyl, $C_{7-9}$ benzenealkane-diyl, and —$(CH_2)_{n1}$—$(CH_2$—$CH_2$—$O)_{n2}$—$(CH_2)_{n3}$—, wherein each n1 and n3 is independently an integer selected from 0 to 5 and each n2 is independently an integer selected from 1 to 20.

In certain embodiments of a compound of Formula (II), each $X^1$ and $X^3$ is independently selected from a covalent bond, $C_{1-8}$ alkanediyl, substituted $C_{1-8}$ alkanediyl, $C_{3-8}$ cycloalkanediyl, benzene-diyl, substituted benzene-diyl, $C_{7-9}$ benzenealkane-diyl, and —$(CH_2)_{n1}$—$(CH_2$—$CH_2$—$O)_{n2}$—$(CH_2)_{n3}$—, wherein each n1 and n3 is independently an integer selected from 0 to 3 and each n2 is independently an integer selected from 1 to 10.

In certain embodiments of a compound of Formula (II), each $X^1$ is selected from $C_{1-20}$ alkanediyl, $C_{1-20}$ cycloalkanediyl, $C_{6-10}$ arenediyl, and $C_{7-20}$ alkanearenediyl. In certain embodiments of a compound of Formula (II), each $X^3$ is selected from $C_{1-20}$ alkanediyl, $C_{1-20}$ cycloalkanediyl, $C_{6-10}$ arenediyl, and $C_{7-20}$ alkanearenediyl.

In certain embodiments of a compound of Formula (II), each $X^1$ is a covalent bond.

In certain embodiments of a compound of Formula (II), each $X^3$ is a covalent bond.

In certain embodiments of a compound of Formula (II), each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3 and each n2 is independently an integer selected from 1 to 20.

In certain embodiments of a compound of Formula (II), each $X^1$ and $X^3$ is independently selected from a covalent bond, methane-diyl, ethane-1,2-diyl, propane-1,3-diyl, pentane-1,5-diyl, 4-methylcyclohexane-diyl, benzene-1,2-diyl, benzene-1,3-diyl, and benzene-1,4-diyl.

In certain embodiments of a compound of Formula (II), each $X^1$ is a covalent bond; and each $X^3$ is selected from a covalent bond, methane-diyl, ethane-1,2-diyl, propane-1,3-diyl, pentane-1,5-diyl, 4-methylcyclohexane-diyl, benzene-1,2-diyl, benzene-1,3-diyl, and benzene-1,4-diyl.

In certain embodiments of a compound of Formula (II), each $X^1$ is ethane-1,2-diyl; and each $X^3$ is selected from a covalent bond, methane-diyl, ethane-1,2-diyl, propane-1,3-diyl, pentane-1,5-diyl, 4-methylcyclohexane-diyl, benzene-1,2-diyl, benzene-1,3-diyl, and benzene-1,4-diyl.

In certain embodiments of a compound of Formula (II), each $X^1$ is pentane-1,5-diyl; and each $X^3$ is selected from a covalent bond, methane-diyl, ethane-1,2-diyl, propane-1,3-diyl, pentane-1,5-diyl, 4-methylcyclohexane-diyl, benzene-1,2-diyl, benzene-1,3-diyl, and benzene-1,4-diyl.

In certain embodiments of a compound of Formula (II), each $X^1$ is 4-methylcyclohexane-diyl; and $X^3$ is selected from a covalent bond, methane-diyl, ethane-1,2-diyl, propane-1,3-diyl, pentane-1,5-diyl, 4-methylcyclohexane-diyl, benzene-1,2-diyl, benzene-1,3-diyl, and benzene-1,4-diyl.

In certain embodiments of a compound of Formula (II) wherein each $X^1$ and/or $X^3$ is —$(CH_2)_{n1}$—$(CH_2$—$CH_2$—$O)_{n2}$—$(CH_2)_{n3}$—, each n1 and n3 is independently an integer selected from 0 to 5, an integer selected from 0 to 4, an integer selected from 0 to 3, and in certain embodiments, an integer selected from 0 to 2. In certain embodiments of a compound of Formula (II) wherein each $X^1$ and/or $X^3$ is —$(CH_2)_{n1}$—$(CH_2$—$CH_2$—$O)_{n2}$—$(CH_2)_{n3}$—, each n2 is independently an integer selected from 1 to 25, an integer selected from 1 to 20, an integer selected from 1 to 15, an integer selected from 1 to 10, an integer selected from 1 to 5, an integer selected from 1 to 4, and in certain embodiments, an integer selected from 1 to 3.

In certain embodiments of a compound of Formula (II), each n1 and n3 is independently an integer selected from 0 to 5, in certain embodiments, an integer selected from 0 to 4, and in certain embodiments, an integer selected from 0 to 3; and each n2 is independently an integer selected from 1 to 25, in certain embodiments an integer selected from 1 to 20, in certain embodiments an integer selected from 1 to 15, in certain embodiments an integer selected from 1 to 10, and in certain embodiments an integer selected from 1 to 5.

In certain embodiments of a compound of Formula (II), each $X^2$ is selected from a covalent bond, —O—, —S—, —N—, —N═, —N═N—, —N═C—, —SO—, —SO$_2$—, —SO$_2$N—, —SS—, —C(O)—, —C(O)O—, —C(O)N—, —C(O)S—, —C(O)N—N═, —OP(O)(OH)O—, —OC(O) O—, —OC(O)N—, —NC(O)N—, and —NC(S)N. In certain embodiments of a compound of Formula (II), each $X^2$ is selected from a covalent bond, —O—, —S—, —SO—, —SO$_2$—, —SO$_2$N—, —SS—, —C(O)—, —C(O)O—, —C(O)N—, —C(O)N—N═, —OC(O)N—, and —NC(O) N—. In certain embodiments of a compound of Formula (II), each $X^2$ is selected from a covalent bond, —SO$_2$—, —SO$_2$N—, and —C(O)N—.

In certain embodiments of a compound of Formula (II), each $R^1$ and $R^2$ is independently selected from hydrogen, $C_{1-6}$ alkyl, substituted $C_{1-6}$ alkyl, $C_{1-6}$ heteroalkyl, substituted $C_{1-6}$ heteroalkyl, $C_{6-10}$ aryl, substituted $C_{6-10}$ aryl, $C_{6-10}$ heteroaryl, and substituted $C_{6-10}$ heteroaryl.

In certain embodiments of a compound of Formula (II), each $R^1$ and $R^2$ is independently selected from hydrogen, $C_{1-6}$ alkyl, substituted $C_{1-6}$ alkyl, and $C_{6-10}$ aryl. In certain embodiments of a compound of Formula (II), $R^1$ and $R^2$ are independently selected from hydrogen, methyl, ethyl, propyl, isopropyl, and phenyl. In certain embodiments of a compound of Formula (II), each $R^1$ and $R^2$ is independently selected from hydrogen and methyl. In certain embodiments of a compound of Formula (II), each $R^1$ and $R^2$ is independently selected from hydrogen and ethyl. In certain embodiments of a compound of Formula (II), each $R^1$ and $R^2$ is independently selected from hydrogen and propyl. In certain embodiments of a compound of Formula (II), each $R^1$ and $R^2$ is independently selected from hydrogen and isopropyl. In certain embodiments of a compound of Formula (II), each $R^1$ and $R^2$ is independently selected from hydrogen and phenyl.

In certain embodiments of a compound of Formula (II), each $R^1$ and $R^2$ is hydrogen. In certain embodiments of a compound of Formula (II), each $R^1$ is hydrogen and each $R^2$ is methyl. In certain embodiments of a compound of Formula (II), each $R^1$ is hydrogen and each $R^2$ is ethyl. In certain embodiments of a compound of Formula (II), each $R^1$ is hydrogen and each $R^2$ is propyl. In certain embodiments of a compound of Formula (II), each $R^1$ is hydrogen and each $R^2$ is isopropyl. In certain embodiments of a compound of Formula (II), each $R^1$ is hydrogen and each $R^2$ is phenyl.

In certain embodiments of a compound of Formula (II), D is selected from a therapeutic agent having at least one primary amine group, a therapeutic agent having at least one secondary amine group, a therapeutic agent having at least one hydroxy group, and a therapeutic agent having at least one thiol group.

In certain embodiments of a compound of Formula (II), D is selected from a folic acid analog, a purine analog, a pyrimidine analog, an anthracycline derivative, a dolastatin derivative, a camptotheca derivative, an ectainascidin derivative, a colchicine derivative, a duocarmycin derivative, an enediyne derivative, an epothilone derivative, a halichondrin derivative, a kahalalide derivative, a *streptomyces*, a tubulysin derivative, a vinca alkaloid, an antifolate, a hemiasterlin, a cathepsin K inhibitor, dipeptidyl peptidase IV inhibitor, heat shock protein 90 (Hsp90) inhibitor, a histone deacetylase inhibitor, an immunomodulator, an aurora kinase inhibitor, a cyclin-dependent kinase inhibitor, tyrosine kinase inhibitor, kinesin-related motor protein Eg5 inhibitor, kinesin spindle protein inhibitor, microtubule interference compounds, topoisomerase inhibitor, and an antibiotic.

In certain embodiments of a compound of Formula (II), D is selected from aminopterin, folitixorin, methotrexate, pemetrexed, pralatrexate, raltitrexed, pelitrexol, talotrexin, deoxycoformycin, cladribine, clofarabine, fludarabine, thioguanine, mercaptopurine, berubicin, daunorubicin, doxorubicin, epirubicin, idarubicin, amrubicin, pirarubicin, zorubicin, mitoxantrone, banoxantrone, ledoxantrone, nortopixantrone, pixantrone, piroxantrone, sabarubicin, topixantrone, monomethyl auristatin E, monomethyl auristatin F, monomethyl dolastatin 10, dolastatin 15, belotecan, atiratecan, camptothecin, exatecan, irinotecan, namitecan, rubitecan, topotecan, demecolcine, duocarmycin A, duocarmycin SA, duocarmycin B, duocarmycin B1, abbeymycin, anthramycin, centanamycin, chicamycin, mazethramycin, porothramycin A, porothramycin B, sibanomycin, sibiromycin, trabectedin, calicheamicin γ1, calicheamicin T, esperamicin A1, esperamicin C, esperamicin D, dynemicin A, dynemicin H, dynemicin M, dynemicin N, dynemicin O, dynemicin P, dynemicin Q, dynemicin S, neocarzinostatin chromophore, uncialamycin, 21-aminoepothilone B, eribulin, hemiasterlin, HTI-286, kahalatide F, elsamitrucin, lucanthone, melphalan, mitoguazone, nimustine, procarbazine, dacarbazine, amsacrine, 5-amino-4-oxo-pentanoic acid, methyl 5-amino-4-oxo-pentanoate, actinomycin D, 7-aminoactinomycin D, bleomycin, mitomycin, staurosporine, desacetylvinblastine hydrazide, vinblastine, vincristine, vindestine, vinflunine, vinorelbine, afatinib, apilimod, balamapimod, barasertib, bosutinib, canertinib, cevipabulin, crizotinib, dacomitinib, dasatinib, denibulin, dilmapimod, dinaciclib, dovitinib, dutacatib, duvoglustat, edotecarin, elisidepsin, entinostat, epetirimod, erlotinib, fingolimod, fostamatinib, gefitinib, golotimod, gusperimus, imatinib, imiquimod, intedanib, ispinesib, lapatinib, lenalidomide, linifanib, litronesib, losmapimod, metesind, mocetinostat, motesanib, masitinib, myriocin, neratinib, nilotinib, odanacatib, ombrabulin, pamapimod, panobinostat, pazopanib, plerixafor, pomalidomide, razupenem, resiquimod, sabarubicin, saracatinib, seliciclib, selumetinib, sotirimod, squalamine, tacedinaline, talabostat, taltobulin, telatinib, tipifarnib, tozasertib, vandetanib, vatalanib, veliparib, voreloxin, alvespimycin, amikacin, amphotericin B, arbekacin, astromicin, bacitracin, balofloxacin, bederocin, bekanamycin, besifloxacin, brodimoprim, ciprofloxacin, clinafloxacin, colistin, daptomycin, dibekacin, enoxacin, framycetin, garenoxacin, gatifloxacin, gemifloxacin, gentamicin, gentamicin, grepafloxacin, hamycin, hexetidine, hygromycin B, ibacitabine, iclaprim, isepamicin, kanamycin, lomefloxacin, lucimycin, lymecycline, mepartricin, moxifloxacin, natamycin, nemonoxacin, neomycin B, neomycin C, netilmicin, norfloxacin, nystatin, omadacycline, oritavancin, paromomycin, pazufloxacin, perimycin A, perimycin B, perimycin C, pipemidic acid, polymyxin B, puromycin, radezolid, retaspimycin, ribostamycin, rimocidin, sisomicin, sitafloxacin, sparfloxacin, spectinomycin, streptomycin, sulfacetamide, sulfadiazine, sulfadimethoxine, sulfadimidine, sulfafurazole, sulfalene, sulfamazone, sulfamerazine, sulfamethizole, sulfamethoxazole, sulfamethoxypyridazine, sulfametomidine, sulfametoxydiazine, sulfametrole, sulfamoxole, sulfanilamide, sulfaperin, sulfaphenazole, sulfapyridine, sulfathiazole, sulfathiourea, sulfisomidine, teicoplanin, telavancin, tanespimycin, temafloxacin, tetroxoprim, tigecycline, tobramycin, tosufloxacin, trimethoprim, trimethoprim, trovafloxacin, tyrothricin, ulifloxacin, valnemulin, vancomycin, verdamicin, and zabofloxacin.

In certain embodiments of a compound of Formula (II), n5 is an integer selected from 1 to 20, from 1 to 5, and in certain embodiments, n5 is an integer selected from 1 to 3. In certain embodiments, n5 is 1, n5 is 2, n5 is 3, and in certain embodiments, n5 is 4. In certain embodiments of a compound of Formula (II), n5 is selected from 1, 2, 3, and 4.

In certain embodiments of a compound of Formula (II), each $A^1$ is a moiety of Formula ($A^1$a1), wherein each $R^8$ and $R^9$ is independently selected from hydrogen, $C_{1-4}$ alkyl, and $C_{6-10}$ aryl; each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 5, and each n2 is independently an integer selected from 1 to 25; each $X^2$ is independently selected from a covalent bond, —O—, —S—, —SO—, —SO$_2$—, —SO$_2$N—, —SS—, —C(O)—, —C(O)O—, —C(O)N—, —C(O)N—N=, —OC(O)N—, and —NC(O)N—; each $R^1$ and $R^2$ is independently selected from hydrogen, $C_{1-4}$ alkyl, and $C_{6-8}$ aryl; D is selected from a therapeutic agent having at least one primary amine group, a therapeutic agent having at least one secondary amine group, a therapeutic agent having at least one hydroxy group, and a therapeutic agent having at least one thiol group; and n5 is selected from 1 to 20.

In certain embodiments of a compound of Formula (II), each $A^1$ is a moiety of Formula ($A^1$a1), wherein each $R^8$ and $R^9$ is independently selected from hydrogen and methyl; each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; each $X^2$ is selected from a covalent bond, —O—, —SO$_2$—, —SO$_2$N—, —C(O)—, —C(O)O—, and —C(O)N—; each $R^1$ and $R^2$ is independently selected from hydrogen, $C_{1-4}$ alkyl, and $C_{6-8}$ aryl; D is selected from a therapeutic agent having at least one primary amine group and a therapeutic agent having at least one secondary amine group; and n5 is selected from 1 to 5.

In certain embodiments of a compound of Formula (II), each $A^1$ is a moiety of Formula ($A^1$a1), wherein each $R^8$ and $R^9$ is hydrogen; each $X^1$ is pentane-1,5-diyl; each $X^2$ is a covalent bond; each $X^3$ is a covalent bond; each $R^1$ and $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$a1), wherein each $R^8$ and $R^9$ is hydrogen; each $X^1$ is benzene-1,3-diyl; each $X^2$ is a covalent bond; each $X^3$ is a covalent bond; each $R^1$ and $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$a1), wherein each $R^8$ and $R^9$ is hydrogen; each $X^1$ is 4-methylcyclohexane-diyl; each $X^2$ is a covalent bond; each $X^3$ is a covalent bond; each $R^1$ and $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$a1), wherein each $R^8$ and $R^9$ is hydrogen; each $X^1$ is pentane-1,5-diyl; each $X^2$ is a covalent bond; each $X^3$ is a covalent bond; each $R^1$ is hydrogen; each $R^2$ is methyl; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$a1), wherein each $R^8$ and $R^9$ is hydrogen; each $X^1$ is pentane-1,5-diyl; each $X^2$ is a covalent bond; each $X^3$ is a covalent bond; each $R^1$ and $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$a1), wherein each $R^8$ and $R^9$ is hydrogen; each $X^1$ is benzene-1,4-diyl; each $X^2$ is a covalent bond; each $X^3$ is propane-1,3-diyl; each $R^1$ and $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$a1), wherein each $R^8$ and $R^9$ is hydrogen; each $X^1$ is —$(CH_2)_{n1}$—$(CH_2$—$CH_2$—$O)_{n2}$—$(CH_2)_{n3}$—, wherein n1 is 0, n2 is 2, and n3 is 2; each $X^2$ is a covalent bond; each $X^3$ is a covalent bond; each $R^1$ and $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$a1), wherein each $R^8$ and $R^9$ is hydrogen; each $X^1$ is pentane-1,5-diyl; each $X^2$ is —C(O)N—; each $X^3$ is pentane-1,5-diyl; each $R^1$ is hydrogen; each $R^2$ is methyl; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$a1), wherein each $R^8$ and $R^9$ is hydrogen; each $X^1$ is 4-methylcyclohexane-diyl; each $X^2$ is —C(O)N—; each $X^3$ is pentane-1,5-diyl; each $R^1$ is hydrogen; each $R^2$ is methyl; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$a2), wherein each $R^8$ is selected from hydrogen, $C_{1-4}$ alkyl, and $C_{6-10}$ aryl; each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 5, and each n2 is independently an integer selected from 1 to 25; each $X^2$ is selected from a covalent bond, —O—, —S—, —SO—, —SO$_2$—, —SO$_2$N—, —SS—, —C(O)—, —C(O)O—, —C(O)N—, —C(O)N—N═, —OC(O)N—, and —NC(O)N—; each $R^1$ and $R^2$ is independently selected from hydrogen, $C_{1-4}$ alkyl, and $C_{6-8}$ aryl; D is selected from a therapeutic agent having at least one primary amine group, a therapeutic agent having at least one secondary amine group, a therapeutic agent having at least one hydroxy group, and a therapeutic agent having at least one thiol group; and n5 is selected from 1 to 20.

In certain embodiments of a compound of Formula (II), each $A^1$ is a moiety of Formula ($A^1a2$), each wherein $R^8$ is selected from hydrogen and methyl; each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene -diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; each $X^2$ is selected from a covalent bond, —O—, —$SO_2$—, —$SO_2N$—, —C(O)—, —C(O)O—, and —C(O)N—; each $R^1$ and $R^2$ is independently selected from hydrogen, $C_{1-4}$ alkyl, and $C_{6-8}$ aryl; D is selected from a therapeutic agent having at least one primary amine group and a therapeutic agent having at least one secondary amine group; and n5 is selected from 1 to 5.

In certain embodiments of a compound of Formula (II), each $A^1$ is a moiety of Formula ($A^1a2$), wherein each $R^8$ is hydrogen; each $X^1$ is a covalent bond; each $X^2$ is a covalent bond; each $X^3$ is a covalent bond; each $R^1$ and $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1a2$), wherein each $R^8$ is methyl; each $X^1$ is a covalent bond; each $X^2$ is a covalent bond; each $X^3$ is a covalent bond; each $R^1$ and $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1a2$), wherein each $R^8$ is hydrogen; each $X^1$ is a covalent bond; each $X^2$ is —$SO_2$—; each $X^3$ is methane-diyl; each $R^1$ and $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1a2$), wherein each $R^8$ is hydrogen; each $X^1$ is a covalent bond; each $X^2$ is —$SO_2$—; each $X^3$ is ethane-1,2-diyl; each $R^1$ and $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1a2$), wherein each $R^8$ is hydrogen; each $X^1$ is a covalent bond; each $X^2$ is —$SO_2N$—; each $X^3$ is pentane-1,5-diyl; each $R^1$ and $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1a2$), wherein each $R^8$ is methyl; each $X^1$ is a covalent bond; each $X^2$ is —C(O)N—; each $X^3$ is pentane-1,5-diyl; each $R^1$ and $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1a2$), wherein each $R^8$ is methyl; each $X^1$ is a covalent bond; each $X^2$ is —C(O)N—; each $X^3$ is 4-methylcyclohexane-diyl; each $R^1$ and $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1a2$), wherein each $R^8$ is methyl; each $X^1$ is a covalent bond; each $X^2$ is —C(O)N—; each $X^3$ is pentane-1,5-diyl; each $R^1$ is hydrogen; each $R^2$ is methyl; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1a2$), wherein each $R^8$ is methyl; each $X^1$ is a covalent bond; each $X^2$ is —C(O)N—; each $X^3$ is 4-methylcyclohexane-diyl; each $R^1$ is hydrogen; each $R^2$ is methyl; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1a2$), wherein each $R^8$ is methyl; each $X^1$ is a covalent bond; each $X^2$ is —C(O)O—; each $X^3$ is pentane-1,5-diyl; each $R^1$ and $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of ($A^1a3$), wherein each E is selected from F, Cl, Br, and I; each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 5, and each n2 is independently an integer selected from 1 to 25; each $X^2$ is selected from a covalent bond, —O—, —S—, —SO—, —$SO_2$—, —$SO_2N$—, —SS—, —C(O)—, —C(O)O—, —C(O)N—, —C(O)N—N═, —OC(O)N—, and —NC(O)N—; each $R^1$ and $R^2$ is independently selected from hydrogen, $C_{1-4}$ alkyl, and $C_{6-8}$ aryl; D is selected from a therapeutic agent having at least one primary amine group, a therapeutic agent having at least one secondary amine group, a therapeutic agent having at least one hydroxy group, and a therapeutic agent having at least one thiol group; and n5 is selected from 1 to 20.

In certain embodiments of a compound of Formula (II), each $A^1$ is a moiety of ($A^1a3$), wherein each E is selected from F, Cl, Br, and I; each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; each $X^2$ is selected from a covalent bond, —O—, —SO$_2$—, —SO$_2$N—, —C(O)—, —C(O)O—, and —C(O)N—; each R$^1$ and R$^2$ is independently selected from hydrogen, C$_{1-4}$ alkyl, and C$_{6-8}$ aryl; D is selected from a therapeutic agent having at least one primary amine group and a therapeutic agent having at least one secondary amine group; and n5 is selected from 1 to 5.

In certain embodiments of a compound of Formula (II), each A$^1$ is a moiety of Formula (A$^1$a3), wherein each E is Br; each X$^1$ is a covalent bond; each X$^2$ is a covalent bond; each X$^3$ is a covalent bond; each R$^1$ is hydrogen; each R$^2$ is methyl; D is selected from a therapeutic agent having at least one primary amine group and a therapeutic agent having at least one secondary amine group; and n5 is selected from 1 to 4.

In certain embodiments of a compound of Formula (II), each A$^1$ is a moiety of Formula (A$^1$a3), wherein each E is Br; each X$^1$ is a covalent bond; each X$^2$ is —C(O)N—; each X$^3$ is pentane-1,5-diyl; each R$^1$ is hydrogen; each R$^2$ is methyl; D is selected from a therapeutic agent having at least one primary amine group and a therapeutic agent having at least one secondary amine group; and n5 is selected from 1 to 4.

In certain embodiments of a compound of Formula (II), each A$^1$ is a moiety of Formula (A$^1$a3), wherein each E is Br; each X$^1$ is a covalent bond; each X$^2$ is —C(O)N—; each X$^3$ is 4-methylcyclohexane-diyl; each R$^1$ is hydrogen; each R$^2$ is methyl; D is selected from a therapeutic agent having at least one primary amine group and a therapeutic agent having at least one secondary amine group; and n5 is selected from 1 to 4.

In certain embodiments of a compound of Formula (II), each A$^1$ is a moiety of Formula (A$^1$a3), wherein each E is Br; each X$^1$ is a covalent bond; each X$^2$ is —C(O)O—; each X$^3$ is pentane-1,5-diyl; each R$^1$ is hydrogen; each R$^2$ is methyl; D is selected from a therapeutic agent having at least one primary amine group and a therapeutic agent having at least one secondary amine group; and n5 is selected from 1 to 4.

In certain embodiments of a compound of Formula (II), each A$^1$ is a moiety of (A$^1$b1), wherein each L$^2$ is selected from halogen, N-hydroxysuccinimidyl, substituted N-hydroxysuccinimidyl, phenol-yl, and substituted phenol-yl; each X$^1$ and X$^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 5, and each n2 is independently an integer selected from 1 to 25; each X$^2$ is selected from a covalent bond, —O—, —S—, —SO—, —SO$_2$—, —SO$_2$N—, —SS—, —C(O)—, —C(O)O—, —C(O)N—, —C(O)N—N═, —OC(O)N—, and —NC(O)N—; each R$^1$ and R$^2$ is independently selected from hydrogen, C$_{1-4}$ alkyl, and C$_{6-8}$ aryl; D is selected from a therapeutic agent having at least one primary amine group, a therapeutic agent having at least one secondary amine group, a therapeutic agent having at least one hydroxy group, and a therapeutic agent having at least one thiol group; and n5 is selected from 1 to 20.

In certain embodiments of a compound of Formula (II), each A$^1$ is a moiety of (A$^1$b1), wherein each L$^2$ is selected from halogen, N-hydroxysuccinimidyl, substituted N-hydroxysuccinimidyl, phenol-yl, and substituted phenol-yl; each X$^1$ and X$^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each X$^2$ is selected from a covalent bond, —O—, —SO$_2$—, —SO$_2$N—, —C(O)—, —C(O)O—, and —C(O)N—; each R$^1$ and R$^2$ is independently selected from hydrogen, C$_{1-4}$ alkyl, and C$_{6-8}$ aryl; D is selected from a therapeutic agent having at least one primary amine group and a therapeutic agent having at least one secondary amine group; and n5 is selected from 1 to 5.

In certain embodiments of a compound of Formula (II), each A$^1$ is a moiety of Formula (A$^1$b1), wherein each L$^2$ is N-hydroxysuccinimidyl; each X$^1$ is ethane-1,2-diyl; each X$^2$ is a covalent bond; each X$^3$ is a covalent bond; each R$^1$ and R$^2$ is hydrogen; D is selected from a therapeutic agent having at least one primary amine group and a therapeutic agent having at least one secondary amine group; and n5 is selected from 1 to 4.

In certain embodiments of a compound of Formula (II), each A$^1$ is a moiety of (A$^1$b2), wherein each L$^2$ is selected from halogen, N-hydroxysuccinimidyl, substituted N-hydroxysuccinimidyl, phenol-yl, and substituted phenol-yl, and each R$^8$ and R$^9$ is independently selected from hydrogen, C$_{1-4}$ alkyl, and C$_{6-10}$ aryl; each X$^1$ and X$^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 5, and each n2 is independently an integer selected from 1 to 25; each X$^2$ is selected from a covalent bond, —O—, —S—, —SO—, —SO$_2$—, —SO$_2$N—, —SS—, —C(O)—, —C(O)O—, —C(O)N—, —C(O)N—N═, —OC(O)N—, and —NC(O)N—; each R$^1$ and R$^2$ is independently selected from hydrogen, C$_{1-4}$ alkyl, and C$_{6-8}$ aryl; D is selected from a therapeutic agent having at least one primary amine group, a therapeutic agent having at least one secondary amine group, a therapeutic agent having at least one hydroxy group, and a therapeutic agent having at least one thiol group; and n5 is selected from 1 to 20.

In certain embodiments of a compound of Formula (II), each A$^1$ is a moiety of (A$^1$b2), wherein each L$^2$ is selected from halogen, N-hydroxysuccinimidyl, substituted N-hydroxysuccinimidyl, phenol-yl, and substituted phenol-yl, and each R$^8$ and R$^9$ is independently selected from hydrogen, C$_{1-4}$ alkyl, and C$_{6-10}$ aryl; each X$^1$ and X$^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each X$^2$ is selected from a covalent bond, —O—, —SO$_2$—, —SO$_2$N—, —C(O)—, —C(O)O—, and —C(O)N—; each R$^1$ and R$^2$ is independently selected from hydrogen, C$_{1-4}$ alkyl, and C$_{6-8}$ aryl; D is selected from a therapeutic agent having at least one primary amine group and a therapeutic agent having at least one secondary amine group; and n5 is selected from 1 to 5.

In certain embodiments of a compound of Formula (II), each $A^1$ is a moiety of Formula ($A^1b2$), wherein each $L^2$ is N-hydroxysuccinimidyl, and each $R^8$ and $R^9$ is hydrogen; each $X^1$ is ethane-1,2-diyl; each $X^2$ is a covalent bond; each $X^3$ is a covalent bond; each $R^1$ and $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of ($A^1c1$); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2—CH_2—O)_{n2}$—$(CH_2)_{n3}$—, wherein each n1 and n3 is independently an integer selected from 0 to 5, and each n2 is independently an integer selected from 1 to 25; each $X^2$ is selected from a covalent bond, —O—, —S—, —SO—, —$SO_2$—, —$SO_2N$—, —SS—, —C(O)—, —C(O)O—, —C(O)N—, —C(O)N—N=, —OC(O)N—, and —NC(O)N—; each $R^1$ and $R^2$ is independently selected from hydrogen, $C_{1-4}$ alkyl, and $C_{6-8}$ aryl; D is selected from a therapeutic agent having at least one primary amine group, a therapeutic agent having at least one secondary amine group, a therapeutic agent having at least one hydroxy group, and a therapeutic agent having at least one thiol group; and n5 is selected from 1 to 20.

In certain embodiments of a compound of Formula (II), each $A^1$ is a moiety of ($A^1c1$); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2—CH_2—O)_{n2}$—$(CH_2)_{n3}$—, wherein each n1 and n3 is independently an integer selected from 0 to 3, and each n2 is independently an integer selected from 1 to 20; each $X^2$ is selected from a covalent bond, —O—, —$SO_2$—, —$SO_2N$—, —C(O)—, —C(O)O—, and —C(O)N—; each $R^1$ and $R^2$ is independently selected from hydrogen, $C_{1-4}$ alkyl, and $C_{6-8}$ aryl; D is selected from a therapeutic agent having at least one primary amine group and a therapeutic agent having at least one secondary amine group; and n5 is selected from 1 to 5.

In certain embodiments of a compound of Formula (II), each $A^1$ is a moiety of Formula ($A^1c1$); each $X^1$ is butane-1,4-diyl; each $X^2$ is a covalent bond; each $X^3$ is a covalent bond; each $R^1$ is hydrogen; each $R^2$ is methyl; D is selected from a therapeutic agent having at least one primary amine group and a therapeutic agent having at least one secondary amine group; and n5 is selected from 1 to 5.

In certain embodiments of a compound of Formula (II), each $A^1$ is a moiety of Formula ($A^1c1$); each $X^1$ is butane-1,4-diyl; each $X^2$ is —C(O)N—; each $X^3$ is pentane-1,5-diyl; each $R^1$ and $R^2$ is hydrogen; D is selected from a therapeutic agent having at least one primary amine group and a therapeutic agent having at least one secondary amine group; and n5 is selected from 1 to 5.

In certain embodiments of a compound of Formula (II), each $A^1$ is a moiety of ($A^1c2$); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2—CH_2—O)_{n2}$—$(CH_2)_{n3}$—, wherein each n1 and n3 is independently an integer selected from 0 to 5, and each n2 is independently an integer selected from 1 to 25; each $X^2$ is selected from a covalent bond, —O—, —S—, —SO—, —$SO_2$—, —$SO_2N$—, —SS—, —C(O)—, —C(O)O—, —C(O)N—, —C(O)N—N=, —OC(O)N—, and —NC(O)N—; each $R^1$ and $R^2$ is independently selected from hydrogen, $C_{1-4}$ alkyl, and $C_{6-8}$ aryl; D is selected from a therapeutic agent having at least one primary amine group, a therapeutic agent having at least one secondary amine group, a therapeutic agent having at least one hydroxy group, and a therapeutic agent having at least one thiol group; and n5 is selected from 1 to 20.

In certain embodiments of a compound of Formula (II), each $A^1$ is a moiety of ($A^1c2$); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2—CH_2—O)_{n2}$—$(CH_2)_{n3}$—, wherein each n1 and n3 is independently an integer selected from 0 to 3, and each n2 is independently an integer selected from 1 to 20; each $X^2$ is selected from a covalent bond, —O—, —$SO_2$—, —$SO_2N$—, —C(O)—, —C(O)O—, and —C(O)N—; each $R^1$ and $R^2$ is independently selected from hydrogen, $C_{1-4}$ alkyl, and $C_{6-8}$ aryl; D is selected from a therapeutic agent having at least one primary amine group and a therapeutic agent having at least one secondary amine group; and n5 is selected from 1 to 5.

In certain embodiments of a compound of Formula (II), each $A^1$ is a moiety of Formula ($A^1c2$); each $X^1$ is butane-1,4-diyl; each $X^2$ is a covalent bond; each $X^3$ is a covalent bond; each $R^1$ is hydrogen; each $R^2$ is methyl; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1c2$); each $X^1$ is butane-1,4-diyl; each $X^2$ is —C(O)N—; each $X^3$ is pentane-1,5-diyl; each $R^1$ is hydrogen; each $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1c2$); each $X^1$ is butane-1,4-diyl; each $X^2$ is —C(O)N—; each $X^3$ is 4-methylcyclohexane-diyl; each $R^1$ is hydrogen; each $R^2$ is methyl; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of ($A^1c3$); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2—CH_2—O)_{n2}$—$(CH_2)_{n3}$—, wherein each n1 and n3 is independently an integer selected from 0 to 5, and each n2 is independently an integer selected from 1 to 25; each $X^2$ is selected from a covalent bond, —O—, —S—, —SO—, —$SO_2$—, —$SO_2N$—, —SS—, —C(O)—, —C(O)

O—, —C(O)N—, —C(O)N—N=, —OC(O)N—, and —NC(O)N—; each $R^1$ and $R^2$ is independently selected from hydrogen, $C_{1-4}$ alkyl, and $C_{6-8}$ aryl; D is selected from a therapeutic agent having at least one primary amine group, a therapeutic agent having at least one secondary amine group, a therapeutic agent having at least one hydroxy group, and a therapeutic agent having at least one thiol group; and n5 is selected from 1 to 20.

In certain embodiments of a compound of Formula (II), each $A^1$ is a moiety of ($A^1$c3); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each $X^2$ is selected from a covalent bond, —O—, —SO$_2$—, —SO$_2$N—, —C(O)—, —C(O)O—, and —C(O)N—; each $R^1$ and $R^2$ is independently selected from hydrogen, $C_{1-4}$ alkyl, and $C_{6-8}$ aryl; D is selected from a therapeutic agent having at least one primary amine group and a therapeutic agent having at least one secondary amine group; and n5 is selected from 1 to 5.

In certain embodiments of a compound of Formula (II), each $A^1$ is a moiety of Formula ($A^1$c3); each $X^1$ is butane-1,4-diyl; each $X^2$ is a covalent bond; each $X^3$ is a covalent bond; each $R^1$ is hydrogen; each $R^2$ is methyl; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$c3); each $X^1$ is butane-1,4-diyl; each $X^2$ is —C(O)N—; each $X^3$ is pentane-1,5-diyl; each $R^1$ is hydrogen; each $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$c3); each $X^1$ is butane-1,4-diyl; each $X^2$ is —C(O)N—; each $X^3$ is 4-methylcyclohexane-diyl; each $R^1$ is hydrogen; each $R^2$ is methyl; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of ($A^1$d1); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 5, and each n2 is independently an integer selected from 1 to 25; each $X^2$ is selected from a covalent bond, —O—, —S—, —SO—, —SO$_2$—, —SO$_2$N—, —SS—, —C(O)—, —C(O)O—, —C(O)N—, —C(O)N—N=, —OC(O)N—, and —NC(O)N—; each $R^1$ and $R^2$ is independently selected from hydrogen, $C_{1-4}$ alkyl, and $C_{6-8}$ aryl; D is selected from a therapeutic agent having at least one primary amine group, a therapeutic agent having at least one secondary amine group, a therapeutic agent having at least one hydroxy group, and a therapeutic agent having at least one thiol group; and n5 is selected from 1 to 20.

In certain embodiments of a compound of Formula (II), each $A^1$ is a moiety of ($A^1$d1); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each $X^2$ is selected from a covalent bond, —O—, —SO$_2$—, —SO$_2$N—, —C(O)—, —C(O)O—, and —C(O)N—; each $R^1$ and $R^2$ is independently selected from hydrogen, $C_{1-4}$ alkyl, and $C_{6-8}$ aryl; D is selected from a therapeutic agent having at least one primary amine group and a therapeutic agent having at least one secondary amine group; and n5 is selected from 1 to 5.

In certain embodiments of a compound of Formula (II), each $A^1$ is a moiety of Formula ($A^1$d1); each $X^1$ is propane-1,3-diyl; each $X^2$ is a covalent bond; each $X^3$ is a covalent bond; each $R^1$ is hydrogen; each $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$d1); each $X^1$ is propane-1,3-diyl; each $X^2$ is —C(O)N—; each $X^3$ is pentane-1,5-diyl; each $R^1$ is hydrogen; each $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$d1); each $X^1$ is propane-1,3-diyl; each $X^2$ is —C(O)N—; each $X^3$ is 4-methylcyclohexane-diyl; each $R^1$ is hydrogen; each $R^2$ is methyl; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of ($A^1$d2); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 5, and each n2 is independently an integer selected from 1 to 25; each $X^2$ is selected from a covalent bond, —O—, —S—, —SO—, —SO$_2$—, —SO$_2$N—, —SS—, —C(O)—, —C(O)O—, —C(O)N—, —C(O)N—N=, —OC(O)N—, and —NC(O)N—; each $R^1$ and $R^2$ is independently selected from hydrogen, $C_{1-4}$ alkyl, and $C_{6-8}$ aryl; D is selected from a therapeutic agent having at least one primary amine group, a therapeutic agent having at least one secondary amine group, a therapeutic agent having at least one hydroxy group, and a therapeutic agent having at least one thiol group; and n5 is selected from 1 to 20.

In certain embodiments of a compound of Formula (II), each $A^1$ is a moiety of ($A^1$d2); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; each $X^2$ is selected from a covalent bond, —O—, —$SO_2$—, —$SO_2N$—, —C(O)—, —C(O)O—, and —C(O)N—; each $R^1$ and $R^2$ is independently selected from hydrogen, $C_{1-4}$ alkyl, and $C_{6-8}$ aryl; D is selected from a therapeutic agent having at least one primary amine group and a therapeutic agent having at least one secondary amine group; and n5 is selected from 1 to 5.

In certain embodiments of a compound of Formula (II), each $A^1$ is a moiety of Formula ($A^1$d2); each $X^1$ is ethane-1,2-diyl; each $X^2$ is a covalent bond; each $X^3$ is a covalent bond; each $R^1$ is hydrogen; each $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$d2); each $X^1$ is ethane-1,2-diyl; each $X^2$ is —C(O)N—; each $X^3$ is pentane-1,5-diyl; each $R^1$ is hydrogen; each $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$d2); each $X^1$ is ethane-1,2-diyl; each $X^2$ is —C(O)N—; each $X^3$ is 4-methylcyclohexane-diyl; each $R^1$ is hydrogen; each $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$d3); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 5, and each n2 is independently an integer selected from 1 to 25; each $X^2$ is selected from a covalent bond, —O—, —S—, —SO—, —$SO_2$—, —$SO_2N$—, —SS—, —C(O)—, —C(O)O—, —C(O)N—, —C(O)N—N=, —OC(O)N—, and —NC(O)N—; each $R^1$ and $R^2$ is independently selected from hydrogen, $C_{1-4}$ alkyl, and $C_{6-8}$ aryl; D is selected from a therapeutic agent having at least one primary amine group, a therapeutic agent having at least one secondary amine group, a therapeutic agent having at least one hydroxy group, and a therapeutic agent having at least one thiol group; and n5 is selected from 1 to 20.

In certain embodiments of a compound of Formula (II), each $A^1$ is a moiety of ($A^1$d3); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; each $X^2$ is selected from a covalent bond, —O—, —$SO_2$—, —$SO_2N$—, —C(O)—, —C(O)O—, and —C(O)N—; each $R^1$ and $R^2$ is independently selected from hydrogen, $C_{1-4}$ alkyl, and $C_{6-8}$ aryl; D is selected from a therapeutic agent having at least one primary amine group and a therapeutic agent having at least one secondary amine group; and n5 is selected from 1 to 5.

In certain embodiments of a compound of Formula (II), each $A^1$ is a moiety of Formula ($A^1$d3); each $X^1$ is a covalent bond; each $X^2$ is a covalent bond; each $X^3$ is a covalent bond; each $R^1$ is hydrogen; each $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$d3); each $X^1$ is a covalent bond; each $X^2$ is —C(O)N—; each $X^3$ is pentane-1,5-diyl; each $R^1$ is hydrogen; each $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$d3); each $X^1$ is a covalent bond; each $X^2$ is —C(O)N—; each $X^3$ is 4-methylcyclohexane-diyl; each $R^1$ is hydrogen; each $R^2$ is methyl; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of ($A^1$e1); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 5, and each n2 is independently an integer selected from 1 to 25; each $X^2$ is selected from a covalent bond, —O—, —S—, —SO—, —$SO_2$—, —$SO_2N$—, —SS—, —C(O)—, —C(O)O—, —C(O)N—, —C(O)N—N=, —OC(O)N—, and —NC(O)N—; each $R^1$ and $R^2$ is independently selected from hydrogen, $C_{1-4}$ alkyl, and $C_{6-8}$ aryl; D is selected from a therapeutic agent having at least one primary amine group, a therapeutic agent having at least one secondary amine group, a therapeutic agent having at least one hydroxy group, and a therapeutic agent having at least one thiol group; and n5 is selected from 1 to 20.

In certain embodiments of a compound of Formula (II), each $A^1$ is a moiety of ($A^1$e1); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; each $X^2$ is selected from a covalent bond, —O—, —$SO_2$—, —$SO_2N$—, —C(O)—, —C(O)O—, and —C(O)N—; each $R^1$ and $R^2$ is independently selected from hydrogen, $C_{1-4}$ alkyl, and $C_{6-8}$ aryl; D is selected from a therapeutic agent having at least one primary amine group and a therapeutic agent having at least one secondary amine group; and n5 is selected from 1 to 5.

In certain embodiments of a compound of Formula (II), each $A^1$ is a moiety of Formula ($A^1$e1); each $X^1$ is pentane-1,5-diyl; each $X^2$ is a covalent bond; each $X^3$ is a covalent bond; each $R^1$ is hydrogen; each $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$e1); each $X^1$ is pentane-1,5-diyl; each $X^2$ is —C(O)N—; each $X^3$ is pentane-1,5-diyl; each $R^1$ is hydrogen; each $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$e1); each $X^1$ is pentane-1,5-diyl; each $X^2$ is —C(O)N—; each $X^3$ is 4-methylcyclohexane-diyl; each $R^1$ is hydrogen; each $R^2$ is methyl; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of ($A^1$f1); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 5, and each n2 is independently an integer selected from 1 to 25; each $X^2$ is selected from a covalent bond, —O—, —S—, —SO—, —SO$_2$—, —SO$_2$N—, —SS—, —C(O)—, —C(O)O—, —C(O)N—, —C(O)N—N=, —OC(O)N—, and —NC(O)N—; each $R^1$ and $R^2$ is independently selected from hydrogen, $C_{1-4}$ alkyl, and $C_{6-8}$ aryl; D is selected from a therapeutic agent having at least one primary amine group, a therapeutic agent having at least one secondary amine group, a therapeutic agent having at least one hydroxy group, and a therapeutic agent having at least one thiol group; and n5 is selected from 1 to 20.

In certain embodiments of a compound of Formula (II), each $A^1$ is a moiety of ($A^1$f1); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each $X^2$ is selected from a covalent bond, —O—, —SO$_2$—, —SO$_2$N—, —C(O)—, —C(O)O—, and —C(O)N—; each $R^1$ and $R^2$ is independently selected from hydrogen, $C_{1-4}$ alkyl, and $C_{6-8}$ aryl; D is selected from a therapeutic agent having at least one primary amine group and a therapeutic agent having at least one secondary amine group; and n5 is selected from 1 to 5.

In certain embodiments of a compound of Formula (II), each $A^1$ is a moiety of Formula ($A^1$f1); each $X^1$ is a covalent bond; each $X^2$ is a covalent bond; each $X^3$ is a covalent bond; each $R^1$ is hydrogen; each $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$f1); each $X^1$ is methane-diyl; each $X^2$ is a covalent bond; each $X^3$ is a covalent bond; each $R^1$ is hydrogen; each $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$f1); each $X^1$ is a covalent bond; each $X^2$ is —C(O)N—; each $X^3$ is pentane-1,5-diyl; each $R^1$ is hydrogen; each $R^2$ is methyl; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$f1); each $X^1$ is a covalent bond; each $X^2$ is —C(O)N—; each $X^3$ is 4-methylcyclohexane-diyl; each $R^1$ is hydrogen; each $R^2$ is methyl; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$f1); each $X^1$ is pentane-1,5-diyl; each $X^2$ is —C(O)N—; each $X^3$ is pentane-1,5-diyl; each $R^1$ is hydrogen; each $R^2$ is methyl; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of ($A^1$f2); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 5, and each n2 is independently an integer selected from 1 to 25; each $X^2$ is selected from a covalent bond, —O—, —S—, —SO—, —SO$_2$—, —SO$_2$N—, —SS—, —C(O)—, —C(O)O—, —C(O)N—, —C(O)N—N=, —OC(O)N—, and —NC(O)N—; each $R^1$ and $R^2$ is independently selected from hydrogen, $C_{1-4}$ alkyl, and $C_{6-8}$ aryl; D is selected from a therapeutic agent having at least one primary amine group, a therapeutic agent having at least one secondary amine group, a therapeutic agent having at least one hydroxy group, and a therapeutic agent having at least one thiol group; and n5 is selected from 1 to 20.

In certain embodiments of a compound of Formula (II), each $A^1$ is a moiety of ($A^1$f2); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each $X^2$ is selected from a covalent bond, —O—, —SO$_2$—, —SO$_2$N—, —C(O)—, —C(O)O—, and —C(O)N—; each $R^1$ and $R^2$ is independently selected from hydrogen, $C_{1-4}$ alkyl, and $C_{6-8}$ aryl; D is selected from a therapeutic agent having at least one primary amine group and a therapeutic agent having at least one secondary amine group; and n5 is selected from 1 to 5.

In certain embodiments of a compound of Formula (II), each $A^1$ is a moiety of Formula ($A^1$f2); each $X^1$ is methane-diyl; each $X^2$ is a covalent bond; each $X^3$ is a covalent bond; each $R^1$ is hydrogen; each $R^2$ is hydrogen; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$f2); each $X^1$ is methane-diyl; each $X^2$ is —C(O)N—; each $X^3$ is pentane-1,5-diyl; each $R^1$ is hydrogen; each $R^2$ is methyl; D is selected from a therapeutic agent having at least one primary amine group and a therapeutic agent having at least one secondary amine group; and n5 is selected from 1 to 4.

In certain embodiments of a compound of Formula (II), each $A^1$ is a moiety of Formula ($A^1$f2); each $X^1$ is methane-diyl; each $X^2$ is —C(O)N—; each $X^3$ is 4-methylcyclohex-ane-diyl; each $R^1$ is hydrogen; each $R^2$ is methyl; D is selected from a therapeutic agent having at least one primary amine group and a therapeutic agent having at least one secondary amine group; and n5 is selected from 1 to 4.

In certain embodiments of a compound of Formula (II), the compound is selected from a compound of Formula (II-a), Formula (II-b), Formula (II-c), Formula (II-d), Formula (II-e), Formula (II-f), Formula (II-g), Formula (II-h), Formula (II-i), Formula (II-j), Formula (II-k), Formula (II-l), Formula (II-m), Formula (II-n), Formula (II-o), Formula (II-p), Formula (II-q), Formula (II-r), Formula (II-s), Formula (II-t), Formula (II-u), Formula (II-v), Formula (II-w), Formula (II-x), Formula (II-y), Formula (II-z), Formula (II-aa), Formula (II-ab), and Formula (II-ac), or a salt of any of the foregoing:

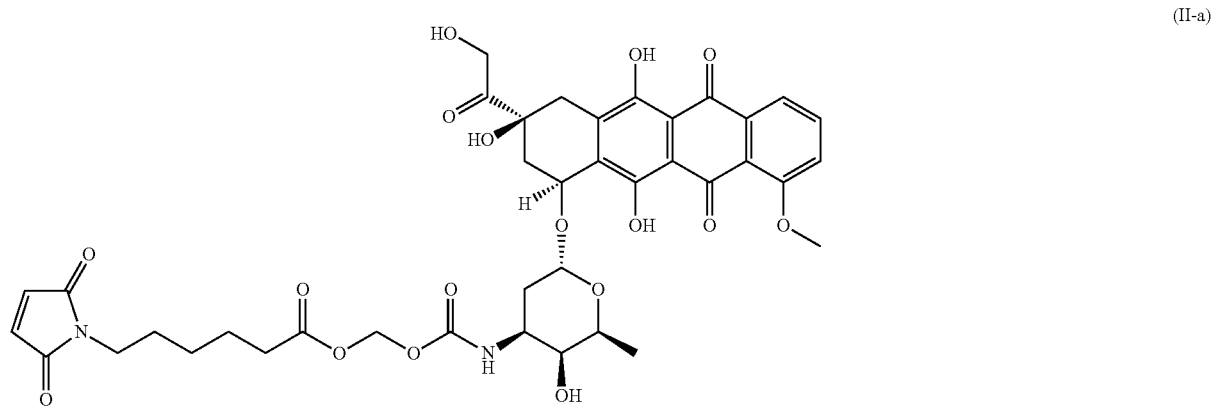

(II-a)

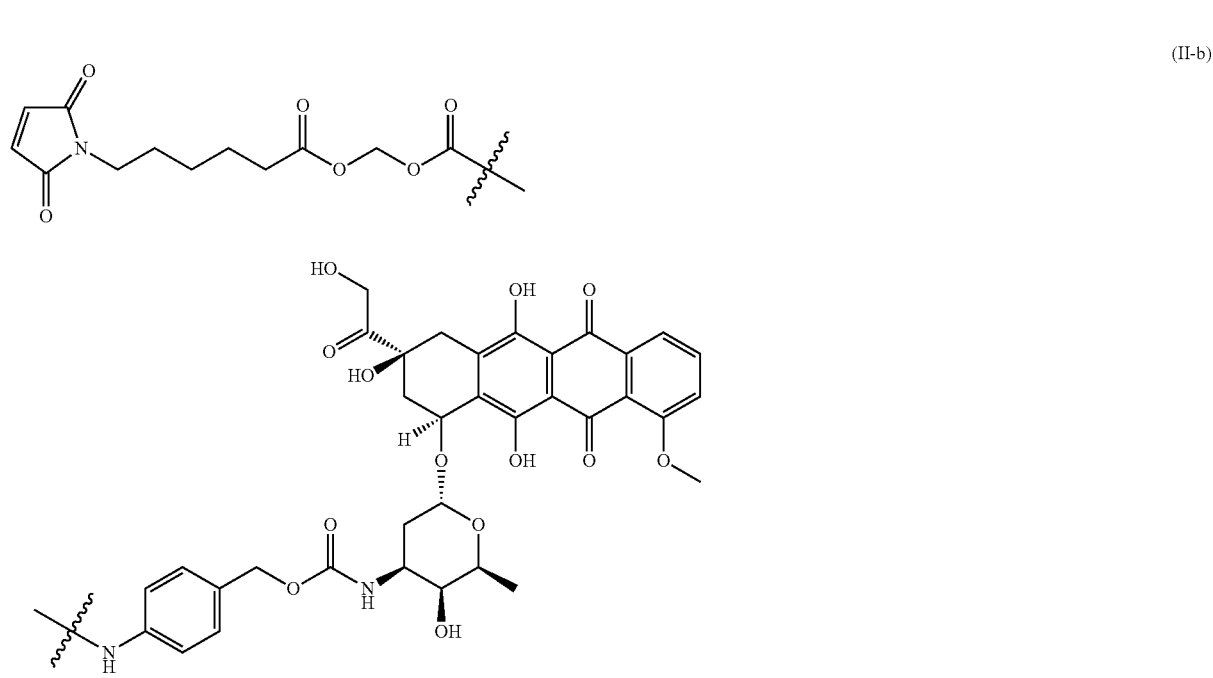

(II-b)

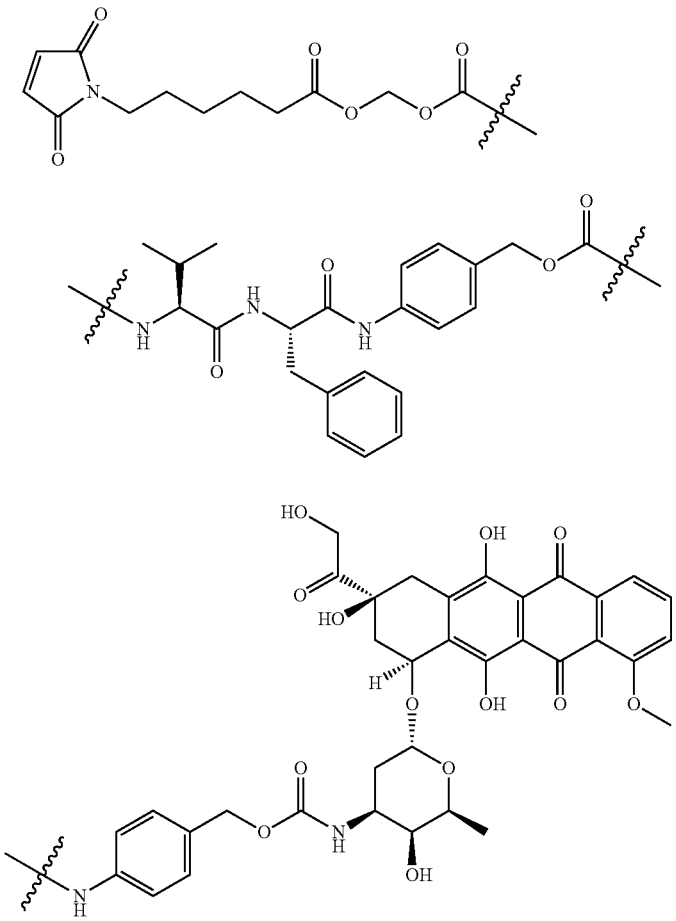
(II-c)
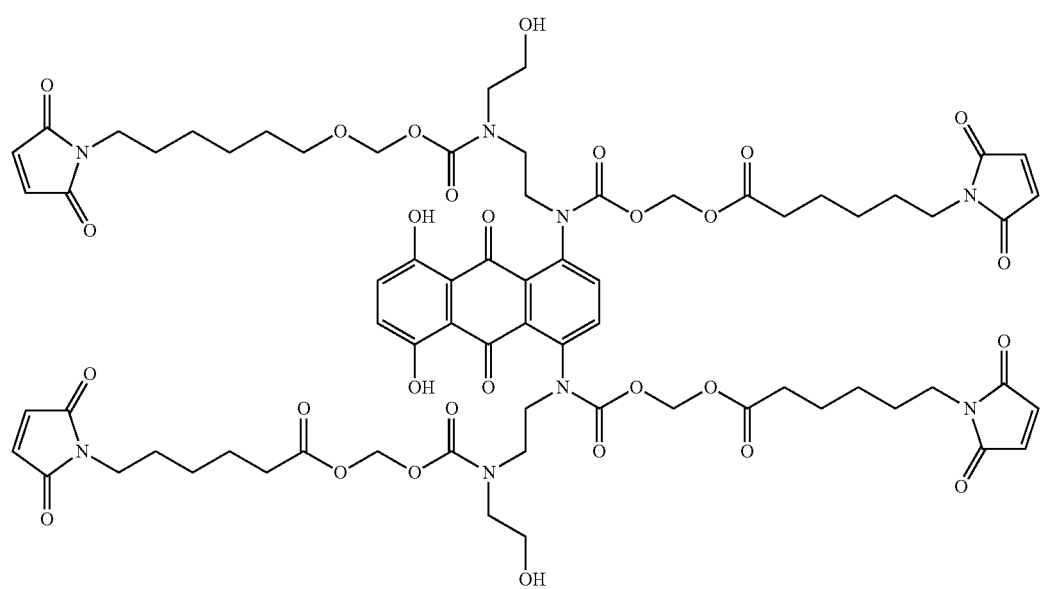
(II-d)

-continued
(II-e)
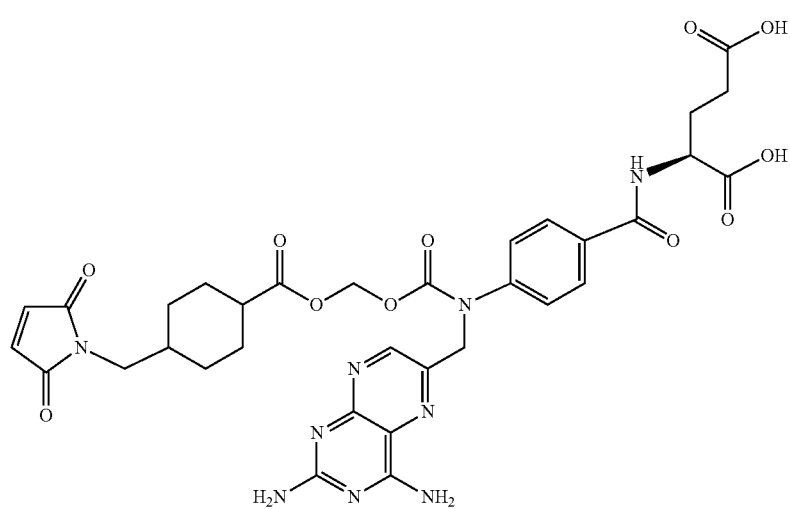
(II-f)
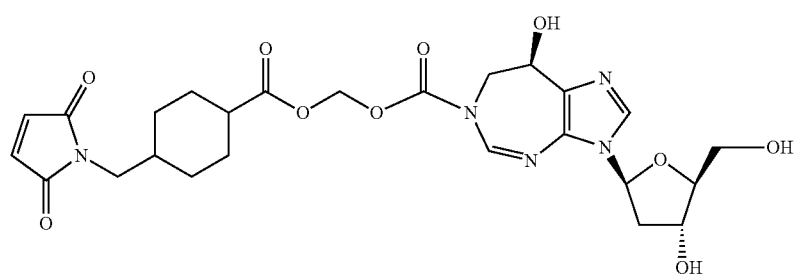
(II-g)
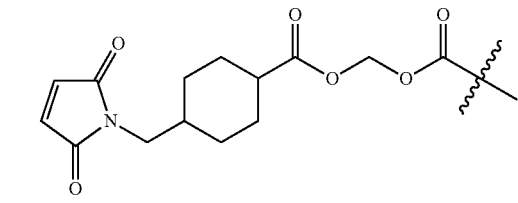
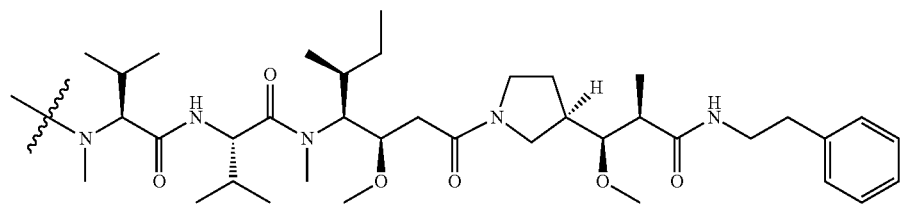
(II-h)
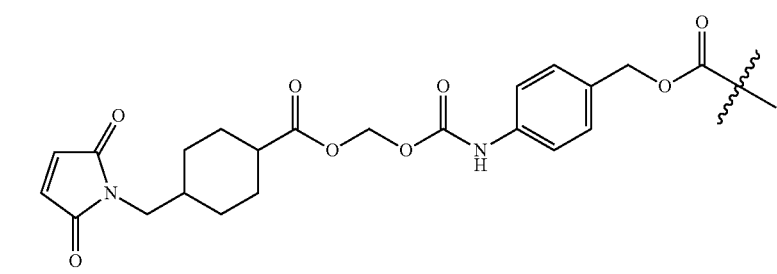
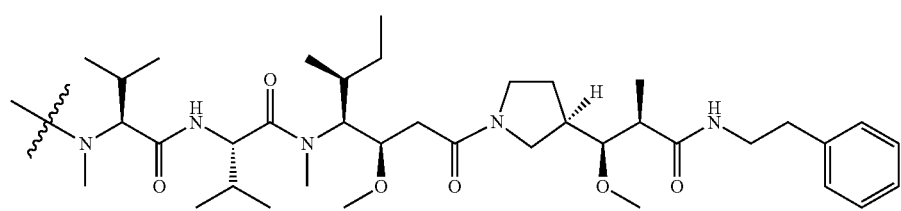

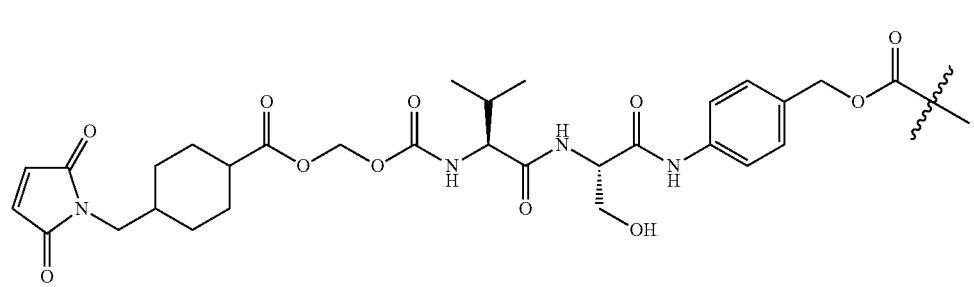
(II-i)
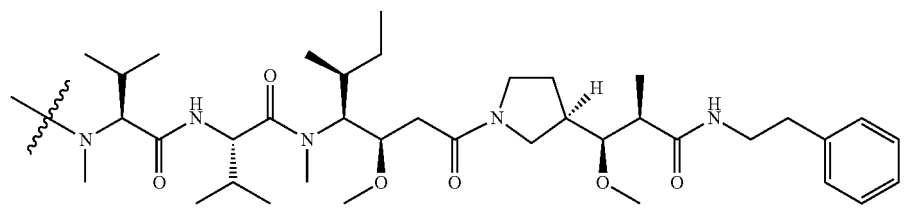
(II-j)
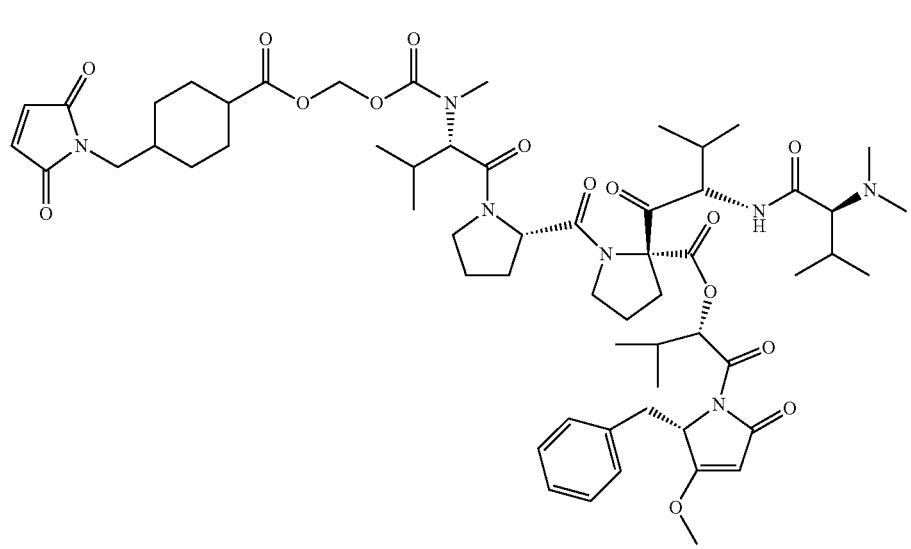
(II-k)
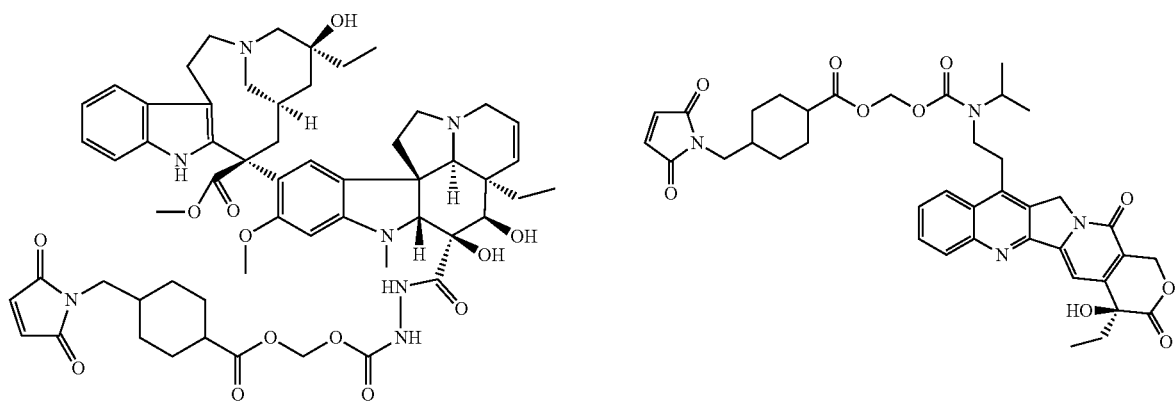
(II-l)

-continued
(II-m)
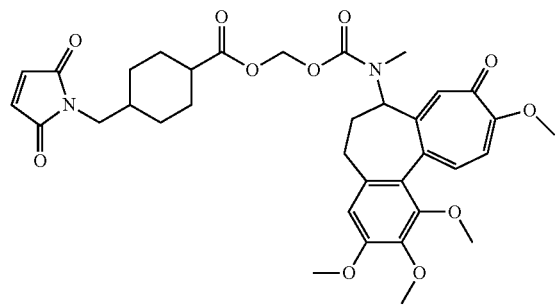
(II-n)
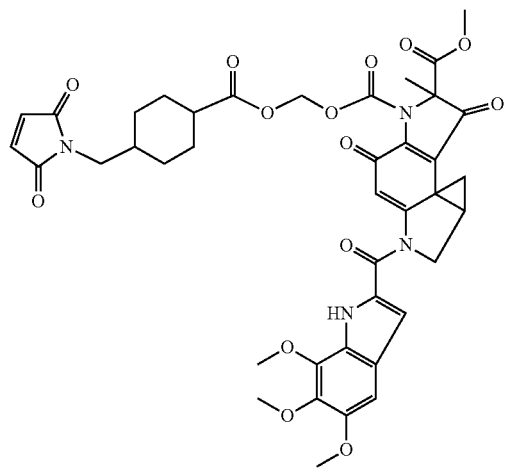
(II-o)
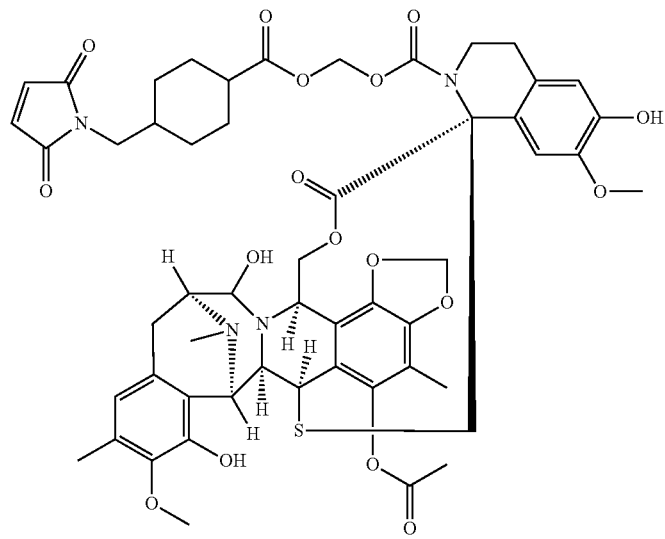
(II-p)
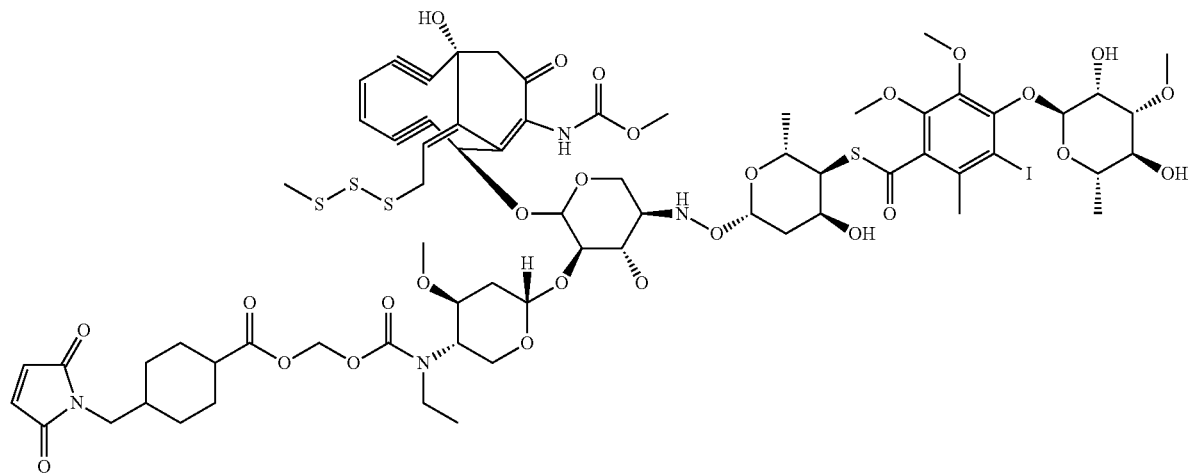

(II-q)
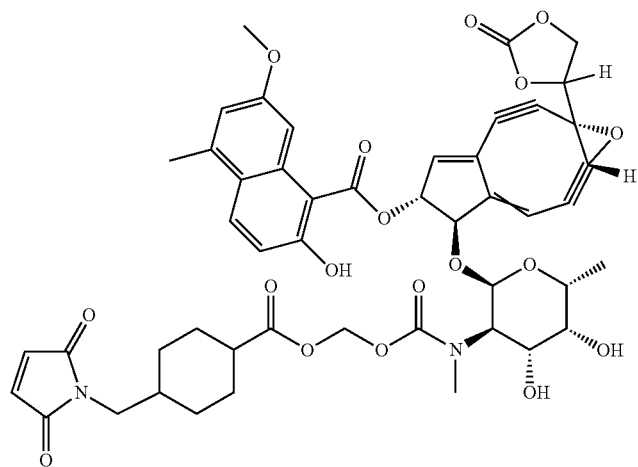
(II-r)
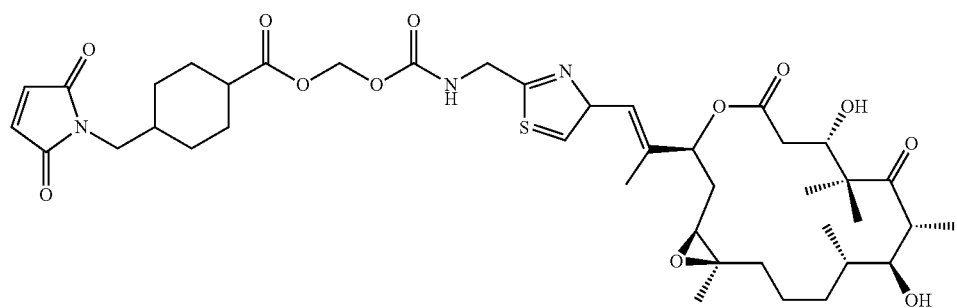
(II-s)
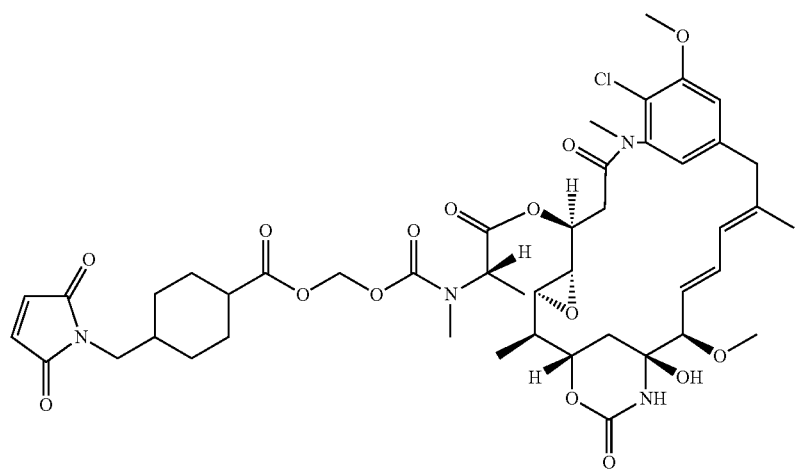

(II-t)
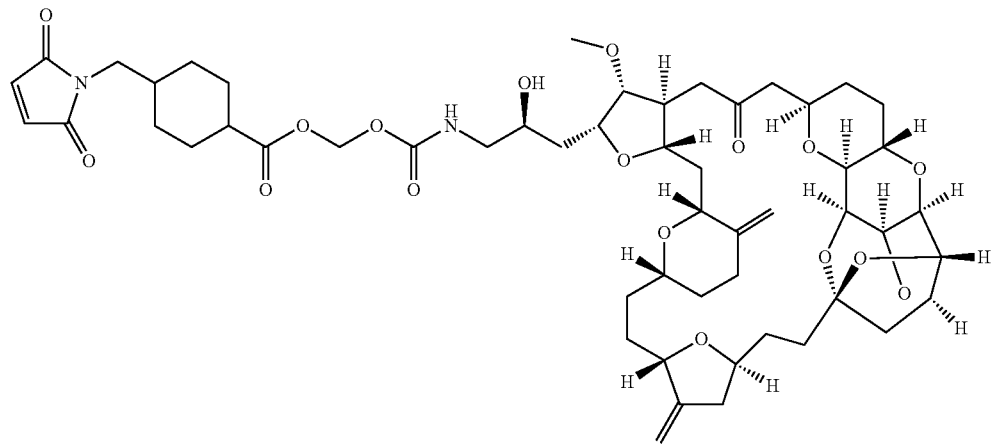
(II-u)
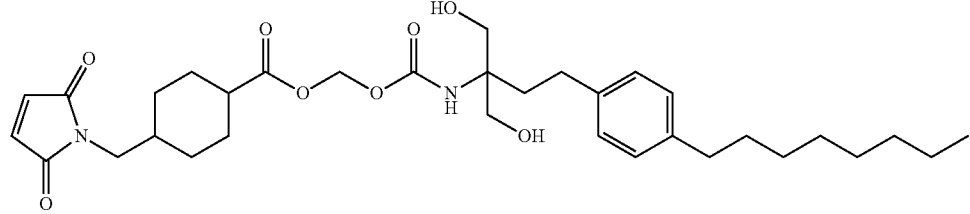
(II-v)
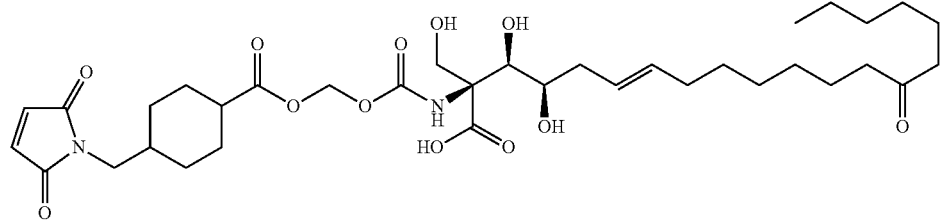
(II-w)
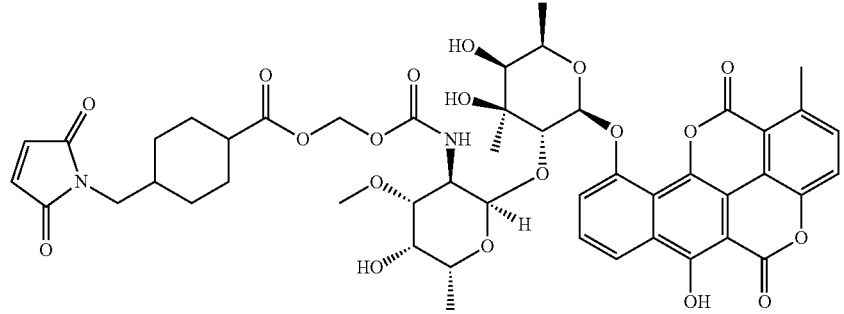
(II-x)                                    (II-y)
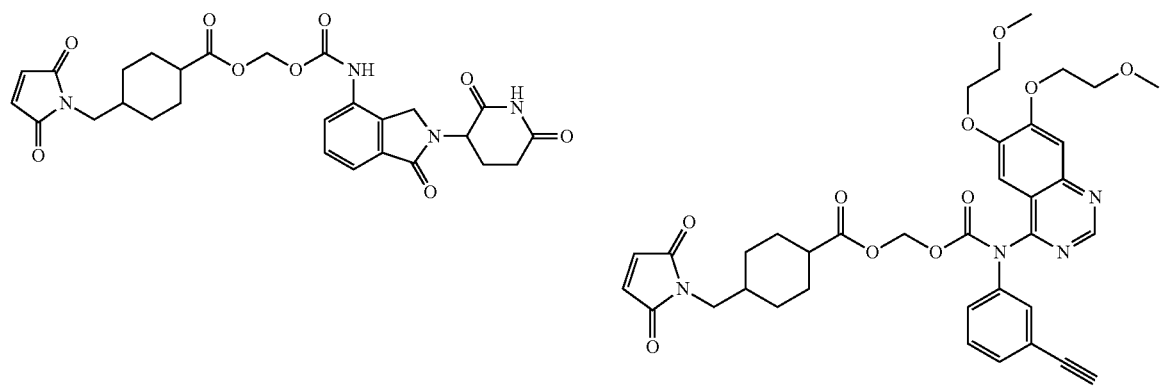

-continued

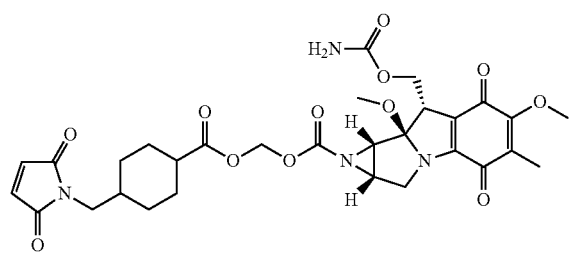

(II-z)

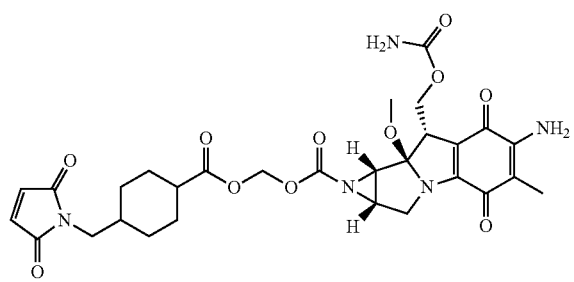

(II-aa)

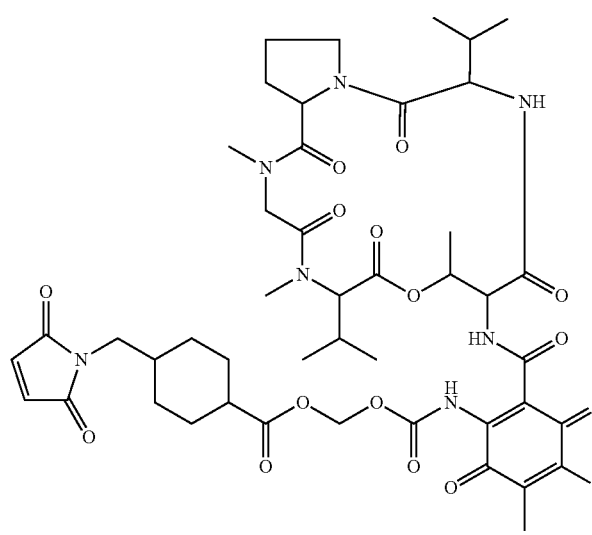

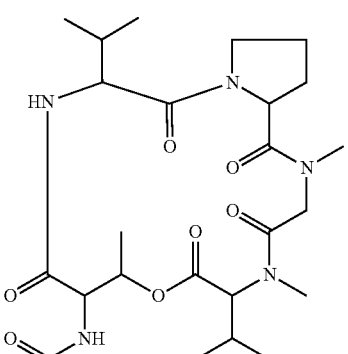

(II-ab)

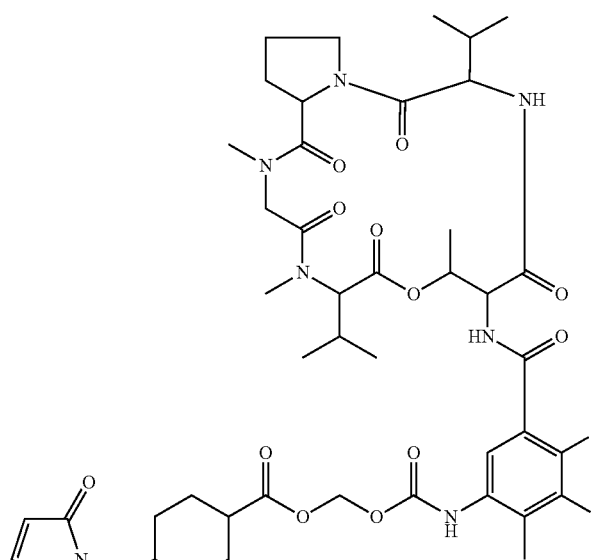

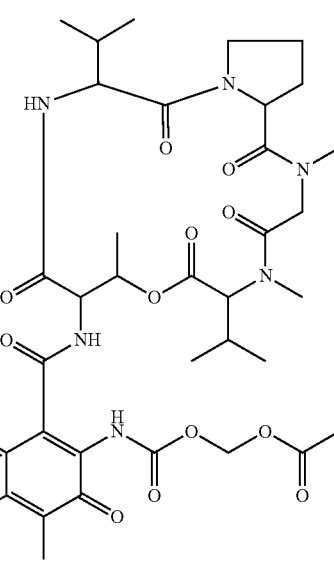

(II-ac)

In certain embodiments, a compound of Formula (II) is a compound of Formula (I-a) or a salt thereof.

In certain embodiments, a compound of Formula (II) is a compound of Formula (II-b) or a salt thereof.

In certain embodiments, a compound of Formula (II) is a compound of Formula (II-c) or a salt thereof.

In certain embodiments, a compound of Formula (II) is a compound of Formula (II-d) or a salt thereof.

In certain embodiments, a compound of Formula (II) is a compound of Formula (II-e) or a salt thereof.

In certain embodiments, a compound of Formula (II) is a compound of Formula (II-f) or a salt thereof.

In certain embodiments, a compound of Formula (II) is a compound of Formula (II-g) or a salt thereof.

In certain embodiments, a compound of Formula (II) is a compound of Formula (II-h) or a salt thereof.

In certain embodiments, a compound of Formula (II) is a compound of Formula (II-i) or a salt thereof.

In certain embodiments, a compound of Formula (II) is a compound of Formula (II-j) or a salt thereof.

In certain embodiments, a compound of Formula (II) is a compound of Formula (II-k) or a salt thereof.

In certain embodiments, a compound of Formula (II) is a compound of Formula (II-l) or a salt thereof.

In certain embodiments, a compound of Formula (II) is a compound of Formula (II-m) or a salt thereof.

In certain embodiments, a compound of Formula (II) is a compound of Formula (II-n) or a salt thereof.

In certain embodiments, a compound of Formula (II) is a compound of Formula (II-o) or a salt thereof.

In certain embodiments, a compound of Formula (II) is a compound of Formula (II-p) or a salt thereof.

In certain embodiments, a compound of Formula (II) is a compound of Formula (II-q) or a salt thereof.

In certain embodiments, a compound of Formula (II) is a compound of Formula (II-r) or a salt thereof.

In certain embodiments, a compound of Formula (II) is a compound of Formula (II-s) or a salt thereof.

In certain embodiments, a compound of Formula (II) is a compound of Formula (II-t) or a salt thereof.

In certain embodiments, a compound of Formula (II) is a compound of Formula (II-u) or a salt thereof.

In certain embodiments, a compound of Formula (II) is a compound of Formula (II-v) or a salt thereof.

In certain embodiments, a compound of Formula (II) is a compound of Formula (II-w) or a salt thereof.

In certain embodiments, a compound of Formula (II) is a compound of Formula (II-x) or a salt thereof.

In certain embodiments, a compound of Formula (II) is a compound of Formula (II-y) or a salt thereof.

In certain embodiments, a compound of Formula (II) is a compound of Formula (II-z) or a salt thereof.

In certain embodiments, a compound of Formula (II) is a compound of Formula (II-aa) or a salt thereof.

In certain embodiments, a compound of Formula (II) is a compound of Formula (II-ab) or a salt thereof.

In certain embodiments, a compound of Formula (II) is a compound of Formula (II-ac) or a salt thereof.

In certain embodiments, conjugates have the structure of Formula (III):

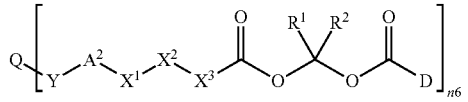

(III)

a pharmaceutically acceptable salt thereof, wherein:
Q is selected from a ligand having at least one thiol group, a ligand having at least one primary amine group, a ligand having at least one secondary amine group, a ligand having at least one biotin-binding group, a ligand having at least one photoreactive group, a ligand having at least one alkyne group, and a ligand having at least one azide group;
each Y is independently selected from a covalent bond and a hydrogen bond;
each $A^2$ is independently selected from a covalent bond, an amide group, an avidin-binding group, a carbamate group, a carbonyl group, a disulfide group, an ester group, a hydrazone group, an imine group, a succinimide group, a sulfonamide group, a sulfone group, a sulfoxide group, a thioether group, a triazole group, and a urea group;
each $X^1$ and $X^3$ is independently selected from a covalent bond, $C_{1-20}$ alkanediyl, substituted $C_{1-20}$ alkanediyl, $C_{1-20}$ heteroalkanediyl, substituted $C_{1-20}$ heteroalkanediyl, $C_{3-12}$ cycloalkanediyl, substituted $C_{3-12}$ cycloalkanediyl, $C_{3-12}$ heterocycloalkanediyl, substituted $C_{3-12}$ heterocycloalkanediyl, $C_{4-20}$ alkanecycloalkanediyl, substituted $C_{4-20}$ alkanecycloalkanediyl, $C_{4-20}$ heteroalkanecycloalkanediyl, substituted $C_{4-20}$ heteroalkanecycloalkanediyl, $C_{6-20}$ arenediyl, substituted $C_{6-20}$ arenediyl, $C_{6-20}$ heteroarenediyl, substituted $C_{6-20}$ heteroarenediyl, $C_{7-20}$ alkanearenediyl, substituted $C_{7-20}$ alkanearenediyl, $C_{6-20}$ heteroalkanearenediyl, substituted $C_{6-20}$ heteroalkanearenediyl, and —$(CH_2)_{n1}$—$(CH_2$—$CH_2$—$O)_{n2}$—$(CH_2)_{n3}$—,
wherein:
each n1 and n3 is independently an integer selected from 0 to 5; and
each n2 is independently an integer selected from 1 to 25;
each $X^2$ is independently selected from a covalent bond, —O—, —S—, —N—, —N=, —N=N—, —N=C—, —SO—, —SO$_2$—, —SO$_2$N—, —SS—, —C(O)—, —C(O)O—, —C(O)N—, —C(O)S—, —C(O)N=, —OP(O)(OH)O—, —OC(O)O—, —OC(O)N—, —NC(O)N—, and —NC(S)N;
each $R^1$ and $R^2$ is independently selected from hydrogen, $C_{1-6}$ alkyl, substituted $C_{1-6}$ alkyl, $C_{1-6}$ heteroalkyl, substituted $C_{1-6}$ heteroalkyl, $C_{6-10}$ aryl, substituted $C_{6-10}$ aryl, $C_{6-10}$ heteroaryl, and substituted $C_{6-10}$ heteroaryl;
each D is independently selected from therapeutic agent having at least one primary amine group, a therapeutic agent having at least one secondary amine group, a therapeutic agent having at least one hydroxy group, and a therapeutic agent having at least one thiol group; and
n6 is an integer selected from 1 to 20.

In certain embodiments of a compound of Formula (III), Q is a ligand having at least one thiol group, in certain embodiments at least one primary amine group, in certain embodiments at least one secondary amine group, in certain embodiments at least one biotin-binding group, in certain embodiments at least one photoreactive group, in certain embodiments at least one alkyne group, and in certain embodiments at least one azide group.

In certain embodiments of a compound of Formula (III), the ligand is selected from a peptide, a protein, a pegylated protein, a fusion protein, an antibody, an antibody fragment, a polymer, a copolymer, and a lipid.

In certain embodiments of a compound of Formula (III), the ligand having at least one thiol group is selected from a peptide, a protein, a pegylated protein, a fusion protein, an antibody, an antibody fragment, a polymer, a copolymer, and a lipid.

In certain embodiments of a compound of Formula (III), the ligand having at least one primary amine group is selected from a peptide, a protein, a pegylated protein, a fusion protein, an antibody, an antibody fragment, a polymer, a copolymer, and a lipid.

In certain embodiments of a compound of Formula (III), the ligand having at least one secondary amine group is selected from a peptide, a protein, a pegylated protein, a fusion protein, an antibody, an antibody fragment, a polymer, a copolymer, and a lipid.

In certain embodiments of a compound of Formula (III), the ligand having at least one biotin-binding group is selected from a peptide and a protein.

In certain embodiments of a compound of Formula (III), the ligand having at least one biotin-binding group is selected from avidin, deglycosylated avidin, streptavidin, and strep-Tactin.

In certain embodiments of a compound of Formula (III), the ligand having at least one primary photoreactive group is selected from a peptide, a protein, a pegylated protein, a fusion protein, an antibody, an antibody fragment, a polymer, a copolymer, and a lipid.

In certain embodiments of a compound of Formula (III), the ligand having at least one primary alkyne group is selected from a peptide, a protein, a pegylated protein, a fusion protein, an antibody, an antibody fragment, a polymer, a copolymer, and a lipid.

In certain embodiments of a compound of Formula (III), the ligand having at least one primary azide group is selected from a peptide, a protein, a pegylated protein, a fusion protein, an antibody, an antibody fragment, a polymer, a copolymer, and a lipid.

In certain embodiments of a compound of Formula (III), the ligand is a peptide and is selected from glutathione, carnosine, and pantetheine.

In certain embodiments of a compound of Formula (III), the ligand is a protein and is selected from bovine serum albumin, human serum albumin, and lactosaminated human serum albumin.

In certain embodiments of a compound of Formula (III), the ligand is a protein and is selected from avidin, deglycosylated avidin, streptavidin, and strep-Tactin.

In certain embodiments of a compound of Formula (III), the ligand is a protein and is selected from interferon alfa, interferon alfa-2a, interferon alfa-2b, interferon beta, interferon beta-1a, interferon beta-1b, interferon gamma, and interferon gamma-1b.

In certain embodiments of a compound of Formula (III), the ligand is a pegylated protein and is selected from pegylated interferon alfa, pegylated interferon alfa-2a, pegylated interferon alfa-2b, pegylated interferon beta, pegylated interferon beta-1a, pegylated interferon beta-1b, pegylated interferon gamma, and pegylated interferon gamma-1b.

In certain embodiments of a compound of Formula (III), the ligand is an antibody and is selected from a humanized monoclonal antibody, a murine monoclonal antibody, a chimeric monoclonal antibody, and a human monoclonal antibody.

In certain embodiments of a compound of Formula (III), the ligand is an antibody and is selected from abagovomab, abatacept, abciximab, adalimumab, adecatumumab, afelimomab, alefacept, aflibercept, afutuzumab, alacizumab pegol, alefacept, alemtuzumab, anakinra, anatumomab, anrukinzumab, apolizumab, arcitumomab, aselizumab, atacicept, atorolimumab, baminercept, bapineuzumab, basiliximab, bavituximab, bectumomab, belatacept, belimumab, benralizumab, bertilimumab, besilesomab, bevacizumab, biciromab, bifarcept, blinatumomab, brentuximab, briakinumab, briobacept, canakinumab, catumaxomab, cantuzumab, cedelizumab, certolizumab, certolizumab pegol, cetuximab, cintredekin, cintredekin besudotox, citatuzumab, citatuzumab bogatox, cixutumumab, clenoliximab, clivatuzumab, conatumumab, dacetuzumab, dacliximab, daclizumab, dalotuzumab, daratumumab, denileukin diftitox, denosumab, detumomab, dorlixizumab, drozitumab, ecromeximab, eculizumab, edrecolomab, efalizumab, efungumab, ensituximab, efalizumab, elotuzumab, elsilimomab, enlimomab, enlimomab pegol, epitumomab, epitumomab, epitumomab cituxetan, epratuzumab, erlizumab, ertumaxomab, etanercept, etaracizumab, exbivirumab, fanolesomab, faralimomab, farletuzumab, felvizumab, fezakinumab, figitumumab, fontolizumab, foralumab, foravirumab, fresolimumab, galiximab, ganitumab, gantenerumab, gantenerumab, gavilimomab, gemtuzumab, girentuximab, glembatumumab, golimumab, gomiliximab, ibalizumab, ibritumomab, ibritumomab tiuxetan, igovomab, imciromab, infliximab, inolimomab, inotuzumab, intetumumab, ipilimumab, itolizumab, keliximab, labetuzumab, lebrikizumab, lemalesomab, lenercept, lerdelimumab, lexatumumab, libivirumab, lintuzumab, lorvotuzumab, lucatumumab, lumiliximab, mapatumumab, maslimomab, matuzumab, mavrilimumab, mepolizumab, metelimumab, milatuzumab, minretumomab, mirococept, mitumomab, morolimumab, motavizumab, moxetumomab, moxetumomab pasudotox, muromonab-CD3, nacolomab, nacolomab tafenatox, naptumomab, naptumomab estafenatox, natalizumab, nebacumab, necitumumab, nerelimomab, nimotuzumab, ocrelizumab, odulimomab, ofatumumab, olaratumab, olokizumab, omalizumab, oportuzumab, oportuzumab monatox, oregovomab, otelixizumab, oxelumab, pagibaximab, palivizumab, panitumumab, panobacumab, pascolizumab, pegsunercept, pertuzumab, pexelizumab, pintumomab, priliximab, pritumumab, racotumomab, rafivirumab, ramucirumab, ranibizumab, raxibacumab, regavirumab, reslizumab, rilonacept, rilotumumab, rituximab, robatumumab, roledumab, rontalizumab, rovelizumab, ruplizumab, samalizumab, satumomab, secukinumab, sevirumab, sibrotuzumab, sifalimumab, siltuximab, siplizumab, solanezumab, sontuzumab, sotatercept, stamulumab, sulesomab, suvizumab, tacatuzumab, tadocizumab, talizumab, tanezumab, taplitumomab, taplitumomab paptox, tefibazumab, telimomab, telimomab aritox, teneliximab, tenatumomab, teplizumab, teprotumumab, ticilimumab, tigatuzumab, tocilizumab, toralizumab, tositumomab, tralokinumab, trastuzumab, tremelimumab, tucotuzumab, tucotuzumab celmoleukin, tuvirumab, urtoxazumab, ustekinumab, vapaliximab, vedolizumab, veltuzumab, vepalimomab, visilizumab, volociximab, votumumab, zalutumumab, zanolimumab, ziralimumab, zolimomab, zolimomab aritox.

In certain embodiments of a compound of Formula (III), the ligand is a polymer and is selected from polyethylene glycol (PEG), monomethyl polyethylene glycol (MPEG), polypropylene glycol (PPG), polystyrene, and polylactide.

In certain embodiments of a compound of Formula (III), the ligand is a copolymer and is selected from N-(2-hydroxypropyl)methacrylamide (HPMA) copolymer and poly(styrene-co-maleic acid).

In certain embodiments of a compound of Formula (III), the ligand is MPEG having a number average molecular weight from about 100 Daltons to about 60,000 Daltons. In certain embodiments of a compound of Formula (III), the ligand is MPEG having a number average molecular weight from about 1,000 Daltons to about 40,000 Daltons. In certain embodiments of a compound of Formula (III), the ligand is MPEG having a number average molecular weight from about 1,000 Daltons to about 12,500 Daltons.

In certain embodiments of a compound of Formula (III), the ligand is a lipid and is selected from $C_{8-20}$ alkyl.

In certain embodiments of a compound of Formula (III), each Y is the same, and in certain embodiments, at least some Y are different.

In certain embodiments of a compound of Formula (III), each $A^2$ is the same, and in certain embodiments, at least some $A^2$ are different.

In certain embodiments of a compound of Formula (III), each $X^1$ is the same, and in certain embodiments, at least some $X^1$ are different.

In certain embodiments of a compound of Formula (III), each $X^2$ is the same, and in certain embodiments, at least some $X^2$ are different.

In certain embodiments of a compound of Formula (III), each $X^3$ is the same, and in certain embodiments, at least some $X^3$ are different.

In certain embodiments of a compound of Formula (III), each $R^1$ is the same, and in certain embodiments, at least some $R^1$ are different.

In certain embodiments of a compound of Formula (III), each $R^2$ is the same, and in certain embodiments, at least some $R^2$ are different.

In certain embodiments of a compound of Formula (III), each D is the same, and in certain embodiments, at least some D are different.

In certain embodiments of a compound of Formula (III), each group within the bracket is the same, and in certain embodiments, at least one group within the brackets is different.

In certain embodiments of a compound of Formula (III), each Y is independently selected from a covalent bond and a hydrogen bond.

In certain embodiments of a compound of Formula (III), each Y is a covalent bond to the at least one thiol group. In certain embodiments of a compound of Formula (III), each Y is a covalent bond to the at least one primary amine group. In certain embodiments of a compound of Formula (III), each Y is a covalent bond to the at least one secondary amine group. In certain embodiments of a compound of Formula (III), each Y is a covalent bond to the at least one photoreactive group. In certain embodiments of a compound of Formula (III), each Y is a covalent bond to the at least one triazole group. In certain embodiments of a compound of Formula (III), each Y is a covalent bond to the at least one succinimide group. In certain embodiments of a compound of Formula (III), each Y is a hydrogen bond to the at least one biotin-binding group.

In certain embodiments of a compound of Formula (III), each $A^2$ is independently selected from a covalent bond, an amide group, an avidin-binding group, a carbamate group, a carbonyl group, a disulfide group, an ester group, a hydrazone group, an imine group, a succinimide group, a sulfonamide group, a sulfone group, a sulfoxide group, a thioether group, a triazole group, and a urea group.

In certain embodiments of a compound of Formula (III), each $A^2$ is independently selected from a covalent bond, —C(O)N—, —C(O)O—, —C=N—, —C(O)N—N=C—, —OC(O)N—, —NC(O)N—, —SO$_2$—, —SO$_2$N—, —S—, —SS—, a moiety of Formula ($A^2$a1), a moiety of Formula ($A^2$b2), a moiety of Formula ($A^2$c1), a moiety of Formula ($A^2$c2), a moiety of Formula ($A^2$c3), a moiety of Formula ($A^2$f1), and a moiety of Formula ($A^2$f2):

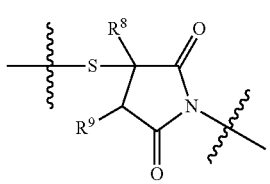
($A^2$a1)

-continued

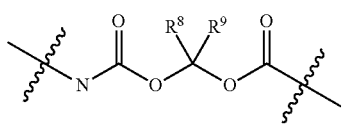
($A^2$b2)

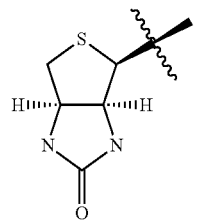
($A^2$c1)

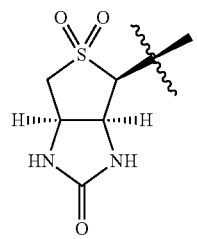
($A^2$c2)

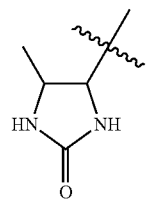
($A^2$c3)

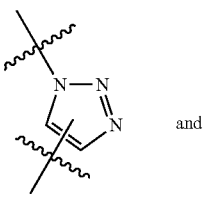
($A^2$f1)

and

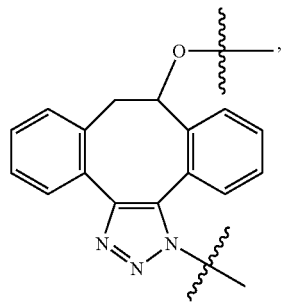
($A^2$f2)

wherein each $R^8$ and $R^9$ is independently selected from hydrogen, $C_{1-4}$ alkyl, substituted $C_{1-4}$ alkyl, $C_{1-4}$ heteroalkyl, substituted $C_{1-4}$ heteroalkyl, $C_{6-10}$ aryl, substituted $C_{6-10}$ aryl, $C_{6-10}$ heteroaryl, and substituted $C_{6-10}$ heteroaryl.

In certain embodiments of a compound of Formula (III), each $A^2$ is a thioether group and is independently selected from —S— and a moiety of Formula ($A^2$a1).

In certain embodiments of a compound of Formula (III), each $A^2$ is an amide group and is independently selected from —C(O)N— and a moiety of Formula ($A^2$b2).

In certain embodiments of a compound of Formula (III), each $A^2$ is an avidin-binding group and is independently selected from a moiety of Formula ($A^2$c1), a moiety of Formula ($A^2$c2), and a moiety of Formula ($A^2$c3).

In certain embodiments of a compound of Formula (III), each $A^2$ is a triazole group and is independently selected from a moiety of Formula ($A^2$f1) and a moiety of Formula ($A^2$f2).

In certain embodiments of a compound of Formula (III), each $A^2$ is Formula ($A^2$a1). In certain embodiments of a compound of Formula (III), each $A^2$ is Formula ($A^2$a1), wherein each $R^8$ and $R^9$ is independently selected from hydrogen, $C_{1-4}$ alkyl and $C_{6-8}$ aryl; in certain embodiments, each $R^8$ and $R^9$ is independently selected from hydrogen, $C_{1-2}$ alkyl, and $C_6$ aryl; and in certain embodiments, each $R^8$ and $R^9$ is hydrogen.

In certain embodiments of a compound of Formula (III), each $A^2$ is Formula ($A^2$b2). In certain embodiments of a compound of Formula (III) wherein each $A^2$ is Formula ($A^2$b2), each $R^8$ and $R^9$ is independently selected from hydrogen, $C_{1-4}$ alkyl, and $C_{6-8}$ aryl. In certain embodiments of a compound of Formula (III) wherein each $A^2$ is Formula ($A^2$b2), each $R^8$ and $R^9$ is independently selected from hydrogen, methyl, ethyl, propyl, isopropyl, and phenyl. In certain embodiments of a compound of Formula (III) wherein each $A^2$ is Formula ($A^2$b2), each $R^8$ and $R^9$ is hydrogen.

In certain embodiments of a compound of Formula (III), each $A^2$ is Formula ($A^2$c1). In certain embodiments of a compound of Formula (III), each $A^2$ is Formula ($A^2$c2). In certain embodiments of a compound of Formula (III), each $A^2$ is Formula ($A^2$c3). In certain embodiments of a compound of Formula (III), each $A^2$ is Formula ($A^2$f1). In certain embodiments of a compound of Formula (III), each $A^2$ is Formula ($A^2$f2).

In certain embodiments of a compound of Formula (III), each $X^1$ and $X^3$ is independently selected from a covalent bond, $C_{1-20}$ alkanediyl, substituted $C_{1-20}$ alkanediyl, $C_{3-12}$ cycloalkanediyl, substituted $C_{3-12}$ cycloalkanediyl, substituted $C_{3-12}$ heterocycloalkanediyl, $C_{6-20}$ arenediyl, substituted $C_{6-20}$ arenediyl, $C_{7-20}$ alkanearenediyl, substituted $C_{7-20}$ alkanearenediyl, and —$(CH_2)_{n1}$—$(CH_2$—$CH_2$—$O)_{n2}$—$(CH_2)_{n3}$—, wherein each n1 and n3 is independently an integer selected from 0 to 5 and each n2 is independently an integer selected from 1 to 25.

In certain embodiments of a compound of Formula (III), each $X^1$ and $X^3$ is independently selected from a covalent bond, $C_{1-16}$ alkanediyl, substituted $C_{1-16}$ alkanediyl, $C_{3-6}$ cycloalkanediyl, benzene-diyl, substituted benzene-diyl, $C_{7-9}$ benzenealkane-diyl, and —$(CH_2)_{n1}$—$(CH_2$—$CH_2$—$O)_{n2}$—$(CH_2)_{n3}$—, wherein each n1 and n3 is independently an integer selected from 0 to 5 and each n2 is independently an integer selected from 1 to 20.

In certain embodiments of a compound of Formula (III), each $X^1$ and $X^3$ is independently selected from a covalent bond, $C_{1-8}$ alkanediyl, substituted $C_{1-8}$ alkanediyl, $C_{3-8}$ cycloalkanediyl, benzene-diyl, substituted benzene-diyl, $C_{7-9}$ benzenealkane-diyl, and —$(CH_2)_{n1}$—$(CH_2$—$CH_2$—$O)_{n2}$—$(CH_2)_{n3}$—, wherein each n1 and n3 is independently an integer selected from 0 to 3 and each n2 is independently an integer selected from 1 to 10.

In certain embodiments of a compound of Formula (III), each $X^1$ is selected from $C_{1-20}$ alkanediyl, $C_{1-20}$ cycloalkanediyl, $C_{6-10}$ arenediyl, and $C_{7-20}$ alkanearenediyl. In certain embodiments of a compound of Formula (III), each $X^3$ is selected from $C_{1-20}$ alkanediyl, $C_{1-20}$ cycloalkanediyl, $C_{6-10}$ arenediyl, and $C_{7-20}$ alkanearenediyl.

In certain embodiments of a compound of Formula (III), each $X^1$ is a covalent bond.

In certain embodiments of a compound of Formula (III), each $X^3$ is a covalent bond.

In certain embodiments of a compound of Formula (III), each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3 and each n2 is independently an integer selected from 1 to 20.

In certain embodiments of a compound of Formula (III), each $X^1$ and $X^3$ is independently selected from a covalent bond, methane-diyl, ethane-1,2-diyl, propane-1,3-diyl, pentane-1,5-diyl, 4-methylcyclohexane-diyl, benzene-1,2-diyl, benzene-1,3-diyl, and benzene-1,4-diyl.

In certain embodiments of a compound of Formula (III), each $X^1$ is a covalent bond; and each $X^3$ is selected from a covalent bond, methane-diyl, ethane-1,2-diyl, propane-1,3-diyl, pentane-1,5-diyl, 4-methylcyclohexane-diyl, benzene-1,2-diyl, benzene-1,3-diyl, and benzene-1,4-diyl.

In certain embodiments of a compound of Formula (III), each $X^1$ is ethane-1,2-diyl; and each $X^3$ is selected from a covalent bond, methane-diyl, ethane-1,2-diyl, propane-1,3-diyl, pentane-1,5-diyl, 4-methylcyclohexane-diyl, benzene-1,2-diyl, benzene-1,3-diyl, and benzene-1,4-diyl.

In certain embodiments of a compound of Formula (III), each $X^1$ is pentane-1,5-diyl; and each $X^3$ is selected from a covalent bond, methane-diyl, ethane-1,2-diyl, propane-1,3-diyl, pentane-1,5-diyl, 4-methylcyclohexane-diyl, benzene-1,2-diyl, benzene-1,3-diyl, and benzene-1,4-diyl.

In certain embodiments of a compound of Formula (III), each $X^1$ is 4-methylcyclohexane-diyl; and $X^3$ is selected from a covalent bond, methane-diyl, ethane-1,2-diyl, propane-1,3-diyl, pentane-1,5-diyl, 4-methylcyclohexane-diyl, benzene-1,2-diyl, benzene-1,3-diyl, and benzene-1,4-diyl.

In certain embodiments of a compound of Formula (III) wherein each $X^1$ and/or $X^3$ is —$(CH_2)_{n1}$—$(CH_2$—$CH_2$—$O)_{n2}$—$(CH_2)_{n3}$—, each n1 and n3 is independently an integer selected from 0 to 5, an integer selected from 0 to 4, an integer selected from 0 to 3, and in certain embodiments, an integer selected from 0 to 2. In certain embodiments of a compound of Formula (III) wherein each $X^1$ and/or $X^3$ is —$(CH_2)_{n1}$—$(CH_2$—$CH_2$—$O)_{n2}$—$(CH_2)_{n3}$—, each n2 is independently an integer selected from 1 to 25, an integer selected from 1 to 20, an integer selected from 1 to 15, an integer selected from 1 to 10, an integer selected from 1 to 5, an integer selected from 1 to 4, and in certain embodiments, an integer selected from 1 to 3.

In certain embodiments of a compound of Formula (III), each n1 and n3 is independently an integer selected from 0 to 5, in certain embodiments, an integer selected from 0 to 4, and in certain embodiments, an integer selected from 0 to 3; and each n2 is independently an integer selected from 1 to 25, in certain embodiments an integer selected from 1 to 20, in certain embodiments an integer selected from 1 to 15, in certain embodiments an integer selected from 1 to 10, and in certain embodiments an integer selected from 1 to 5.

In certain embodiments of a compound of Formula (III), each $X^2$ is selected from a covalent bond, —O—, —S—, —N—, —N=, —N=N—, —N=C—, —SO—, —SO_2—, —SO_2N—, —SS—, —C(O)—, —C(O)O—, —C(O)N—, —C(O)S—, —C(O)N—N=, —OP(O)(OH)O—, —OC(O)O—, —OC(O)N—, —NC(O)N—, and —NC(S)N. In certain embodiments of a compound of Formula (III), each $X^2$ is selected from a covalent bond, —O—, —S—, —SO—, —SO$_2$—, —SO$_2$N—, —SS—, —C(O)—, —C(O)O—, —C(O)N—, —C(O)N—N=, —OC(O)N—, and —NC(O)N—. In certain embodiments of a compound of Formula (III), each $X^2$ is selected from a covalent bond, —SO$_2$—, —SO$_2$N—, and —C(O)N—.

In certain embodiments of a compound of Formula (III), each $R^1$ and $R^2$ is independently selected from hydrogen, $C_{1-6}$ alkyl, substituted $C_{1-6}$ alkyl, $C_{1-6}$ heteroalkyl, substituted $C_{1-6}$ heteroalkyl, $C_{6-10}$ aryl, substituted $C_{6-10}$ aryl, $C_{6-10}$ heteroaryl, and substituted $C_{6-10}$ heteroaryl.

In certain embodiments of a compound of Formula (III), each $R^1$ and $R^2$ is independently selected from hydrogen, $C_{1-6}$ alkyl, substituted $C_{1-6}$ alkyl, and $C_{6-10}$ aryl. In certain embodiments of a compound of Formula (III), $R^1$ and $R^2$ are independently selected from hydrogen, methyl, ethyl, propyl, isopropyl, and phenyl. In certain embodiments of a compound of Formula (III), each $R^1$ and $R^2$ is independently selected from hydrogen and methyl. In certain embodiments of a compound of Formula (III), each $R^1$ and $R^2$ is independently selected from hydrogen and ethyl. In certain embodiments of a compound of Formula (III), each $R^1$ and $R^2$ is independently selected from hydrogen and propyl. In certain embodiments of a compound of Formula (III), each $R^1$ and $R^2$ is independently selected from hydrogen and isopropyl. In certain embodiments of a compound of Formula (III), each $R^1$ and $R^2$ is independently selected from hydrogen and phenyl.

In certain embodiments of a compound of Formula (III), each $R^1$ and $R^2$ is hydrogen. In certain embodiments of a compound of Formula (III), each $R^1$ is hydrogen and each $R^2$ is methyl. In certain embodiments of a compound of Formula (III), each $R^1$ is hydrogen and each $R^2$ is ethyl. In certain embodiments of a compound of Formula (III), each $R^1$ is hydrogen and each $R^2$ is propyl. In certain embodiments of a compound of Formula (III), each $R^1$ is hydrogen and each $R^2$ is isopropyl. In certain embodiments of a compound of Formula (III), each $R^1$ is hydrogen and each $R^2$ is phenyl.

In certain embodiments of a compound of Formula (III), each D is independently selected from a therapeutic agent having at least one primary amine group, a therapeutic agent having at least one secondary amine group, a therapeutic agent having at least one hydroxy group, and a therapeutic agent having at least one thiol group.

In certain embodiments of a compound of Formula (III), each D is independently selected from a folic acid analog, a purine analog, a pyrimidine analog, an anthracycline derivative, a dolastatin derivative, a camptotheca derivative, an ectainascidin derivative, a colchicine derivative, a duocarmycin derivative, an enediyne derivative, an epothilone derivative, a halichondrin derivative, a kahalalide derivative, a *streptomyces*, a tubulysin derivative, a vinca alkaloid, an antifolate, a hemiasterlin, a cathepsin K inhibitor, dipeptidyl peptidase IV inhibitor, heat shock protein 90 (Hsp90) inhibitor, a histone deacetylase inhibitor, an immunomodulator, an aurora kinase inhibitor, a cyclin-dependent kinase inhibitor, tyrosine kinase inhibitor, kinesin-related motor protein Eg5 inhibitor, kinesin spindle protein inhibitor, microtubule interference compounds, topoisomerase inhibitor, and an antibiotic.

In certain embodiments of a compound of Formula (III), each D is independently selected from aminopterin, folitixorin, methotrexate, pemetrexed, pralatrexate, raltitrexed, pelitrexol, talotrexin, deoxycoformycin, cladribine, clofarabine, fludarabine, thioguanine, mercaptopurine, berubicin, daunorubicin, doxorubicin, epirubicin, idarubicin, amrubicin, pirarubicin, zorubicin, mitoxantrone, banoxantrone, ledoxantrone, nortopixantrone, pixantrone, piroxantrone, sabarubicin, topixantrone, monomethyl auristatin E, monomethyl auristatin F, monomethyl dolastatin 10, dolastatin 15, belotecan, atiratecan, camptothecin, exatecan, irinotecan, namitecan, rubitecan, topotecan, demecolcine, duocarmycin A, duocarmycin SA, duocarmycin B, duocarmycin B1, abbeymycin, anthramycin, centanamycin, chicamycin, mazethramycin, porothramycin A, porothramycin B, sibanomycin, sibiromycin, trabectedin, calicheamicin γ1, calicheamicin T, esperamicin A1, esperamicin C, esperamicin D, dynemicin A, dynemicin H, dynemicin M, dynemicin N, dynemicin O, dynemicin P, dynemicin Q, dynemicin S, neocarzinostatin chromophore, uncialamycin, 21-aminoepothilone B, eribulin, hemiasterlin, HTI-286, kahalatide F, elsamitrucin, lucanthone, melphalan, mitoguazone, nimustine, procarbazine, dacarbazine, amsacrine, 5-amino-4-oxopentanoic acid, methyl 5-amino-4-oxo-pentanoate, actinomycin D, 7-aminoactinomycin D, bleomycin, mitomycin, staurosporine, desacetylvinblastine hydrazide, vinblastine, vincristine, vindestine, vinflunine, vinorelbine, afatinib, apilimod, balamapimod, barasertib, bosutinib, canertinib, cevipabulin, crizotinib, dacomitinib, dasatinib, denibulin, dilmapimod, dinaciclib, dovitinib, dutacatib, duvoglustat, edotecarin, elisidepsin, entinostat, epetirimod, erlotinib, fingolimod, fostamatinib, gefitinib, golotimod, gusperimus, imatinib, imiquimod, intedanib, ispinesib, lapatinib, lenalidomide, linifanib, litronesib, losmapimod, metesind, mocetinostat, motesanib, masitinib, myriocin, neratinib, nilotinib, odanacatib, ombrabulin, pamapimod, panobinostat, pazopanib, plerixafor, pomalidomide, razupenem, resiquimod, sabarubicin, saracatinib, seliciclib, selumetinib, sotirimod, squalamine, tacedinaline, talabostat, taltobulin, telatinib, tipifarnib, tozasertib, vandetanib, vatalanib, veliparib, voreloxin, alvespimycin, amikacin, amphotericin B, arbekacin, astromicin, bacitracin, balofloxacin, bederocin, bekanamycin, besifloxacin, brodimoprim, ciprofloxacin, clinafloxacin, colistin, daptomycin, dibekacin, enoxacin, framycetin, garenoxacin, gatifloxacin, gemifloxacin, gentamicin, gentamicin, grepafloxacin, hamycin, hexetidine, hygromycin B, ibacitabine, iclaprim, isepamicin, kanamycin, lomefloxacin, lucimycin, lymecycline, mepartricin, moxifloxacin, natamycin, nemonoxacin, neomycin B, neomycin C, netilmicin, norfloxacin, nystatin, omadacycline, oritavancin, paromomycin, pazufloxacin, perimycin A, perimycin B, perimycin C, pipemidic acid, polymyxin B, puromycin, radezolid, retaspimycin, ribostamycin, rimocidin, sisomicin, sitafloxacin, sparfloxacin, spectinomycin, streptomycin, sulfacetamide, sulfadiazine, sulfadimethoxine, sulfadimidine, sulfafurazole, sulfalene, sulfamazone, sulfamerazine, sulfamethizole, sulfamethoxazole, sulfamethoxypyridazine, sulfametomidine, sulfametoxydiazine, sulfametrole, sulfamoxole, sulfanilamide, sulfaperin, sulfaphenazole, sulfapyridine, sulfathiazole, sulfathiourea, sulfisomidine, teicoplanin, telavancin, tanespimycin, temafloxacin, tetroxoprim, tigecycline, tobramycin, tosufloxacin, trimethoprim, trimethoprim, trovafloxacin, tyrothricin, ulifloxacin, valnemulin, vancomycin, verdamicin, and zabofloxacin.

In certain embodiments of a compound of Formula (III), n6 is an integer selected from 1 to 20; in certain embodiments, an integer selected from 1 to 10; in certain embodiments, an integer selected from 1 to 4; and in certain embodiments, n6 is 1, 2, 3, or 4. In certain embodiments, n6 is 1, n6 is 2, n6 is 3, and in certain embodiments n6 is 4.

In certain embodiments of a compound of Formula (III), Q is a ligand selected from a $C_{5-20}$ alkyl, a polyethylene glycol, an avidin, an albumin, an antibody, a polymer, and a glass ($SiO_2$) substrate; each Y is independently selected from a covalent bond and a hydrogen bond; each $A^2$ is independently selected from a covalent bond, —C(O)N—, —C(O)O—, —C=N—, —C(O)N—N=C—, —OC(O)N—, —NC(O)N—, —SO$_2$—, —SO$_2$N—, —S—, —SS—, a moiety of Formula (A$^2$a1), a moiety of Formula (A$^2$b2), a moiety of Formula (A$^2$c1), a moiety of Formula (A$^2$c2), a moiety of Formula (A$^2$c3), a moiety of Formula (A$^2$f1), and a moiety of Formula (A$^2$f2); each X$^1$ and X$^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 5, and each n2 is independently an integer selected from 1 to 25; each X$^2$ is independently selected from a covalent bond, —O—, —S—, —SO—, —SO$_2$—, —SO$_2$N—, —SS—, —C(O)—, —C(O)O—, —C(O)N—, —C(O)N—N=, —OC(O)N—, and —NC(O)N—; each R$^1$ and R$^2$ is independently selected from hydrogen, C$_{1-4}$ alkyl, and C$_{6-8}$ aryl; each D is selected from a therapeutic agent having at least one primary amine group, a therapeutic agent having at least one secondary amine group, a therapeutic agent having at least one hydroxy group, and a therapeutic agent having at least one thiol group; and n6 is selected from 1 to 20.

In certain embodiments of a compound of Formula (III), Q is a ligand selected from a C$_{5-20}$ alkyl, an MPEG, a human serum albumin, an antibody, a polymer, and a glass (SiO$_2$) substrate; each Y is independently selected from a covalent bond and a hydrogen bond; each A$^2$ is independently selected from a covalent bond, —C(O)N—, —SO$_2$—, —SO$_2$N—, —S—, —SS—, a moiety of Formula (A$^2$a1), a moiety of Formula (A$^2$b2), a moiety of Formula (A$^2$c1), a moiety of Formula (A$^2$c2), a moiety of Formula (A$^2$c3), a moiety of Formula (A$^2$f1), and a moiety of Formula (A$^2$f2); each X$^1$ and X$^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each X$^2$ is selected from a covalent bond, —O—, —SO$_2$—, —SO$_2$N—, —C(O)—, —C(O)O—, and —C(O)N—; each R$^1$ and R$^2$ is independently selected from hydrogen, methyl, ethyl, propyl, isopropyl, and phenyl; each D is selected from a therapeutic agent having at least one primary amine group and a therapeutic agent having at least one secondary amine group; and n6 is selected from 1 to 20.

In certain embodiments of a compound of Formula (III), Q is a C$_{5-20}$ alkyl; each Y is a covalent bond; each A$^2$ is independently selected from a covalent bond, —C(O)N—, —SO$_2$—, —S—, a moiety of Formula (A$^2$a1), a moiety of Formula (A$^2$f1), and a moiety of Formula (A$^2$f2); each X$^1$ and X$^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each X$^2$ is selected from a covalent bond, —O—, —SO$_2$—, —SO$_2$N—, —C(O)—, —C(O)O—, and —C(O)N—; each R$^1$ and R$^2$ is independently selected from hydrogen and methyl; each D is selected from a therapeutic agent having at least one primary amine group and a therapeutic agent having at least one secondary amine group; and n6 is selected from 1 to 5.

In certain embodiments of a compound of Formula (III), Q is a C$_{5-20}$ alkyl; each Y is a covalent bond; each A$^2$ is a moiety of Formula (A$^2$a1); each X$^1$ and X$^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each X$^2$ is selected from a covalent bond, —O—, —SO$_2$—, —SO$_2$N—, —C(O)—, —C(O)O—, and —C(O)N—; each R$^1$ and R$^2$ is independently selected from hydrogen and methyl; each D is selected from a therapeutic agent having at least one primary amine group and a therapeutic agent having at least one secondary amine group; and n6 is selected from 1 to 5.

In certain embodiments of a compound of Formula (III), Q is a C$_{5-20}$ alkyl; each Y is a covalent bond; each A$^2$ is a moiety of Formula (A$^2$a1), wherein each R$^8$ and R$^9$ is hydrogen; each X$^1$ is pentane-1,5-diyl; each X$^2$ is a covalent bond; each X$^3$ is a covalent bond; each R$^1$ and R$^2$ is hydrogen; each D is independently selected from a therapeutic agent having at least one primary amine group and a therapeutic agent having at least one secondary amine group; and n6 is selected from 1 to 4.

In certain embodiments of a compound of Formula (III), Q is a C$_{5-20}$ alkyl; each Y is a covalent bond; each A$^2$ is a moiety of Formula (A$^2$a1), wherein each R$^8$ and R$^9$ is hydrogen; each X$^1$ is 4-methylcyclohexane-diyl; each X$^2$ is a covalent bond; each X$^3$ is a covalent bond; each R$^1$ and R$^2$ is hydrogen; each D is selected from a therapeutic agent having at least one primary amine group and a therapeutic agent having at least one secondary amine group; and n6 is selected from 1 to 4.

In certain embodiments of a compound of Formula (III), Q is a C$_{5-20}$ alkyl; each Y is a covalent bond; each A$^2$ is a moiety of Formula (A$^2$a1), wherein each R$^8$ and R$^9$ is hydrogen; each X$^1$ is pentane-1,5-diyl; each X$^2$ is —C(O)N—; each X$^3$ is pentane-1,5-diyl; each R$^1$ and R$^2$ is hydrogen; each D is selected from a therapeutic agent having at least one primary amine group and a therapeutic agent having at least one secondary amine group; and n6 is selected from 1 to 4.

In certain embodiments of a compound of Formula (III), Q is a C$_{5-20}$ alkyl; each Y is a covalent bond; each A$^2$ is a moiety of Formula (A$^2$f1); each X$^1$ and X$^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each X$^2$ is selected from a covalent bond, —O—, —SO$_2$—, —SO$_2$N—, —C(O)—, —C(O)O—, and —C(O)N—; each R$^1$ and R$^2$ is independently selected from hydrogen and methyl; each D is selected from a therapeutic agent having at least one primary amine group and a therapeutic agent having at least one secondary amine group; and n6 is selected from 1 to 5.

In certain embodiments of a compound of Formula (III), Q is a $C_{5-20}$ alkyl; each Y is a covalent bond; each $A^2$ is a moiety of Formula ($A^2$f1); each $X^1$ is pentane-1,5-diyl; each $X^2$ is a covalent bond; each $X^3$ is a covalent bond; each $R^1$ and $R^2$ is hydrogen; each D is independently selected from a therapeutic agent having at least one primary amine group and a therapeutic agent having at least one secondary amine group; and n6 is selected from 1 to 4.

In certain embodiments of a compound of Formula (III), Q is a $C_{5-20}$ alkyl; each Y is a covalent bond; each $A^2$ is a moiety of Formula ($A^2$f1); each $X^1$ is 4-methylcyclohexane-diyl; each $X^2$ is a covalent bond; each $X^3$ is a covalent bond; each $R^1$ and $R^2$ is hydrogen; each D is selected from a therapeutic agent having at least one primary amine group and a therapeutic agent having at least one secondary amine group; and n6 is selected from 1 to 4.

In certain embodiments of a compound of Formula (III), Q is a $C_{5-20}$ alkyl; each Y is a covalent bond; each $A^2$ is a moiety of Formula ($A^2$f1); each $X^1$ is pentane-1,5-diyl; each $X^2$ is —C(O)N—; each $X^3$ is pentane-1,5-diyl; each $R^1$ and $R^2$ is hydrogen; each D is selected from a therapeutic agent having at least one primary amine group and a therapeutic agent having at least one secondary amine group; and n6 is selected from 1 to 4.

In certain embodiments of a compound of Formula (III), Q is a $C_{5-20}$ alkyl; each Y is a covalent bond; each $A^2$ is a moiety of Formula ($A^2$f2); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; each $X^2$ is selected from a covalent bond, —O—, —$SO_2$—, —$SO_2$N—, —C(O)—, —C(O)O—, and —C(O)N—; each $R^1$ and $R^2$ is independently selected from hydrogen and methyl; each D is selected from a therapeutic agent having at least one primary amine group and a therapeutic agent having at least one secondary amine group; and n6 is selected from 1 to 5.

In certain embodiments of a compound of Formula (III), Q is a $C_{5-20}$ alkyl; each Y is a covalent bond; each $A^2$ is a moiety of Formula ($A^2$f2); each $X^1$ is methane-diyl; each $X^2$ is a covalent bond; each $X^3$ is a covalent bond; each $R^1$ and $R^2$ is hydrogen; each D is independently selected from a therapeutic agent having at least one primary amine group and a therapeutic agent having at least one secondary amine group; and n6 is selected from 1 to 4.

In certain embodiments of a compound of Formula (III), Q is a $C_{5-20}$ alkyl; each Y is a covalent bond; each $A^2$ is a moiety of Formula ($A^2$f2); each $X^1$ is methane-diyl; each $X^2$ is —C(O)N—; each $X^3$ is pentane-1,5-diyl; each $R^1$ and $R^2$ is hydrogen; each D is selected from a therapeutic agent having at least one primary amine group and a therapeutic agent having at least one secondary amine group; and n6 is selected from 1 to 4.

In certain embodiments of a compound of Formula (III), Q is an MPEG having a number average molecular weight from about 10,000 to 60,000 daltons; each Y is a covalent bond; each $A^2$ is independently selected from a covalent bond, —C(O)N—, —$SO_2$—, —S—, a moiety of Formula ($A^2$a1), a moiety of Formula ($A^2$f1), and a moiety of Formula ($A^2$f2); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; each $X^2$ is selected from a covalent bond, —O—, —$SO_2$—, —$SO_2$N—, —C(O)—, —C(O)O—, and —C(O)N—; each $R^1$ and $R^2$ is independently selected from hydrogen and methyl; D is selected from a therapeutic agent having at least one primary amine group and a therapeutic agent having at least one secondary amine group; and n6 is selected from 1 to 5.

In certain embodiments of a compound of Formula (III), Q is an MPEG having a number average molecular weight from about 10,000 to 60,000 daltons; each Y is a covalent bond; each $A^2$ is a moiety of Formula ($A^2$a1); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; each $X^2$ is selected from a covalent bond, —O—, —$SO_2$—, —$SO_2$N—, —C(O)—, —C(O)O—, and —C(O)N—; each $R^1$ and $R^2$ is independently selected from hydrogen and methyl; each D is selected from a therapeutic agent having at least one primary amine group and a therapeutic agent having at least one secondary amine group; and n6 is selected from 1 to 5.

In certain embodiments of a compound of Formula (III), Q is an MPEG having a number average molecular weight from about 10,000 to 60,000 daltons; each Y is a covalent bond; each $A^2$ is a moiety of Formula ($A^2$a1), wherein each $R^8$ and $R^9$ is hydrogen; each $X^1$ is pentane-1,5-diyl; each $X^2$ is a covalent bond; each $X^3$ is a covalent bond; each $R^1$ and $R^2$ is hydrogen; each D is independently selected from a therapeutic agent having at least one primary amine group and a therapeutic agent having at least one secondary amine group; and n6 is selected from 1 to 4.

In certain embodiments of a compound of Formula (III), Q is an MPEG having a number average molecular weight from about 10,000 to 60,000 daltons; each Y is a covalent bond; each $A^2$ is a moiety of Formula ($A^2$a1), wherein each $R^8$ and $R^9$ is hydrogen; each $X^1$ is 4-methylcyclohexane-diyl; each $X^2$ is a covalent bond; each $X^3$ is a covalent bond; each $R^1$ and $R^2$ is hydrogen; each D is selected from a therapeutic agent having at least one primary amine group and a therapeutic agent having at least one secondary amine group; and n6 is selected from 1 to 4.

In certain embodiments of a compound of Formula (III), Q is an MPEG having a number average molecular weight from about 10,000 to 60,000 daltons; each Y is a covalent bond; each $A^2$ is a moiety of Formula ($A^2$a1), wherein each $R^8$ and $R^9$ is hydrogen; each $X^1$ is pentane-1,5-diyl; each $X^2$ is —C(O)N—; each $X^3$ is pentane-1,5-diyl; each $R^1$ and $R^2$ is hydrogen; each D is selected from a therapeutic agent having at least one primary amine group and a therapeutic agent having at least one secondary amine group; and n6 is selected from 1 to 4.

In certain embodiments of a compound of Formula (III), Q is an MPEG having a number average molecular weight from about 10,000 to 60,000 daltons; each Y is a covalent bond; each $A^2$ is a moiety of Formula ($A^2$f1); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each $X^2$ is selected from a covalent bond, —O—, —SO$_2$—, —SO$_2$N—, —C(O)—, —C(O)O—, and —C(O)N—; each $R^1$ and $R^2$ is independently selected from hydrogen and methyl; each D is selected from a therapeutic agent having at least one primary amine group and a therapeutic agent having at least one secondary amine group; and n6 is selected from 1 to 5.

In certain embodiments of a compound of Formula (III), Q is an MPEG having a number average molecular weight from about 10,000 to 60,000 daltons; each Y is a covalent bond; each $A^2$ is a moiety of Formula ($A^2$f1); each $X^1$ is pentane-1,5-diyl; each $X^2$ is a covalent bond; each $X^3$ is a covalent bond; each $R^1$ and $R^2$ is hydrogen; each D is independently selected from a therapeutic agent having at least one primary amine group and a therapeutic agent having at least one secondary amine group; and n6 is selected from 1 to 4.

In certain embodiments of a compound of Formula (III), Q is an MPEG having a number average molecular weight from about 10,000 to 60,000 daltons; each Y is a covalent bond; each $A^2$ is a moiety of Formula ($A^2$f1); each $X^1$ is 4-methyl-cyclohexane-diyl; each $X^2$ is a covalent bond; each $X^3$ is a covalent bond; each $R^1$ and $R^2$ is hydrogen; each D is selected from a therapeutic agent having at least one primary amine group and a therapeutic agent having at least one secondary amine group; and n6 is selected from 1 to 4.

In certain embodiments of a compound of Formula (III), Q is an MPEG having a number average molecular weight from about 10,000 to 60,000 daltons; each Y is a covalent bond; each $A^2$ is a moiety of Formula ($A^2$f1); each $X^1$ is pentane-1,5-diyl; each $X^2$ is —C(O)N—; each $X^3$ is pentane-1,5-diyl; each $R^1$ and $R^2$ is hydrogen; each D is selected from a therapeutic agent having at least one primary amine group and a therapeutic agent having at least one secondary amine group; and n6 is selected from 1 to 4.

In certain embodiments of a compound of Formula (III), Q is an MPEG having a number average molecular weight from about 10,000 to 60,000 daltons; each Y is a covalent bond; each $A^2$ is a moiety of Formula ($A^2$f2); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each $X^2$ is selected from a covalent bond, —O—, —SO$_2$—, —SO$_2$N—, —C(O)—, —C(O)O—, and —C(O)N—; each $R^1$ and $R^2$ is independently selected from hydrogen and methyl; each D is selected from a therapeutic agent having at least one primary amine group and a therapeutic agent having at least one secondary amine group; and n6 is selected from 1 to 5.

In certain embodiments of a compound of Formula (III), Q is an MPEG having a number average molecular weight from about 10,000 to 60,000 daltons; each Y is a covalent bond; each $A^2$ is a moiety of Formula ($A^2$f2); each $X^1$ is methane-diyl; each $X^2$ is a covalent bond; each $X^3$ is a covalent bond; each $R^1$ and $R^2$ is hydrogen; each D is independently selected from a therapeutic agent having at least one primary amine group and a therapeutic agent having at least one secondary amine group; and n6 is selected from 1 to 4.

In certain embodiments of a compound of Formula (III), Q is an MPEG having a number average molecular weight from about 10,000 to 60,000 daltons; each Y is a covalent bond; each $A^2$ is a moiety of Formula ($A^2$f2); each $X^1$ is methane-diyl; each $X^2$ is —C(O)N—; each $X^3$ is pentane-1,5-diyl; each $R^1$ and $R^2$ is hydrogen; each D is selected from a therapeutic agent having at least one primary amine group and a therapeutic agent having at least one secondary amine group; and n6 is selected from 1 to 4.

In certain embodiments of a compound of Formula (III), Q is an avidin; each Y is a hydrogen bond; each $A^2$ is independently selected from a moiety of Formula ($A^2$c1), a moiety of Formula ($A^2$c2), and a moiety of Formula ($A^2$c3); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each $X^2$ is selected from a covalent bond, —O—, —SO$_2$—, —SO$_2$N—, —C(O)—, —C(O)O—, and —C(O)N—; each $R^1$ and $R^2$ is independently selected from hydrogen and methyl; each D is selected from a therapeutic agent having at least one primary amine group and a therapeutic agent having at least one secondary amine group; and n6 is selected from 1 to 4.

In certain embodiments of a compound of Formula (III), Q is an avidin; each Y is a hydrogen bond; each $A^2$ is independently selected from a moiety of Formula ($A^2$c1), a moiety of Formula ($A^2$c2), and a moiety of Formula ($A^2$c3); each $X^1$ is butane-1,4-diyl; each $X^2$ is selected from a covalent bond and —C(O)N—; each $X^3$ is selected from a covalent bond, pentane-1,5-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 10; each $R^1$ and $R^2$ is hydrogen; each D is independently selected from a therapeutic agent having at least one primary amine group and a therapeutic agent having at least one secondary amine group; and n6 is selected from 1 to 4.

In certain embodiments of a compound of Formula (III), Q is an avidin; each Y is a hydrogen bond; each $A^2$ is a moiety of Formula ($A^2$c1); each $X^1$ is butane-1,4-diyl; each $X^2$ is —C(O)N—; each $X^3$ is pentane-1,5-diyl; each $R^1$ and $R^2$ is hydrogen; each D is independently selected from a therapeutic agent having at least one primary amine group and a therapeutic agent having at least one secondary amine group; and n6 is selected from 1 to 4.

In certain embodiments of a compound of Formula (III), Q is an avidin; each Y is a hydrogen bond; each $A^2$ is a moiety of Formula ($A^2$c2); each $X^1$ is butane-1,4-diyl; each $X^2$ is —C(O)N—; each $X^3$ is pentane-1,5-diyl; each $R^1$ and $R^2$ is hydrogen; each D is independently selected from a therapeutic agent having at least one primary amine group and a therapeutic agent having at least one secondary amine group; and n6 is selected from 1 to 4.

In certain embodiments of a compound of Formula (III), Q is an avidin; each Y is a hydrogen bond; each $A^2$ is a moiety of Formula ($A^2$c3); each $X^1$ is butane-1,4-diyl; each $X^2$ is —C(O)N—; each $X^3$ is pentane-1,5-diyl; each $R^1$ and $R^2$ is hydrogen; each D is independently selected from a therapeutic agent having at least one primary amine group and a therapeutic agent having at least one secondary amine group; and n6 is selected from 1 to 4.

In certain embodiments of a compound of Formula (III), Q is a human serum albumin; each Y is a covalent bond; each $A^2$ is independently selected from a covalent bond, —C(O)N—, —SO$_2$—, —S—, a moiety of Formula ($A^2$a1), a moiety of Formula ($A^2$f1), and a moiety of Formula ($A^2$f2); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each $X^2$ is selected from a covalent bond, —O—, —SO$_2$—, —SO$_2$N—, —C(O)—, —C(O)O—, and —C(O)N—; each $R^1$ and $R^2$ is independently selected from hydrogen and methyl; each D is selected from a therapeutic agent having at least one primary amine group and a therapeutic agent having at least one secondary amine group; and n6 is 1.

In certain embodiments of a compound of Formula (III), Q is a human serum albumin; each Y is a covalent bond; each $A^2$ is a moiety of Formula ($A^2$a1); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each $X^2$ is selected from a covalent bond, —O—, —SO$_2$—, —SO$_2$N—, —C(O)—, —C(O)O—, and —C(O)N—; each $R^1$ and $R^2$ is independently selected from hydrogen and methyl; each D is selected from a therapeutic agent having at least one primary amine group and a therapeutic agent having at least one secondary amine group; and n6 is 1.

In certain embodiments of a compound of Formula (III), Q is a human serum albumin; each Y is a covalent bond; each $A^2$ is a moiety of Formula ($A^2$a1), wherein each $R^8$ and $R^9$ is hydrogen; each $X^1$ is pentane-1,5-diyl; each $X^2$ is a covalent bond; each $X^3$ is a covalent bond; each $R^1$ and $R^2$ is hydrogen; each D is independently selected from a therapeutic agent having at least one primary amine group and a therapeutic agent having at least one secondary amine group; and n6 is 1.

In certain embodiments of a compound of Formula (III), Q is a human serum albumin; each Y is a covalent bond; each $A^2$ is a moiety of Formula ($A^2$a1), wherein each $R^8$ and $R^9$ is hydrogen; each $X^1$ is 4-methylcyclohexane-diyl; each $X^2$ is a covalent bond; each $X^3$ is a covalent bond; each $R^1$ and $R^2$ is hydrogen; each D is selected from a therapeutic agent having at least one primary amine group and a therapeutic agent having at least one secondary amine group; and n6 is 1.

In certain embodiments of a compound of Formula (III), Q is a human serum albumin; each Y is a covalent bond; each $A^2$ is a moiety of Formula ($A^2$a1), wherein each $R^8$ and $R^9$ is hydrogen; each $X^1$ is pentane-1,5-diyl; each $X^2$ is —C(O)N—; each $X^3$ is pentane-1,5-diyl; each $R^1$ and $R^2$ is hydrogen; each D is selected from a therapeutic agent having at least one primary amine group and a therapeutic agent having at least one secondary amine group; and n6 is 1.

In certain embodiments of a compound of Formula (III), Q is a human serum albumin; each Y is a covalent bond; each $A^2$ is a moiety of Formula ($A^2$f1); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each $X^2$ is selected from a covalent bond, —O—, —SO$_2$—, —SO$_2$N—, —C(O)—, —C(O)O—, and —C(O)N—; each $R^1$ and $R^2$ is independently selected from hydrogen and methyl; each D is selected from a therapeutic agent having at least one primary amine group and a therapeutic agent having at least one secondary amine group; and n6 is 1.

In certain embodiments of a compound of Formula (III), Q is a human serum albumin; each Y is a covalent bond; each $A^2$ is a moiety of Formula ($A^2$f1); each $X^1$ is pentane-1,5-diyl; each $X^2$ is a covalent bond; each $X^3$ is a covalent bond; each $R^1$ and $R^2$ is hydrogen; each D is independently selected from a therapeutic agent having at least one primary amine group and a therapeutic agent having at least one secondary amine group; and n6 is 1.

In certain embodiments of a compound of Formula (III), Q is a human serum albumin; each Y is a covalent bond; each $A^2$ is a moiety of Formula ($A^2$f1); each $X^1$ is 4-methylcyclohexane-diyl; each $X^2$ is a covalent bond; each $X^3$ is a covalent bond; each $R^1$ and $R^2$ is hydrogen; each D is selected from a therapeutic agent having at least one primary amine group and a therapeutic agent having at least one secondary amine group; and n6 is 1.

In certain embodiments of a compound of Formula (III), Q is a human serum albumin; each Y is a covalent bond; each $A^2$ is a moiety of Formula ($A^2$f1); each $X^1$ is pentane-1,5-diyl; each $X^2$ is —C(O)N—; each $X^3$ is pentane-1,5-diyl; each $R^1$ and $R^2$ is hydrogen; each D is selected from a therapeutic agent having at least one primary amine group and a therapeutic agent having at least one secondary amine group; and n6 is 1.

In certain embodiments of a compound of Formula (III), Q is an antibody; each Y is a covalent bond; each $A^2$ is independently selected from a covalent bond, —C(O)N—, —SO$_2$—, —S—, a moiety of Formula ($A^2$a1), a moiety of Formula ($A^2$f1), and a moiety of Formula ($A^2$f2); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each $X^2$ is selected from a covalent bond, —O—, —SO$_2$—, —SO$_2$N—, —C(O)—, —C(O)O—, and —C(O)N—; each $R^1$ and $R^2$ is independently selected from hydrogen and methyl; each D is selected from a therapeutic agent having at least one primary amine group and a therapeutic agent having at least one secondary amine group; and n6 is selected from 1 to 5.

In certain embodiments of a compound of Formula (III), Q is an antibody; each Y is a covalent bond; each $A^2$ is a moiety of Formula ($A^2$a1); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each $X^2$ is selected from a covalent bond, —O—, —SO$_2$—, —SO$_2$N—, —C(O)—, —C(O)O—, and —C(O)N—; each $R^1$ and $R^2$ is independently selected from hydrogen and methyl; each D is selected from a therapeutic agent having at least one primary amine group and a therapeutic agent having at least one secondary amine group; and n6 is selected from 1 to 5.

In certain embodiments of a compound of Formula (III), Q is an antibody; each Y is a covalent bond; each $A^2$ is a moiety of Formula ($A^2$a1), wherein each $R^8$ and $R^9$ is hydrogen; each $X^1$ is pentane-1,5-diyl; each $X^2$ is a covalent bond; each $X^3$ is a covalent bond; each $R^1$ and $R^2$ is hydrogen; each D is independently selected from a therapeutic agent having at least one primary amine group and a therapeutic agent having at least one secondary amine group; and n6 is selected from 1 to 5.

In certain embodiments of a compound of Formula (III), Q is an antibody; each Y is a covalent bond; each $A^2$ is a moiety of Formula ($A^2$a1), wherein each $R^8$ and $R^9$ is hydrogen; each $X^1$ is 4-methylcyclohexane-diyl; each $X^2$ is a covalent bond; each $X^3$ is a covalent bond; each $R^1$ and $R^2$ is hydrogen; each D is selected from a therapeutic agent having at least one primary amine group and a therapeutic agent having at least one secondary amine group; and n6 is selected from 1 to 5.

In certain embodiments of a compound of Formula (III), Q is an antibody; each Y is a covalent bond; each $A^2$ is a moiety of Formula ($A^2$a1), wherein each $R^8$ and $R^9$ is hydrogen; each $X^1$ is pentane-1,5-diyl; each $X^2$ is —C(O)N—; each $X^3$ is pentane-1,5-diyl; each $R^1$ and $R^2$ is hydrogen; each D is selected from a therapeutic agent having at least one primary amine group and a therapeutic agent having at least one secondary amine group; and n6 is selected from 1 to 5.

In certain embodiments of a compound of Formula (III), Q is an antibody; each Y is a covalent bond; each $A^2$ is a moiety of Formula ($A^2$f1); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each $X^2$ is selected from a covalent bond, —O—, —SO$_2$—, —SO$_2$N—, —C(O)—, —C(O)O—, and —C(O)N—; each $R^1$ and $R^2$ is independently selected from hydrogen and methyl; each D is selected from a therapeutic agent having at least one primary amine group and a therapeutic agent having at least one secondary amine group; and n6 is selected from 1 to 5.

In certain embodiments of a compound of Formula (III), Q is an antibody; each Y is a covalent bond; each $A^2$ is a moiety of Formula ($A^2$f1); each $X^1$ is pentane-1,5-diyl; each $X^2$ is a covalent bond; each $X^3$ is a covalent bond; each $R^1$ and $R^2$ is hydrogen; each D is independently selected from a therapeutic agent having at least one primary amine group and a therapeutic agent having at least one secondary amine group; and n6 is selected from 1 to 5.

In certain embodiments of a compound of Formula (III), Q is an antibody; each Y is a covalent bond; each $A^2$ is a moiety of Formula ($A^2$f1); each $X^1$ is 4-methylcyclohexane-diyl; each $X^2$ is a covalent bond; each $X^3$ is a covalent bond; each $R^1$ and $R^2$ is hydrogen; each D is selected from a therapeutic agent having at least one primary amine group and a therapeutic agent having at least one secondary amine group; and n6 is selected from 1 to 5.

In certain embodiments of a compound of Formula (III), Q is an antibody; each Y is a covalent bond; each $A^2$ is a moiety of Formula ($A^2$f1); each $X^1$ is pentane-1,5-diyl; each $X^2$ is —C(O)N—; each $X^3$ is pentane-1,5-diyl; each $R^1$ and $R^2$ is hydrogen; each D is selected from a therapeutic agent having at least one primary amine group and a therapeutic agent having at least one secondary amine group; and n6 is selected from 1 to 5.

In certain embodiments of a compound of Formula (III), Q is an antibody; each Y is a covalent bond; each $A^2$ is a moiety of Formula ($A^2$f2); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each $X^2$ is selected from a covalent bond, —O—, —SO$_2$—, —SO$_2$N—, —C(O)—, —C(O)O—, and —C(O)N—; each $R^1$ and $R^2$ is independently selected from hydrogen and methyl; each D is selected from a therapeutic agent having at least one primary amine group and a therapeutic agent having at least one secondary amine group; and n6 is selected from 1 to 5.

In certain embodiments of a compound of Formula (III), Q is an antibody; each Y is a covalent bond; each $A^2$ is a moiety of Formula ($A^2$f2); each $X^1$ is methane-diyl; each $X^2$ is a covalent bond; each $X^3$ is a covalent bond; each $R^1$ and $R^2$ is hydrogen; each D is independently selected from a therapeutic agent having at least one primary amine group and a therapeutic agent having at least one secondary amine group; and n6 is selected from 1 to 5.

In certain embodiments of a compound of Formula (III), Q is an antibody; each Y is a covalent bond; each $A^2$ is a moiety of Formula ($A^2$f2); each $X^1$ is methane-diyl; each $X^2$ is —C(O)N—; each $X^3$ is pentane-1,5-diyl; each $R^1$ and $R^2$ is hydrogen; each D is selected from a therapeutic agent having at least one primary amine group and a therapeutic agent having at least one secondary amine group; and n6 is selected from 1 to 5.

In certain embodiments of a compound of Formula (III), Q is a polystyrene; each Y is a covalent bond; each $A^2$ is independently selected from a covalent bond, —C(O)N—, —SO$_2$—, —S—, a moiety of Formula ($A^2$a1), a moiety of Formula ($A^2$f1), and a moiety of Formula ($A^2$f2); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8- diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each X$^2$ is selected from a covalent bond, —O—, —SO$_2$—, —SO$_2$N—, —C(O)—, —C(O)O—, and —C(O)N—; each R$^1$ and R$^2$ is independently selected from hydrogen and methyl; each D is selected from a therapeutic agent having at least one primary amine group and a therapeutic agent having at least one secondary amine group; and n6 is selected from 1 to 20.

In certain embodiments of a compound of Formula (III), Q is a polystyrene; each Y is a covalent bond; each A$^2$ is a moiety of Formula (A$^2$a1); each X$^1$ and X$^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each X$^2$ is selected from a covalent bond, —O—, —SO$_2$—, —SO$_2$N—, —C(O)—, —C(O)O—, and —C(O)N—; each R$^1$ and R$^2$ is independently selected from hydrogen and methyl; each D is selected from a therapeutic agent having at least one primary amine group and a therapeutic agent having at least one secondary amine group; and n6 is selected from 1 to 20.

In certain embodiments of a compound of Formula (III), Q is a polystyrene; each Y is a covalent bond; each A$^2$ is a moiety of Formula (A$^2$a1), wherein each R$^8$ and R$^9$ is hydrogen; each X$^1$ is pentane-1,5-diyl; each X$^2$ is a covalent bond; each X$^3$ is a covalent bond; each R$^1$ and R$^2$ is hydrogen; each D is independently selected from a therapeutic agent having at least one primary amine group and a therapeutic agent having at least one secondary amine group; and n6 is selected from 1 to 20.

In certain embodiments of a compound of Formula (III), Q is a polystyrene; each Y is a covalent bond; each A$^2$ is a moiety of Formula (A$^2$a1), wherein each R$^8$ and R$^9$ is hydrogen; each X$^1$ is 4-methylcyclohexane-diyl; each X$^2$ is a covalent bond; each X$^3$ is a covalent bond; each R$^1$ and R$^2$ is hydrogen; each D is selected from a therapeutic agent having at least one primary amine group and a therapeutic agent having at least one secondary amine group; and n6 is selected from 1 to 20.

In certain embodiments of a compound of Formula (III), Q is a polystyrene; each Y is a covalent bond; each A$^2$ is a moiety of Formula (A$^2$a1), wherein each R$^8$ and R$^9$ is hydrogen; each X$^1$ is pentane-1,5-diyl; each X$^2$ is —C(O)N—; each X$^3$ is pentane-1,5-diyl; each R$^1$ and R$^2$ is hydrogen; each D is selected from a therapeutic agent having at least one primary amine group and a therapeutic agent having at least one secondary amine group; and n6 is selected from 1 to 20.

In certain embodiments of a compound of Formula (III), Q is a polystyrene; each Y is a covalent bond; each A$^2$ is a moiety of Formula (A$^2$f1); each X$^1$ and X$^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each X$^2$ is selected from a covalent bond, —O—, —SO$_2$—, —SO$_2$N—, —C(O)—, —C(O)O—, and —C(O)N—; each R$^1$ and R$^2$ is independently selected from hydrogen and methyl; each D is selected from a therapeutic agent having at least one primary amine group and a therapeutic agent having at least one secondary amine group; and n6 is selected from 1 to 20.

In certain embodiments of a compound of Formula (III), Q is a polystyrene; each Y is a covalent bond; each A$^2$ is a moiety of Formula (A$^2$f1); each X$^1$ is pentane-1,5-diyl; each X$^2$ is a covalent bond; each X$^3$ is a covalent bond; each R$^1$ and R$^2$ is hydrogen; each D is independently selected from a therapeutic agent having at least one primary amine group and a therapeutic agent having at least one secondary amine group; and n6 is selected from 1 to 20.

In certain embodiments of a compound of Formula (III), Q is a polystyrene; each Y is a covalent bond; each A$^2$ is a moiety of Formula (A$^2$f1); each X$^1$ is 4-methylcyclohexane-diyl; each X$^2$ is a covalent bond; each X$^3$ is a covalent bond; each R$^1$ and R$^2$ is hydrogen; each D is selected from a therapeutic agent having at least one primary amine group and a therapeutic agent having at least one secondary amine group; and n6 is selected from 1 to 20.

In certain embodiments of a compound of Formula (III), Q is a polystyrene; each Y is a covalent bond; each A$^2$ is a moiety of Formula (A$^2$f1); each X$^1$ is pentane-1,5-diyl; each X$^2$ is —C(O)N—; each X$^3$ is pentane-1,5-diyl; each R$^1$ and R$^2$ is hydrogen; each D is selected from a therapeutic agent having at least one primary amine group and a therapeutic agent having at least one secondary amine group; and n6 is selected from 1 to 20.

In certain embodiments of a compound of Formula (III), Q is a polystyrene; each Y is a covalent bond; each A$^2$ is a moiety of Formula (A$^2$f2); each X$^1$ and X$^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; each X$^2$ is selected from a covalent bond, —O—, —SO$_2$—, —SO$_2$N—, —C(O)—, —C(O)O—, and —C(O)N—; each R$^1$ and R$^2$ is independently selected from hydrogen and methyl; each D is selected from a therapeutic agent having at least one primary amine group and a therapeutic agent having at least one secondary amine group; and n6 is selected from 1 to 20.

In certain embodiments of a compound of Formula (III), Q is a polystyrene; each Y is a covalent bond; each A$^2$ is a moiety of Formula (A$^2$f2); each X$^1$ is methane-diyl; each X$^2$ is a covalent bond; each X$^3$ is a covalent bond; each R$^1$ and R$^2$ is hydrogen; each D is independently selected from a therapeutic agent having at least one primary amine group and a therapeutic agent having at least one secondary amine group; and n6 is selected from 1 to 20.

In certain embodiments of a compound of Formula (III), Q is a polystyrene; each Y is a covalent bond; each A$^2$ is a moiety of Formula (A$^2$f2); each X$^1$ is methane-diyl; each X$^2$ is —C(O)N—; each X$^3$ is pentane-1,5-diyl; each R$^1$ and R$^2$ is hydrogen; each D is selected from a therapeutic agent having at least one primary amine group and a therapeutic agent having at least one secondary amine group; and n6 is selected from 1 to 20.

In certain embodiments of a compound of Formula (III), Q is a glass ($SiO_2$) substrate; each Y is a covalent bond; each $A^2$ is independently selected from a covalent bond, —C(O)N—, —$SO_2$—, —S—, a moiety of Formula ($A^2a1$), a moiety of Formula ($A^2f1$), and a moiety of Formula ($A^2f2$); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; each $X^2$ is selected from a covalent bond, —O—, —$SO_2$—, —$SO_2$N—, —C(O)—, —C(O)O—, and —C(O)N—; each $R^1$ and $R^2$ is independently selected from hydrogen and methyl; each D is selected from a therapeutic agent having at least one primary amine group and a therapeutic agent having at least one secondary amine group; and n6 is selected from 1 to 20.

In certain embodiments of a compound of Formula (III), Q is a glass ($SiO_2$) substrate; each Y is a covalent bond; each $A^2$ is a moiety of Formula ($A^2a1$); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; each $X^2$ is selected from a covalent bond, —O—, —$SO_2$—, —$SO_2$N—, —C(O)—, —C(O)O—, and —C(O)N—; each $R^1$ and $R^2$ is independently selected from hydrogen and methyl; each D is selected from a therapeutic agent having at least one primary amine group and a therapeutic agent having at least one secondary amine group; and n6 is selected from 1 to 20.

In certain embodiments of a compound of Formula (III), Q is a glass ($SiO_2$) substrate; each Y is a covalent bond; each $A^2$ is a moiety of Formula ($A^2a1$), wherein each $R^8$ and $R^9$ is hydrogen; each $X^1$ is pentane-1,5-diyl; each $X^2$ is a covalent bond; each $X^3$ is a covalent bond; each $R^1$ and $R^2$ is hydrogen; each D is independently selected from a therapeutic agent having at least one primary amine group and a therapeutic agent having at least one secondary amine group; and n6 is selected from 1 to 20.

In certain embodiments of a compound of Formula (III), Q is a glass ($SiO_2$) substrate; each Y is a covalent bond; each $A^2$ is a moiety of Formula ($A^2a1$), wherein each $R^8$ and $R^9$ is hydrogen; each $X^1$ is 4-methylcyclohexane-diyl; each $X^2$ is a covalent bond; each $X^3$ is a covalent bond; each $R^1$ and $R^2$ is hydrogen; each D is selected from a therapeutic agent having at least one primary amine group and a therapeutic agent having at least one secondary amine group; and n6 is selected from 1 to 20.

In certain embodiments of a compound of Formula (III), Q is a glass ($SiO_2$) substrate; each Y is a covalent bond; each $A^2$ is a moiety of Formula ($A^2a1$), wherein each $R^8$ and $R^9$ is hydrogen; each $X^1$ is pentane-1,5-diyl; each $X^2$ is —C(O)N—; each $X^3$ is pentane-1,5-diyl; each $R^1$ and $R^2$ is hydrogen; each D is selected from a therapeutic agent having at least one primary amine group and a therapeutic agent having at least one secondary amine group; and n6 is selected from 1 to 20.

In certain embodiments of a compound of Formula (III), Q is a glass ($SiO_2$) substrate; each Y is a covalent bond; each $A^2$ is a moiety of Formula ($A^2f1$); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; each $X^2$ is selected from a covalent bond, —O—, —$SO_2$—, —$SO_2$N—, —C(O)—, —C(O)O—, and —C(O)N—; each $R^1$ and $R^2$ is independently selected from hydrogen and methyl; each D is selected from a therapeutic agent having at least one primary amine group and a therapeutic agent having at least one secondary amine group; and n6 is selected from 1 to 20.

In certain embodiments of a compound of Formula (III), Q is a glass ($SiO_2$) substrate; each Y is a covalent bond; each $A^2$ is a moiety of Formula ($A^2f1$); each $X^1$ is pentane-1,5-diyl; each $X^2$ is a covalent bond; each $X^3$ is a covalent bond; each $R^1$ and $R^2$ is hydrogen; each D is independently selected from a therapeutic agent having at least one primary amine group and a therapeutic agent having at least one secondary amine group; and n6 is selected from 1 to 20.

In certain embodiments of a compound of Formula (III), Q is a glass ($SiO_2$) substrate; each Y is a covalent bond; each $A^2$ is a moiety of Formula ($A^2f1$); each $X^1$ is 4-methylcyclohexane-diyl; each $X^2$ is a covalent bond; each $X^3$ is a covalent bond; each $R^1$ and $R^2$ is hydrogen; each D is selected from a therapeutic agent having at least one primary amine group and a therapeutic agent having at least one secondary amine group; and n6 is selected from 1 to 20.

In certain embodiments of a compound of Formula (III), Q is a glass ($SiO_2$) substrate; each Y is a covalent bond; each $A^2$ is a moiety of Formula ($A^2f1$); each $X^1$ is pentane-1,5-diyl; each $X^2$ is —C(O)N—; each $X^3$ is pentane-1,5-diyl; each $R^1$ and $R^2$ is hydrogen; each D is selected from a therapeutic agent having at least one primary amine group and a therapeutic agent having at least one secondary amine group; and n6 is selected from 1 to 20.

In certain embodiments of a compound of Formula (III), Q is a glass ($SiO_2$) substrate; each Y is a covalent bond; each $A^2$ is a moiety of Formula ($A^2f2$); each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; each $X^2$ is selected from a covalent bond, —O—, —$SO_2$—, —$SO_2$N—, —C(O)—, —C(O)O—, and —C(O)N—; each $R^1$ and $R^2$ is independently selected from hydrogen and methyl; each D is selected from a therapeutic agent having at least one primary amine group and a therapeutic agent having at least one secondary amine group; and n6 is selected from 1 to 20.

In certain embodiments of a compound of Formula (III), Q is a glass (SiO$_2$) substrate; each Y is a covalent bond; each A$^2$ is a moiety of Formula (A$^2$f2); each X$^1$ is methane-diyl; each X$^2$ is a covalent bond; each X$^3$ is a covalent bond; each R$^1$ and R$^2$ is hydrogen; each D is independently selected from a therapeutic agent having at least one primary amine group and a therapeutic agent having at least one secondary amine group; and n6 is selected from 1 to 20.

In certain embodiments of a compound of Formula (III), Q is a glass (SiO$_2$) substrate; each Y is a covalent bond; each A$^2$ is a moiety of Formula (A$^2$f2); each X$^1$ is methane-diyl; each X$^2$ is —C(O)N—; each X$^3$ is pentane-1,5-diyl; each R$^1$ and R$^2$ is hydrogen; each D is selected from a therapeutic agent having at least one primary amine group and a therapeutic agent having at least one secondary amine group; and n6 is selected from 1 to 20.

The compound of claim 48, wherein the compound is selected from a compound of Formula (III-a), Formula (III-b), Formula (III-c), Formula (III-d), Formula (III-e), Formula (III-f), Formula (III-g), Formula (III-h), Formula (III-i), Formula (III-j), Formula (III-k), Formula (III-l), Formula (III-m), Formula (III-n), Formula (III-o), Formula (III-p), Formula (III-q), Formula (III-r), Formula (III-s), Formula (III-t), Formula (III-u), Formula (III-III), Formula (III-w), Formula (III-x), Formula (III-y), Formula (III-z), Formula (III-aa), Formula (III-ab), and Formula (III-ac), or a pharmaceutically acceptable salt of any of the foregoing:

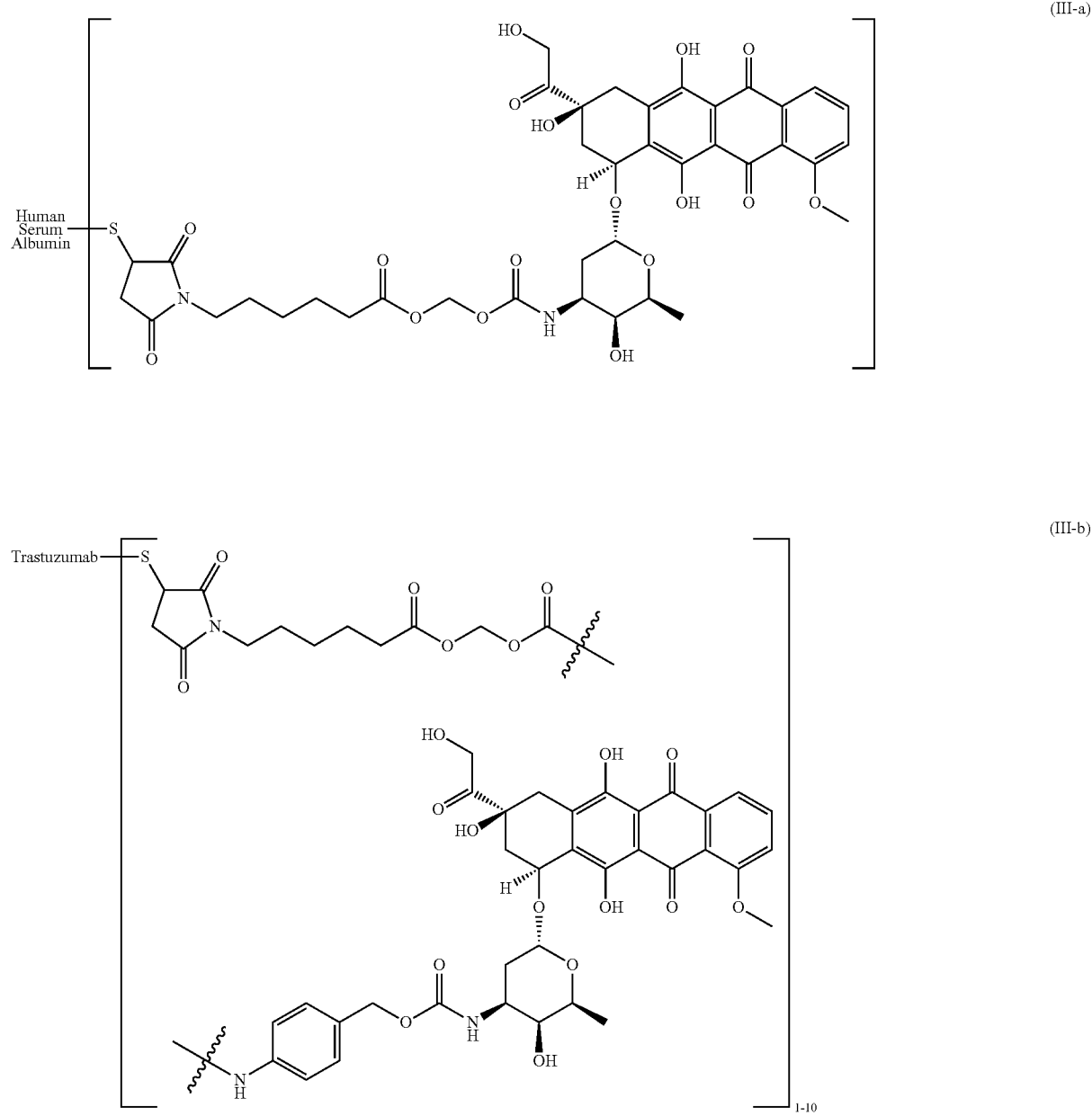

-continued
(III-c)
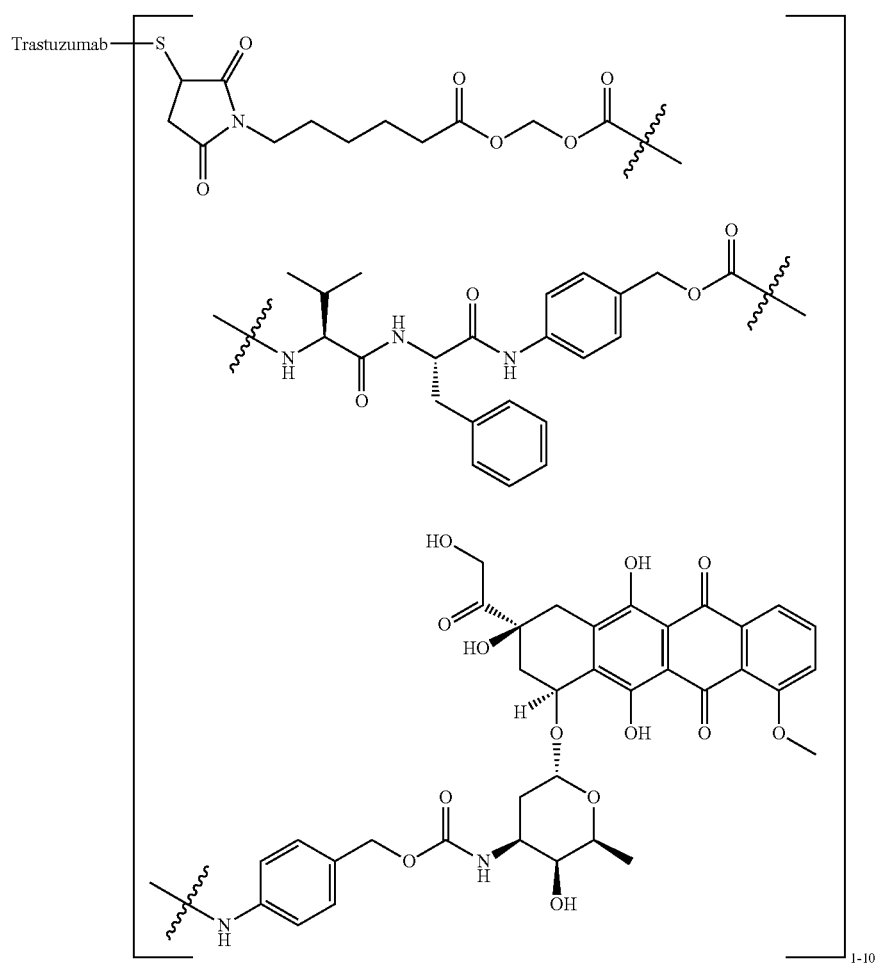
(III-d)
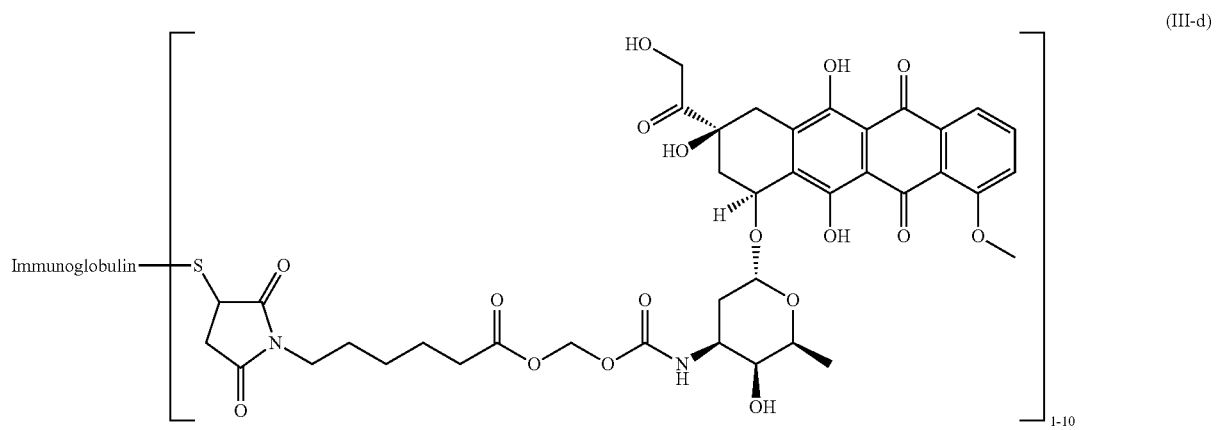

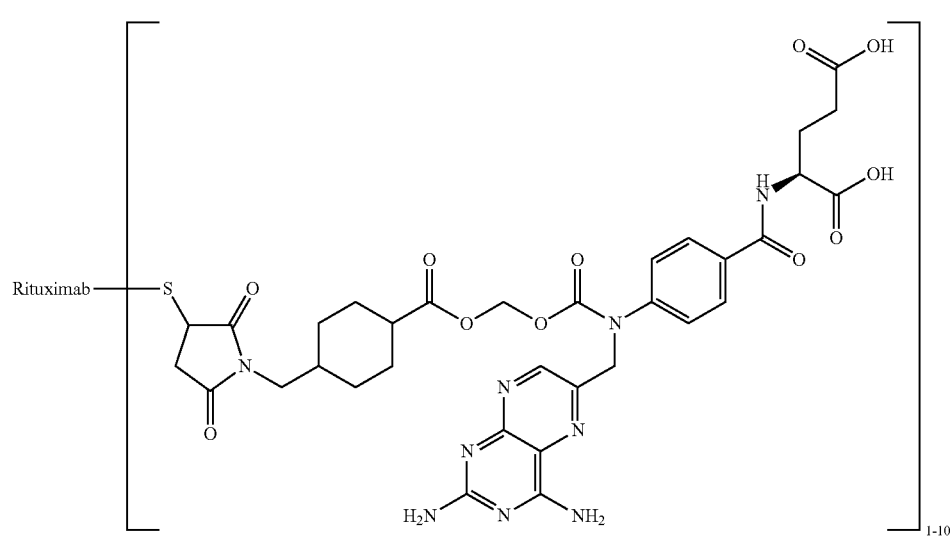
(III-e)
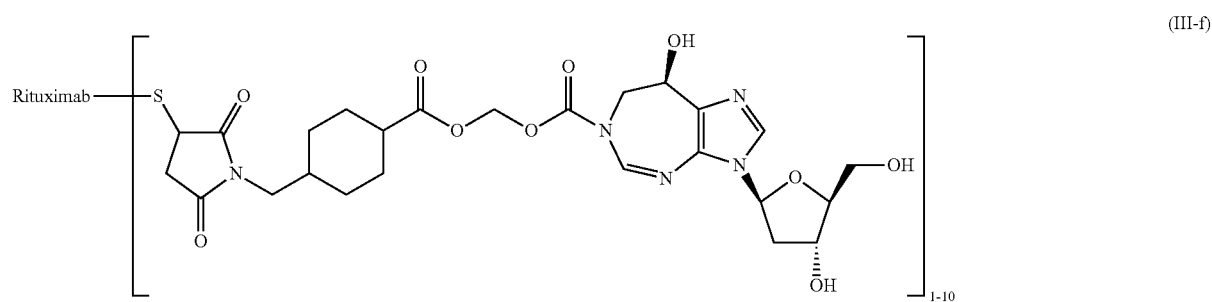
(III-f)
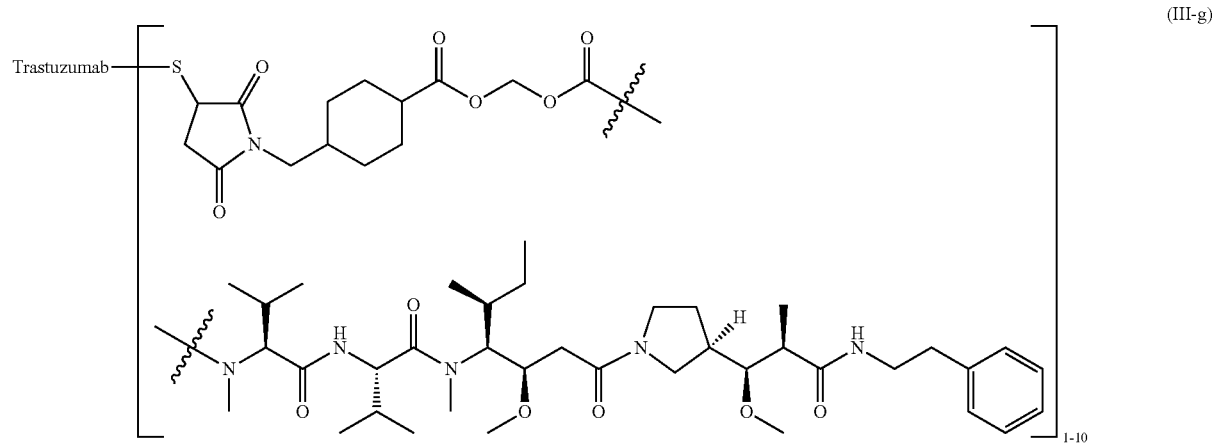
(III-g)

(III-h)
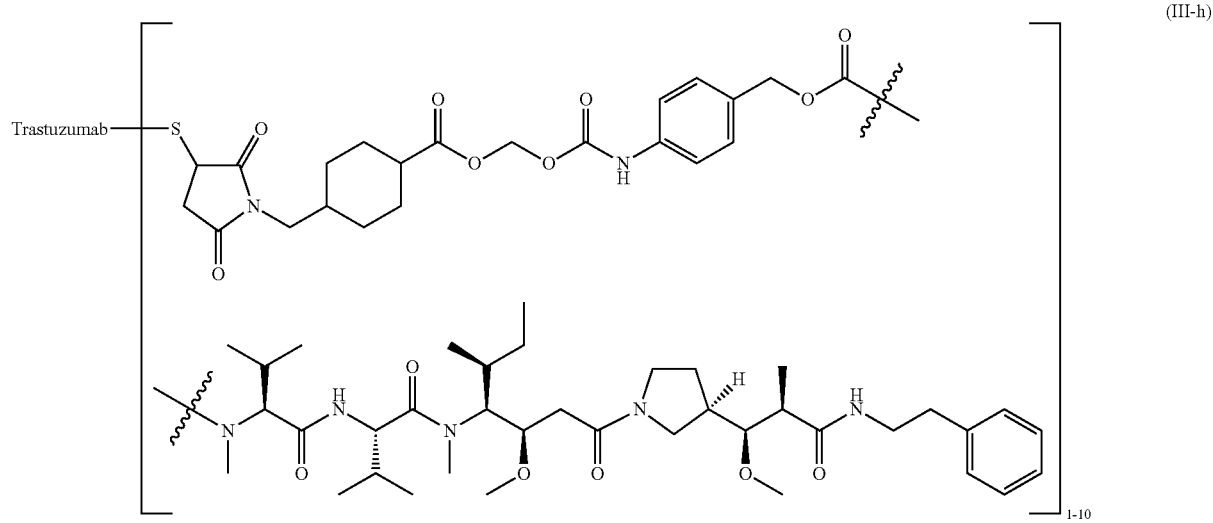
(III-i)
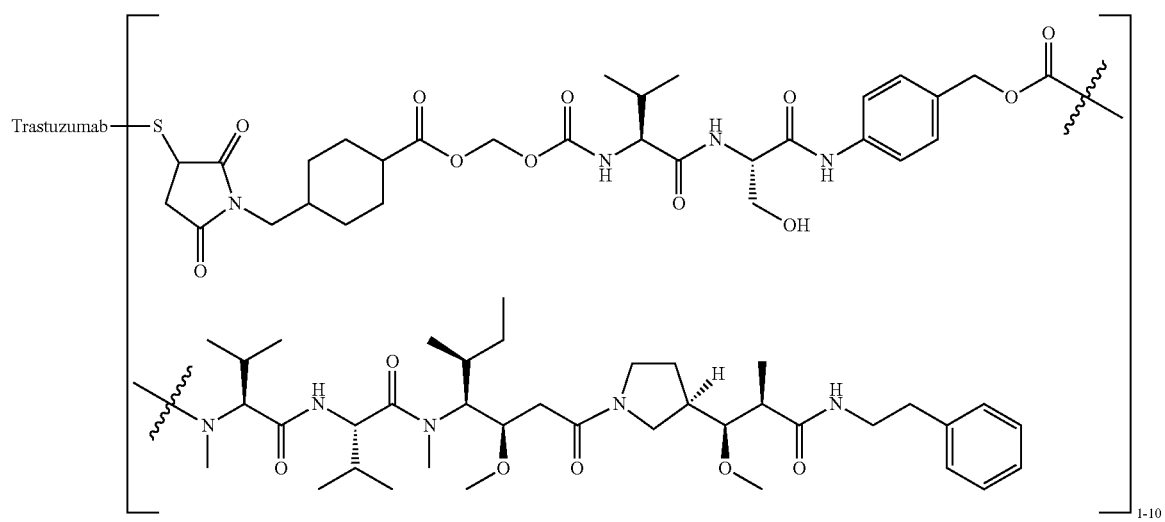
(III-j)
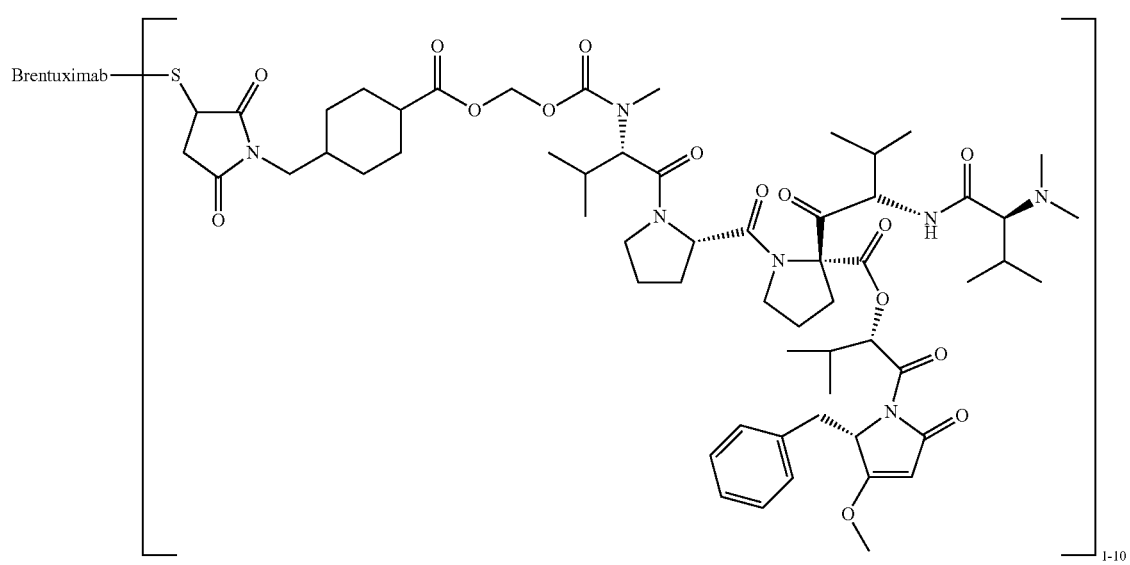

(III-k)
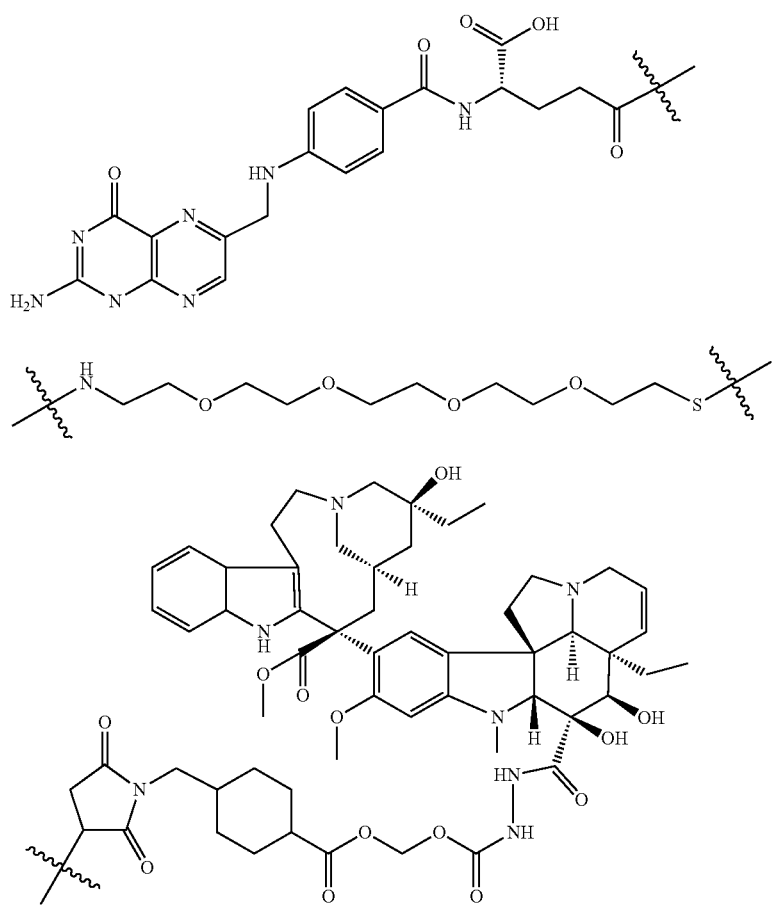
(III-l)
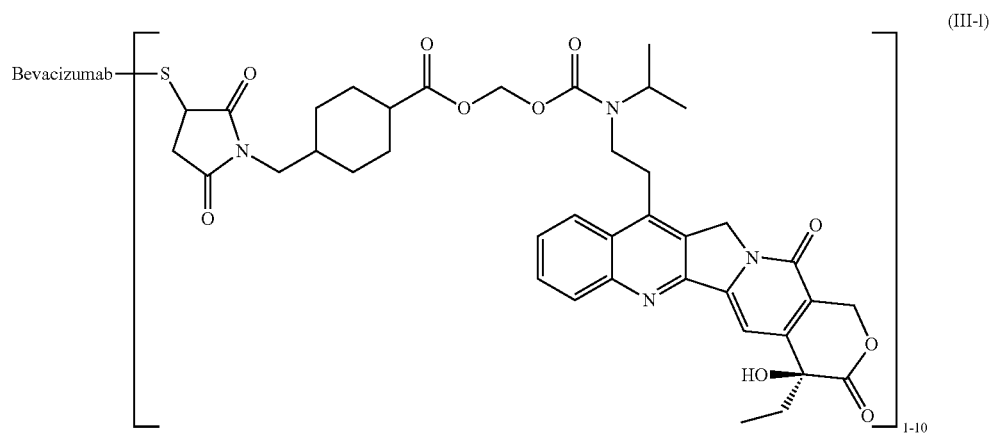

(III-m)
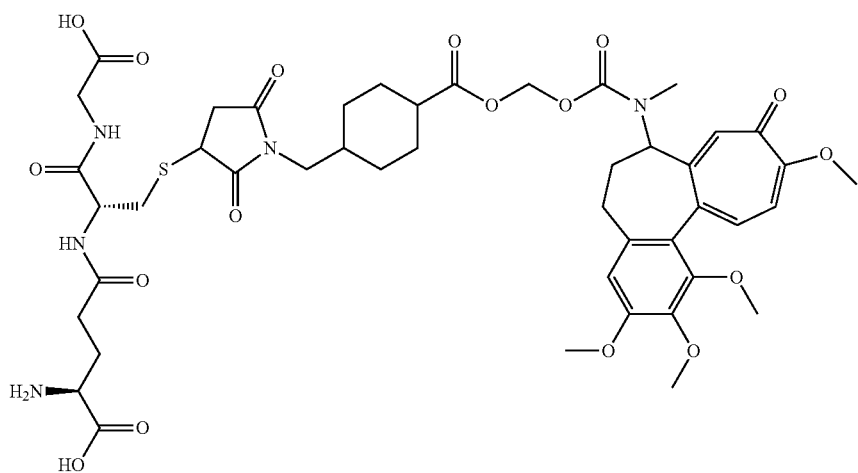
(III-n)
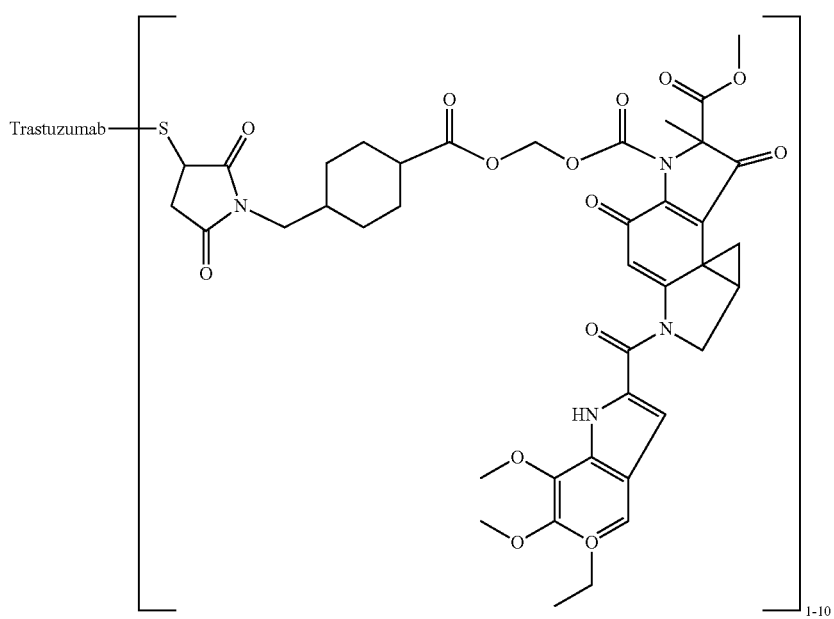
(III-o)
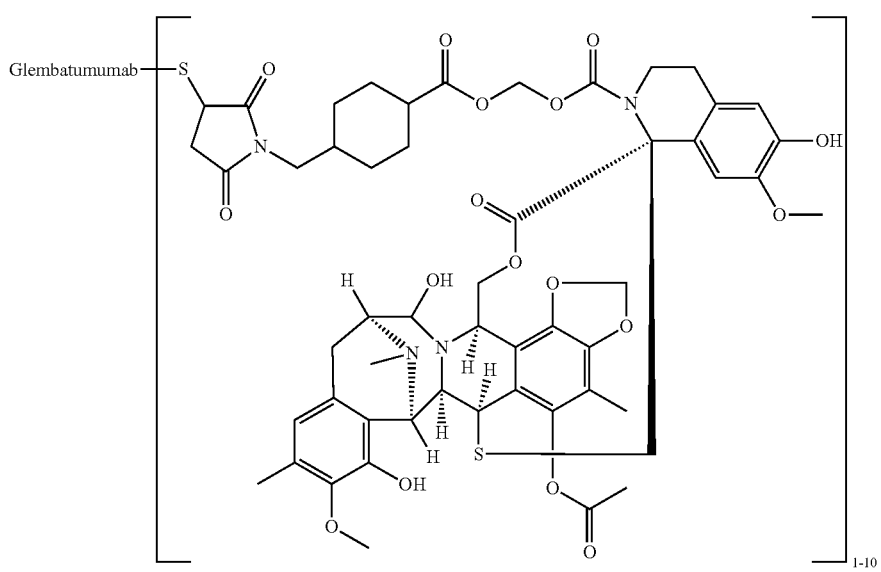

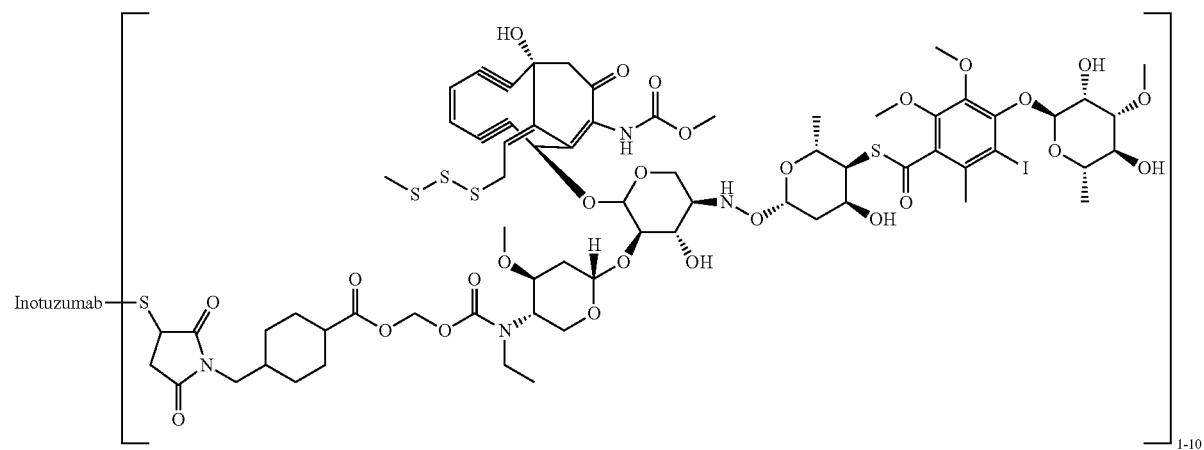
(III-p)
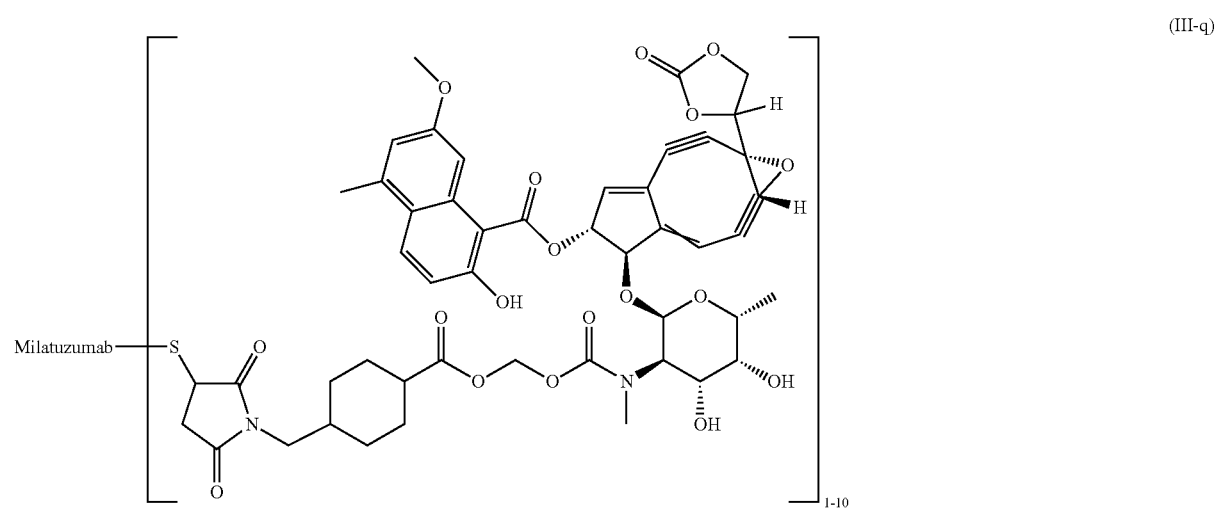
(III-q)
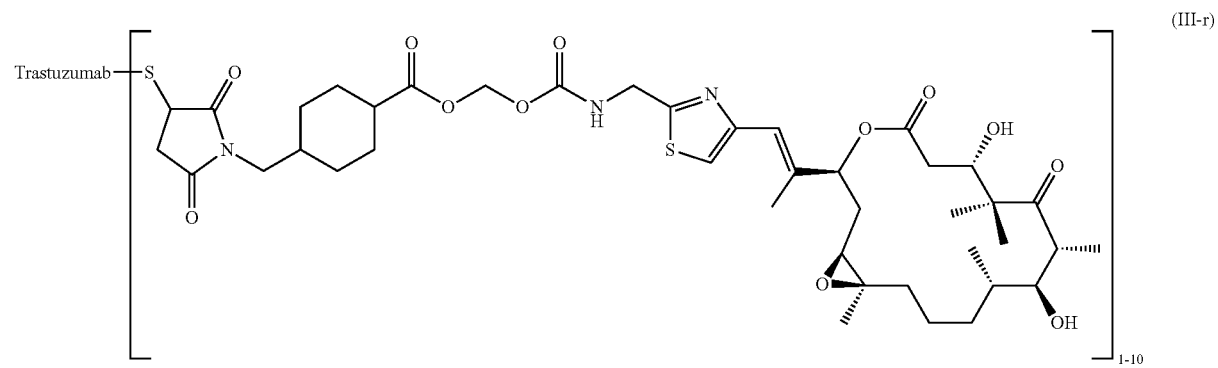
(III-r)

(III-s)
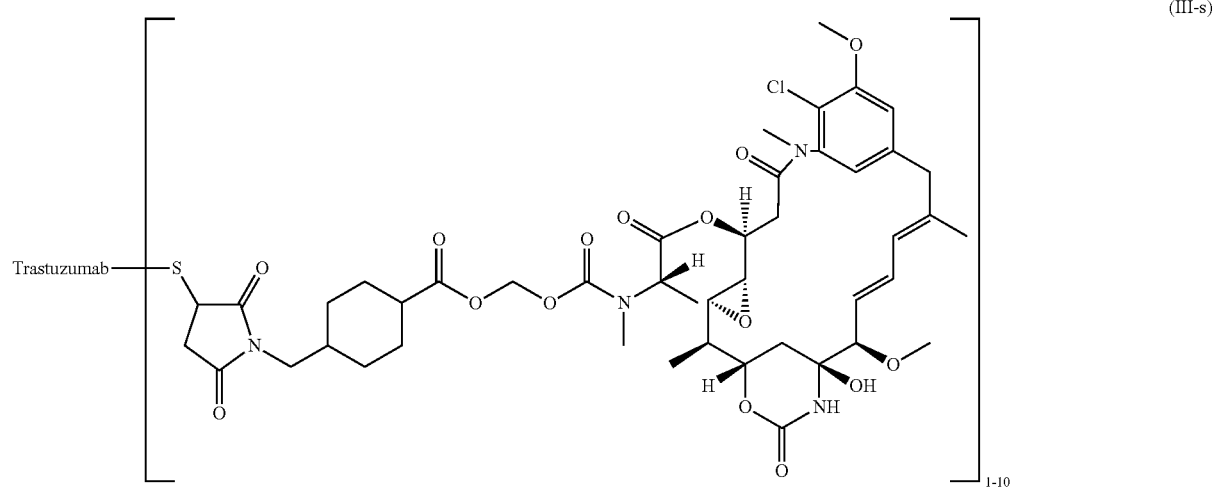
(III-t)
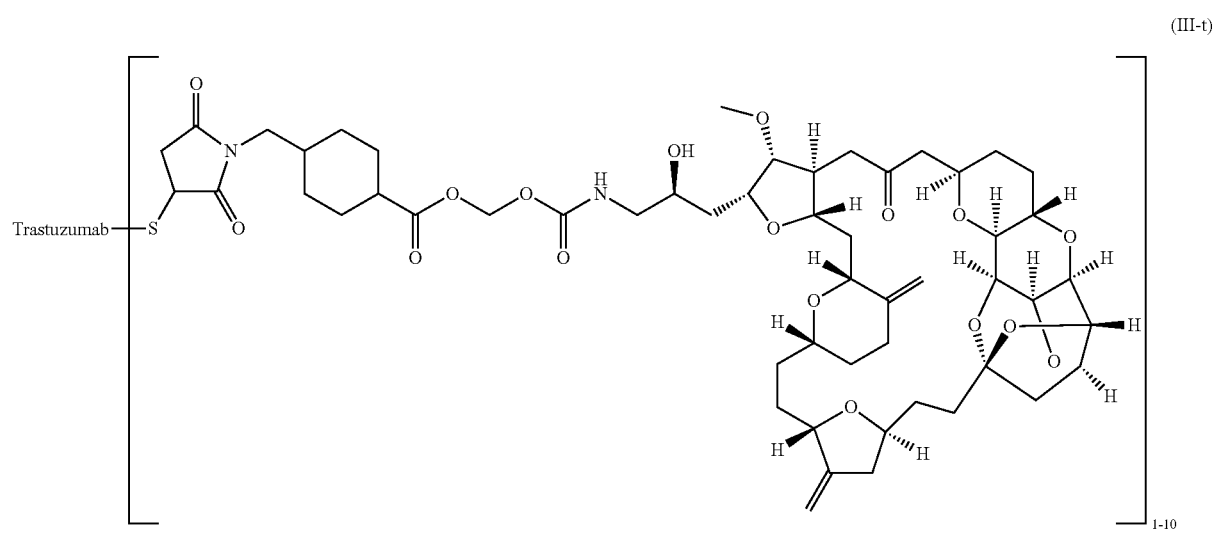
(III-u)
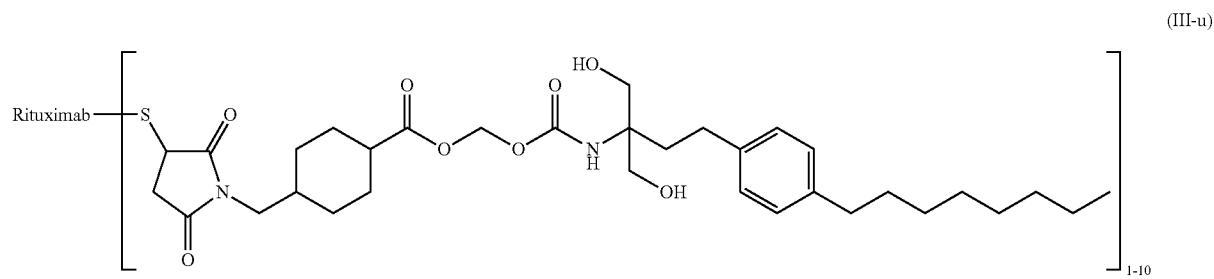
(III-v)
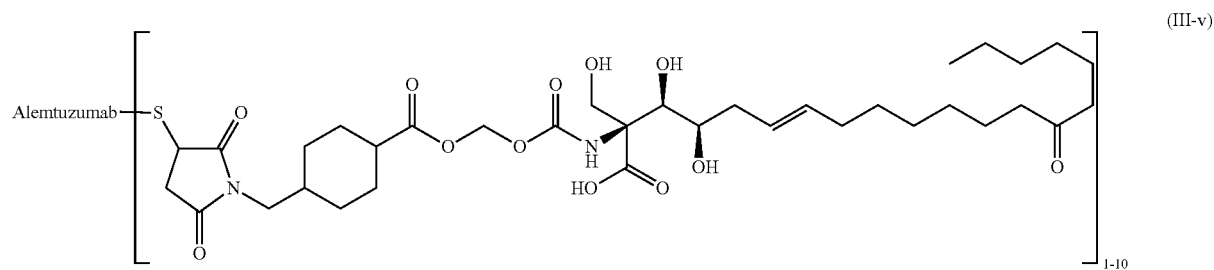

-continued
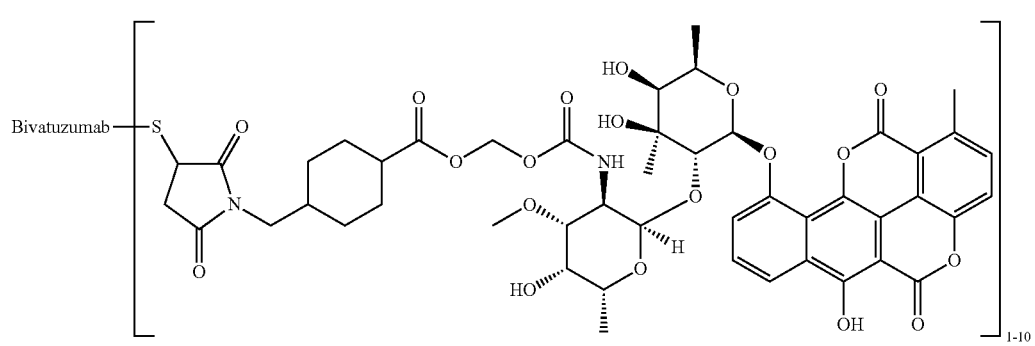
(III-w)
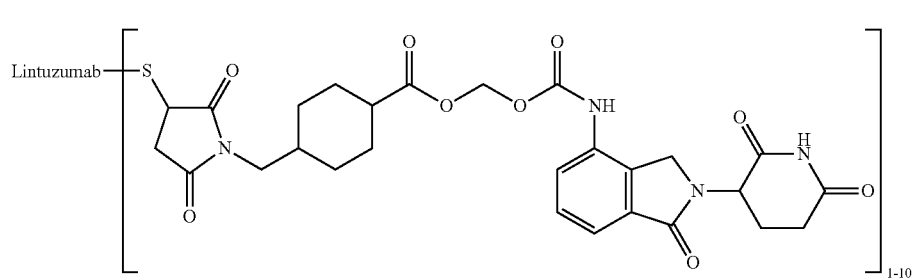
(III-x)
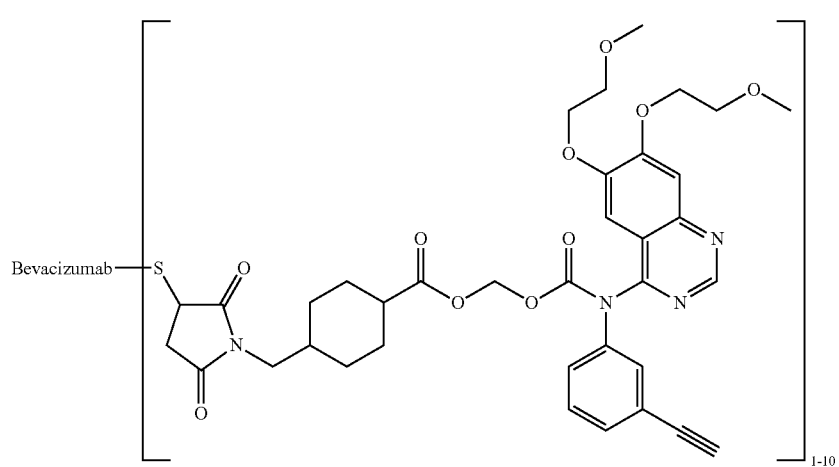
(III-y)
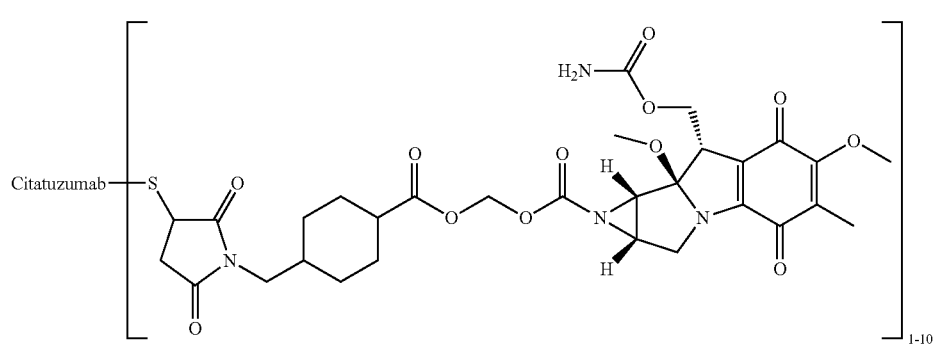
(III-z)

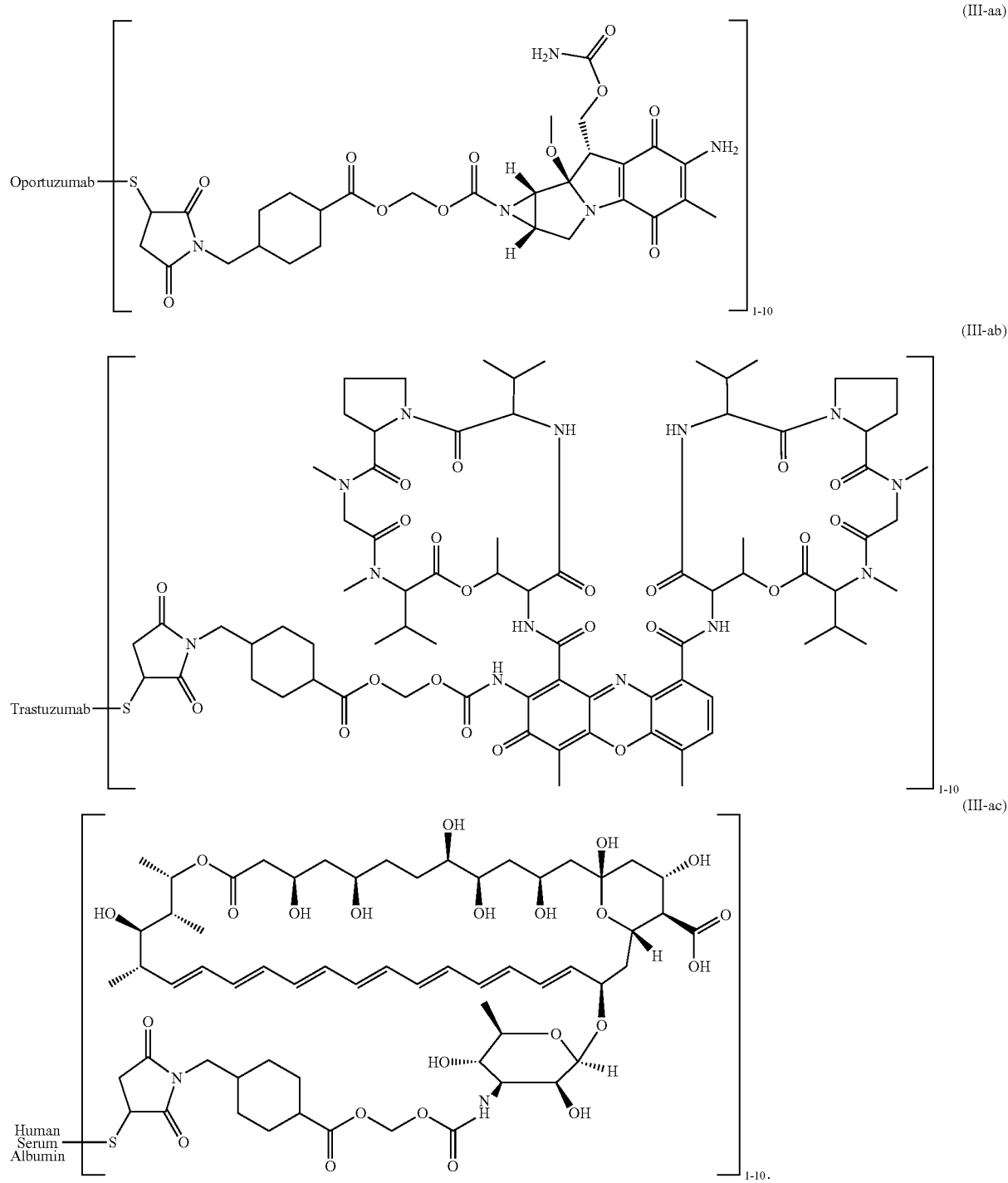

In certain embodiments of a compound of Formula (III), the compound has the structure of Formula (III-a) or a pharmaceutically acceptable salt thereof.

In certain embodiments of a compound of Formula (III), the compound has the structure of Formula (III-b) or a pharmaceutically acceptable salt thereof.

In certain embodiments of a compound of Formula (III), the compound has the structure of Formula (III-c) or a pharmaceutically acceptable salt thereof.

In certain embodiments of a compound of Formula (III), the compound has the structure of Formula (III-d) or a pharmaceutically acceptable salt thereof.

In certain embodiments of a compound of Formula (III), the compound has the structure of Formula (III-e) or a pharmaceutically acceptable salt thereof.

In certain embodiments of a compound of Formula (III), the compound has the structure of Formula (III-f) or a pharmaceutically acceptable salt thereof.

In certain embodiments of a compound of Formula (III), the compound has the structure of Formula (III-g) or a pharmaceutically acceptable salt thereof.

In certain embodiments of a compound of Formula (III), the compound has the structure of Formula (III-h) or a pharmaceutically acceptable salt thereof.

In certain embodiments of a compound of Formula (III), the compound has the structure of Formula (III-i) or a pharmaceutically acceptable salt thereof.

In certain embodiments of a compound of Formula (III), the compound has the structure of Formula (III-j) or a pharmaceutically acceptable salt thereof.

In certain embodiments of a compound of Formula (III), the compound has the structure of Formula (III-k) or a pharmaceutically acceptable salt thereof.

In certain embodiments of a compound of Formula (III), the compound has the structure of Formula (III-l) or a pharmaceutically acceptable salt thereof.

In certain embodiments of a compound of Formula (III), the compound has the structure of Formula (III-m) or a pharmaceutically acceptable salt thereof.

In certain embodiments of a compound of Formula (III), the compound has the structure of Formula (III-n) or a pharmaceutically acceptable salt thereof.

In certain embodiments of a compound of Formula (III), the compound has the structure of Formula (III-o) or a pharmaceutically acceptable salt thereof.

In certain embodiments of a compound of Formula (III), the compound has the structure of Formula (III-p) or a pharmaceutically acceptable salt thereof.

In certain embodiments of a compound of Formula (III), the compound has the structure of Formula (III-q) or a pharmaceutically acceptable salt thereof.

In certain embodiments of a compound of Formula (III), the compound has the structure of Formula (III-r) or a pharmaceutically acceptable salt thereof.

In certain embodiments of a compound of Formula (III), the compound has the structure of Formula (III-s) or a pharmaceutically acceptable salt thereof.

In certain embodiments of a compound of Formula (III), the compound has the structure of Formula (III-t) or a pharmaceutically acceptable salt thereof.

In certain embodiments of a compound of Formula (III), the compound has the structure of Formula (III-u) or a pharmaceutically acceptable salt thereof.

In certain embodiments of a compound of Formula (III), the compound has the structure of Formula (III-v) or a pharmaceutically acceptable salt thereof.

In certain embodiments of a compound of Formula (III), the compound has the structure of Formula (III-w) or a pharmaceutically acceptable salt thereof.

In certain embodiments of a compound of Formula (III), the compound has the structure of Formula (III-x) or a pharmaceutically acceptable salt thereof.

In certain embodiments of a compound of Formula (III), the compound has the structure of Formula (III-y) or a pharmaceutically acceptable salt thereof.

In certain embodiments of a compound of Formula (III), the compound has the structure of Formula (III-z) or a pharmaceutically acceptable salt thereof.

In certain embodiments of a compound of Formula (III), the compound has the structure of Formula (III-aa) or a pharmaceutically acceptable salt thereof.

In certain embodiments of a compound of Formula (III), the compound has the structure of Formula (III-ab) or a pharmaceutically acceptable salt thereof.

In certain embodiments of a compound of Formula (III), the compound has the structure of Formula (III-ac) or a pharmaceutically acceptable salt thereof.

In certain embodiments, cleavable crosslinkers, when coupled to a primary or secondary amine-containing compound, are labile under mild basic conditions. In certain embodiments, a conjugate of Formula (II) or Formula (III) can be cleaved from a primary or secondary amine-containing compound from about pH 7.4 to about pH 10, from about pH 7.4 to about pH 9.0, and in certain embodiments from about pH 7.4 to about pH 8.5.

Method of Synthesis of Cleavable Drug Conjugates

Cleavable crosslinkers, cleavable crosslinking intermediates, and cleavable conjugates provided by the present disclosure may be synthesized by methods known to those skilled in the art. For example, methods of synthesizing related acyloxyalkyl carbamate compounds are described by Alexander, U.S. Pat. No. 4,760,057; Alexander, U.S. Pat. No. 4,916,230; Lund, U.S. Pat. No. 5,401,868; Alexander, U.S. Pat. No. 5,466,811; Alexander, U.S. Pat. No. 5,684,018; Gallop, U.S. Pat. No. 7,227,028, and Singh, PCT Publication No. WO 2005097760.

In certain embodiments, methods of synthesizing conjugates of Formula (II) or Formula (III) comprise (i) mixing a solution containing a compound having at least one primary amine group and/or at least one secondary amine group (D-NH$_2$) and a cleavable crosslinker of Formula (I) in dimethylformamide (DMF), dimethyl sulfoxide (DMSO) or an aqueous buffer (pH 7.0-8.5) such as phosphate buffered saline (PBS) for at least 30 minutes at room temperature to obtain the corresponding conjugate of Formula (II); and (ii) mixing a solution containing the conjugate of Formula (II) and a ligand having at least one thiol group (Q-SH) in dimethylformamide (DMF), dimethyl sulfoxide (DMSO) or an aqueous buffer (pH 7.0-8.5) such as phosphate buffered saline (PBS) for at least 30 minutes at room temperature to obtain the corresponding conjugates of Formula (III) as shown in Scheme A.

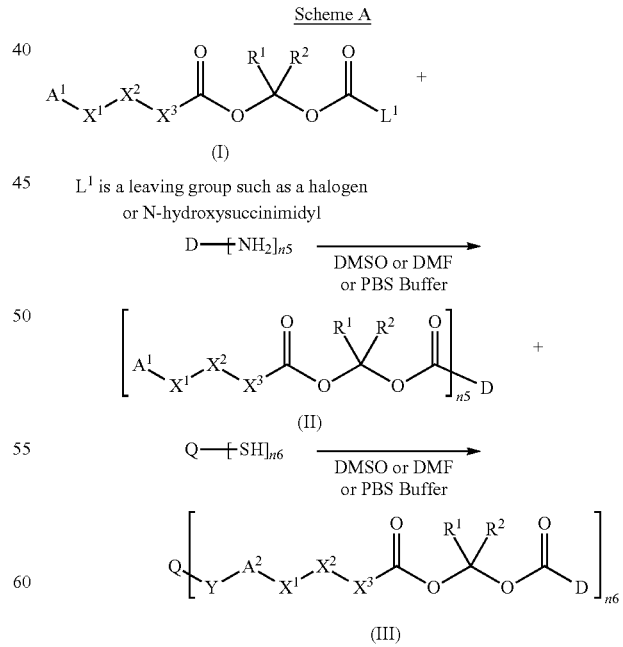

In certain embodiments, methods of synthesizing cleavable drug conjugates of Formula (II) and Formula (III) are shown in Schemes 1 to 6.

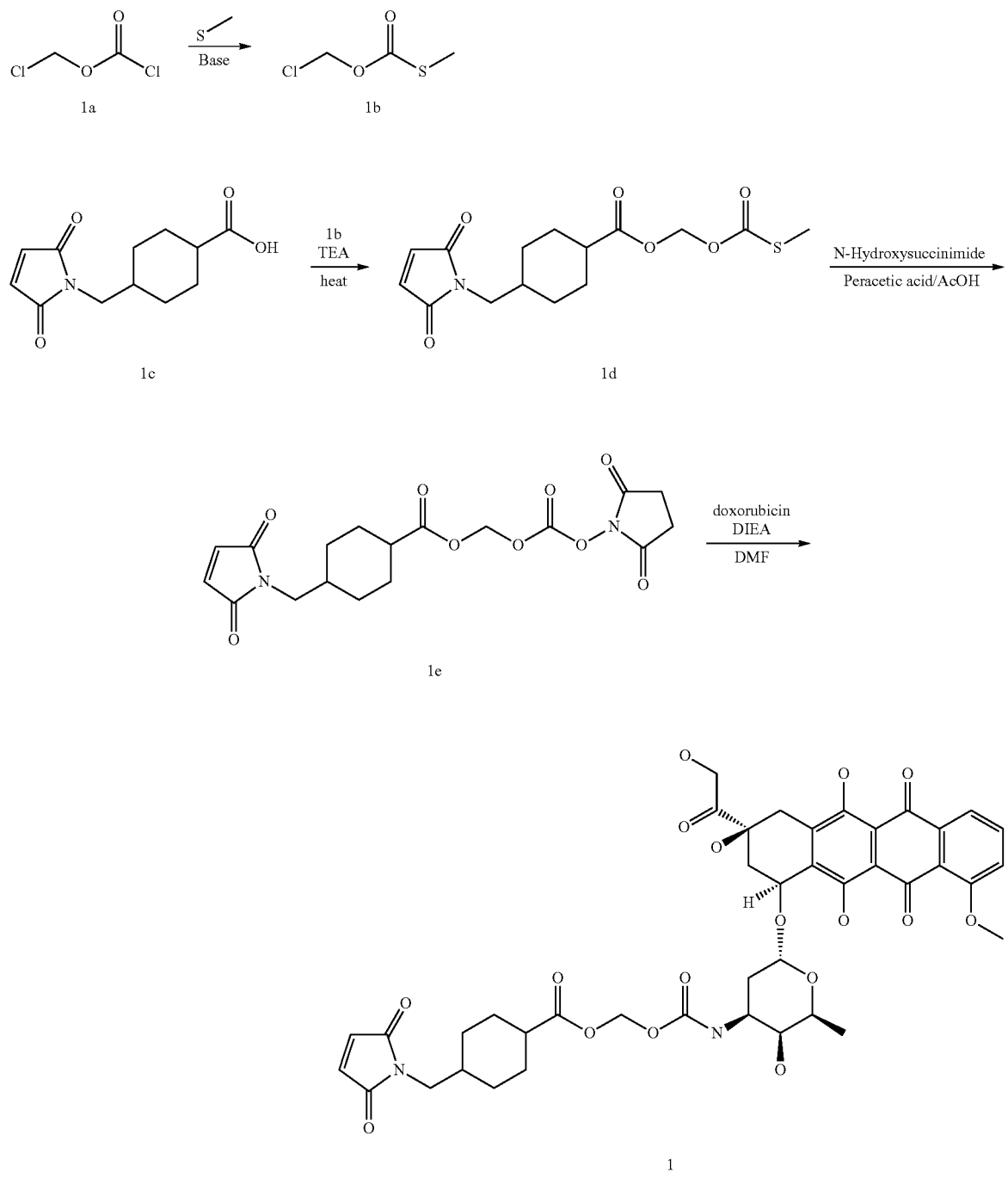
Scheme 2
1e + mitoxantrone
↓ DMSO or DMF or PBS Buffer

-continued
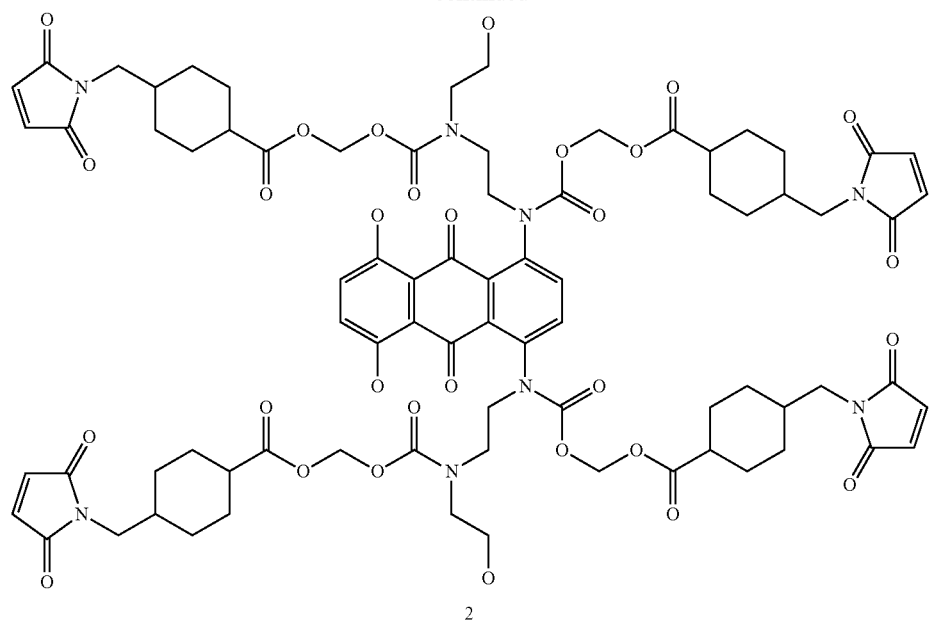
2
Scheme 3
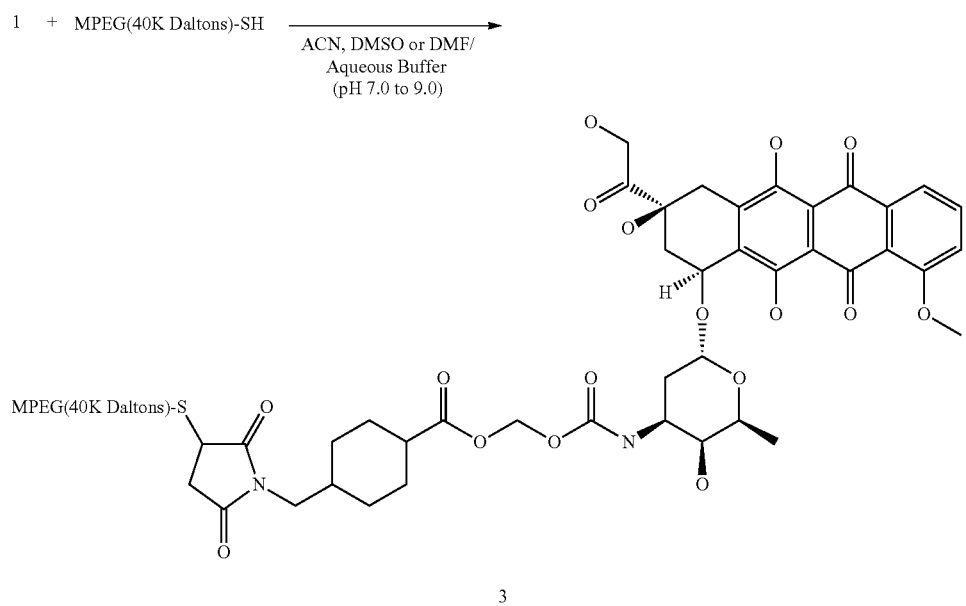
3
Scheme 4
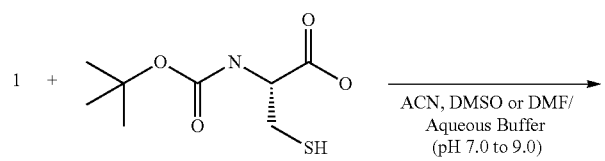

-continued
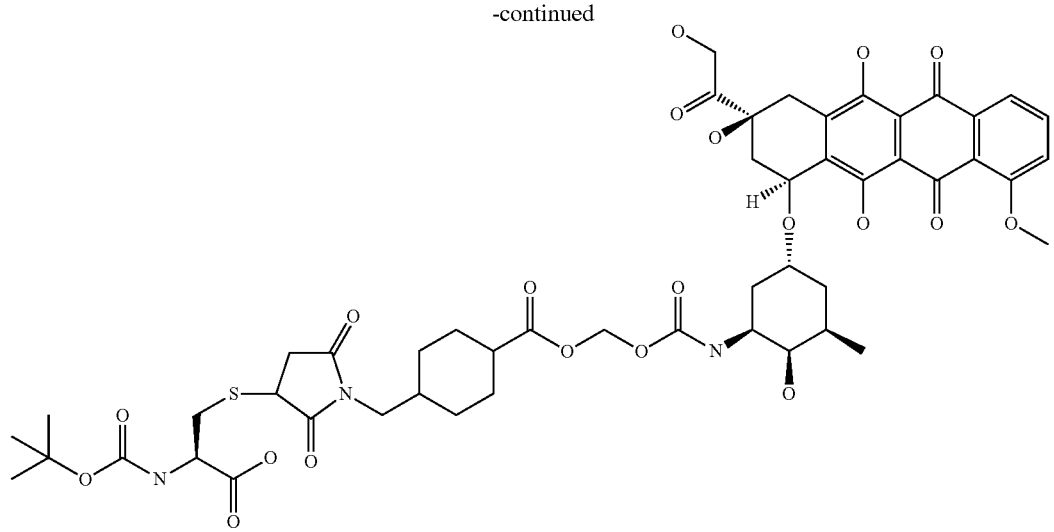
4
Scheme 5
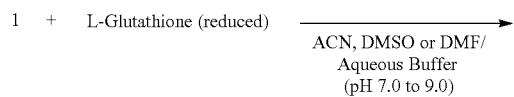
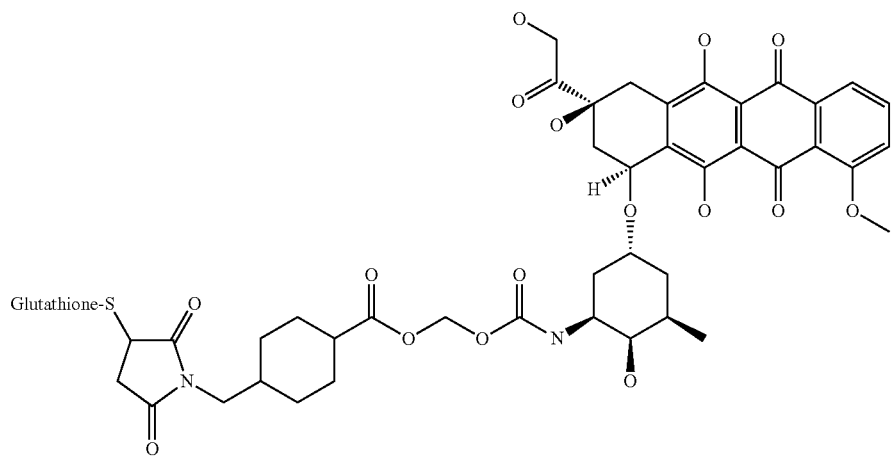
5
Scheme 6
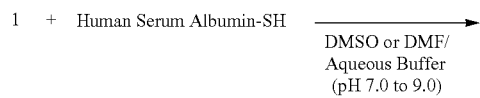

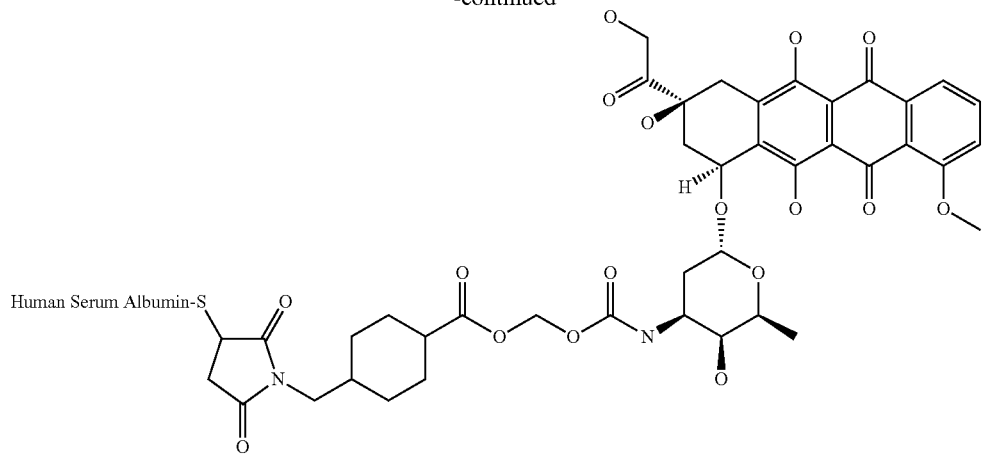

6

Example of therapeutic agents having a primary amine group and/or a secondary amine group include aminopterin, folitixorin, methotrexate, pemetrexed, pralatrexate, raltitrexed, pelitrexol, talotrexin, deoxycoformycin, cladribine, clofarabine, fludarabine, thioguanine, mercaptopurine, berubicin, daunorubicin, doxorubicin, epirubicin, idarubicin, amrubicin, pirarubicin, zorubicin, mitoxantrone, banoxantrone, ledoxantrone, nortopixantrone, pixantrone, piroxantrone, sabarubicin, topixantrone, monomethyl auristatin E, monomethyl auristatin F, monomethyl dolastatin 10, dolastatin 15, belotecan, atiratecan, camptothecin, exatecan, irinotecan, namitecan, rubitecan, topotecan, demecolcine, duocarmycin A, duocarmycin SA, duocarmycin B, duocarmycin B1, abbeymycin, anthramycin, centanamycin, chicamycin, mazethramycin, porothramycin A, porothramycin B, sibanomycin, sibiromycin, trabectedin, calicheamicin γ1, calicheamicin T, esperamicin A1, esperamicin C, esperamicin D, dynemicin A, dynemicin H, dynemicin M, dynemicin N, dynemicin O, dynemicin P, dynemicin Q, dynemicin S, neocarzinostatin chromophore, uncialamycin, 21-aminoepothilone B, eribulin, hemiasterlin, HTI-286, kahalatide F, elsamitrucin, lucanthone, melphalan, mitoguazone, nimustine, procarbazine, dacarbazine, amsacrine, 5-amino-4-oxopentanoic acid, methyl 5-amino-4-oxo-pentanoate, actinomycin D, 7-aminoactinomycin D, bleomycin, mitomycin, staurosporine, desacetylvinblastine hydrazide, vinblastine, vincristine, vindestine, vinflunine, vinorelbine, afatinib, apilimod, balamapimod, barasertib, bosutinib, canertinib, cevipabulin, crizotinib, dacomitinib, dasatinib, denibulin, dilmapimod, dinaciclib, dovitinib, dutacatib, duvoglustat, edotecarin, elisidepsin, entinostat, epetirimod, erlotinib, fingolimod, fostamatinib, gefitinib, golotimod, gusperimus, imatinib, imiquimod, intedanib, ispinesib, lapatinib, lenalidomide, linifanib, litronesib, losmapimod, metesind, mocetinostat, motesanib, masitinib, myriocin, neratinib, nilotinib, odanacatib, ombrabulin, pamapimod, panobinostat, pazopanib, plerixafor, pomalidomide, razupenem, resiquimod, sabarubicin, saracatinib, seliciclib, selumetinib, sotirimod, squalamine, tacedinaline, talabostat, taltobulin, telatinib, tipifarnib, tozasertib, vandetanib, vatalanib, veliparib, voreloxin, alvespimycin, amikacin, amphotericin B, arbekacin, astromicin, bacitracin, balofloxacin, bederocin, bekanamycin, besifloxacin, brodimoprim, ciprofloxacin, clinafloxacin, colistin, daptomycin, dibekacin, enoxacin, framycetin, garenoxacin, gatifloxacin, gemifloxacin, gentamicin, gentamicin, grepafloxacin, hamycin, hexetidine, hygromycin B, ibacitabine, iclaprim, isepamicin, kanamycin, lomefloxacin, lucimycin, lymecycline, mepartricin, moxifloxacin, natamycin, nemonoxacin, neomycin B, neomycin C, netilmicin, norfloxacin, nystatin, omadacycline, oritavancin, paromomycin, pazufloxacin, perimycin A, perimycin B, perimycin C, pipemidic acid, polymyxin B, puromycin, radezolid, retaspimycin, ribostamycin, rimocidin, sisomicin, sitafloxacin, sparfloxacin, spectinomycin, streptomycin, sulfacetamide, sulfadiazine, sulfadimethoxine, sulfadimidine, sulfafurazole, sulfalene, sulfamazone, sulfamerazine, sulfamethizole, sulfamethoxazole, sulfamethoxypyridazine, sulfametomidine, sulfametoxydiazine, sulfametrole, sulfamoxole, sulfanilamide, sulfaperin, sulfaphenazole, sulfapyridine, sulfathiazole, sulfathiourea, sulfisomidine, teicoplanin, telavancin, tanespimycin, temafloxacin, tetroxoprim, tigecycline, tobramycin, tosufloxacin, trimethoprim, trimethoprim, trovafloxacin, tyrothricin, ulifloxacin, valnemulin, vancomycin, verdamicin, and zabofloxacin. Other therapeutic agents having a primary amine group and/or a secondary amine group are described in various compendia, such as, for example, the Merck Index, 14th Edition, 2006; and the Physicians Desk Reference, 64th Edition, 2009.

An example of a therapeutic agent having at least one thiol group is captopril.

Examples of therapeutic agents having at least one hydroxy group include doxorubicin and camptothecin.

Pharmaceutical Compositions Comprising Conjugates

Certain embodiments provided by the present disclosure relate to pharmaceutical compositions, formulations, routes of administration and doses of conjugates of Formula (II) or Formula (III).

Conjugates of Formula (II) or Formula (III) may be formulated with one or more suitable pharmaceutically acceptable vehicles, diluents, and/or excipients, which are well known, and can be determined, by one of skill in the art.

In certain embodiments, when the route of administration is parenteral (e.g. intravenous, intramuscular, intravenous, subcutaneous or interperitoneal), the vehicle or excipient or excipient mixture can be a solvent or a dispersive medium containing, for example, various polar or nonpolar solvents, suitable mixtures thereof or oils. Examples of vehicles or excipients include, but are not limited to, pharmaceutically acceptable solvents, dispersive agents or media, coatings, antimicrobial agents, iso- or hypo- or hypertonic agents, absorption modifying agents. Moreover, other or supplementary active ingredients can also be incorporated into the composition.

In certain embodiments, a pharmaceutical composition includes carriers and excipients such as buffers, carbohydrates, mannitol, proteins, polypeptides or amino acids such as glycine, antioxidants, bacteriostats, chelating agents, suspending agents, thickening agents and/or preservatives, water, oils including but not limited to those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances as required to approximate physiological conditions, such as pH buffering agents, tonicity adjusting agents, emulsifying agents, wetting agents and the like. Examples of excipients include, but are not limited to, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In certain embodiments, a pharmaceutical preparation is substantially free of preservatives. In certain embodiments, a pharmaceutical preparation contains at least one preservative.

Administration

In certain embodiments, conjugates of Formula (II) and Formula (III) may be administered or applied singly, in combination with one or more pharmaceutically active agents, including another conjugate provided by the present disclosure.

Conjugates of Formula (II) and Formula (III) and compositions thereof may be administered by any appropriate route. In certain embodiments, conjugates of Formula (II) and Formula (III) and compositions thereof may be administered parenterally, for example, by infusion or bolus injection.

Dosage

Pharmaceutical compositions provided by the present disclosure comprise a conjugate of Formula (II) or Formula (III) and a pharmaceutically acceptable vehicle. In certain embodiments, a compound of Formula (II) or Formula (III) is present in a therapeutically effective amount, i.e., in an amount effective to achieve therapeutic benefit in a patient having a cancer, an autoimmune disease, or an infectious disease. The amount effective for a particular treatment will depend, at least in part, on the disease or diseases being treated, the condition of the patient, the severity of the disease, the formulation, and the route of administration, as well as other factors known to those of skill in the art. In vitro or in vivo assays can optionally be employed to help identify optimal doses and dosing regimens.

In certain embodiments, a therapeutically effective amount of a conjugate of Formula (II) or Formula (III) sufficient to treat a cancer, an autoimmune disease, or an infectious disease in a patient is from about 1 mg to about 10,000 mg of a conjugate of Formula (II) or Formula (III); in certain embodiments, from about 1 mg to about 5,000 mg; and in certain embodiments, from about 1 mg to about 1,000 mg of a conjugate of Formula (II) or Formula (III).

Therapeutic Use

A conjugate of Formula (II), a conjugate of Formula (III), or a pharmaceutical composition of any of the foregoing, can be administered to a mammal, such as a human, to treat a cancer, an autoimmune disease, or an infectious disease.

In certain embodiments, methods of treating a cancer in a patient comprise administering to a patient in need of such treatment a conjugate of Formula (II), a conjugate of Formula (III), or a pharmaceutical composition of any of the foregoing, wherein D is therapeutically effective for treating the cancer. In certain embodiments, the cancer is selected from adrenal cortical cancer, anal cancer, aplastic anemia, bile duct cancer, bladder cancer, bone cancer, bone metastasis, a brain cancer, a central nervous system (CNS) cancer, a peripheral nervous system (PNS) cancer, breast cancer, cervical cancer, childhood Non-Hodgkin's lymphoma, colon and rectum cancer, endometrial cancer, esophagus cancer, Ewing's family of tumors, eye cancer, gallbladder cancer, a gastrointestinal carcinoid tumor, a gastrointestinal stromal tumor, gestational trophoblastic disease, hairy cell leukemia, Hodgkin's lymphoma, Kaposi's sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, a lung carcinoid tumor, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, a sarcoma, melanoma skin cancer, non-melanoma skin cancers, stomach cancer, testicular cancer, thymus cancer, thyroid cancer, uterine cancer, transitional cell carcinoma, vaginal cancer, vulvar cancer, mesothelioma, squamous cell or epidermoid carcinoma, bronchial adenoma, choriocarcinoma, head and neck cancers, teratocarcinoma, and Waldenstrom's macroglobulinemia. In certain embodiments, the cancer is selected from acute lymphocytic leukemia, acute myeloid leukemia, chronic lymphocytic leukemia, chronic myeloid leukemia, multiple myeloma, breast cancer, prostate cancer, lung cancer, kidney cancer, liver cancer, and colon cancer.

In certain embodiments, methods of treating an autoimmune disease in a patient comprise administering to a patient in need of such treatment a conjugate of Formula (II), a conjugate of Formula (III), or a pharmaceutical composition of any of the foregoing, wherein D is therapeutically effective for treating the autoimmune disease. In certain embodiments, the autoimmune disease is selected from alopecia areata, ankylosing spondylitis, Chagas disease, chronic obstructive pulmonary disease, Crohns Disease, dermatomyositis, diabetes mellitus type 1, endometriosis, Goodpasture's syndrome, Graves' disease, Guillain-Barré syndrome, Hashimoto's disease, Hidradenitis suppurativa, Kawasaki disease, IgA nephropathy, idiopathic thrombocytopenic purpura, interstitial cystitis, lupus erythematosus, lupus nephritis, mixed connective tissue disease, morphea, multiple sclerosis, Myasthenia gravis, carcolepsy, meuromyotonia, Pemphigus vulgaris, Pernicious anaemia, psoriasis, psoriatic arthritis, polymyositis, primary biliary cirrhosis, relapsing polychondritis, rheumatoid arthritis, sarcoidosis, schizophrenia, scleroderma, Sjögren's syndrome, temporal arteritis, ulcerative colitis, vasculitis, and Wegener's granulomatosis. In certain embodiments, the autoimmune disease is selected from lupus erythematosus, psoriasis and multiple sclerosis. In certain embodiments, the autoimmune disease is multiple sclerosis and the multiple sclerosis is selected from relapsing remitting multiple sclerosis, secondary progressive multiple sclerosis, primary progressive multiple sclerosis, and progressive relapsing multiple sclerosis.

In certain embodiments, methods of treating an infectious disease in a patient comprise administering to a patient in need of such treatment a conjugate of Formula (II), a conjugate of Formula (III), or a pharmaceutical composition of any of the foregoing, wherein D is therapeutically effective for treating the infectious disease. In certain embodiments, the infectious disease is selected from a fungal disease, a bacterial disease, and a viral disease. In certain embodiments, the infectious disease is a viral disease and the viral disease is selected from Hepatitis A, Hepatitis B, Hepatitis C, and autoimmune deficiency disorder (AIDS).

In certain embodiments, a conjugate of Formula (II) or Formula (III) or a pharmaceutical composition of any of the foregoing may be administered to a patient together with at least one second therapeutic agent. In certain embodiments, the at least one second therapeutic agent is selected from an antitumor alkylating agent, an antitumor antimetabolite, an antitumor antibiotic, a plant-derived antitumor agent, an antitumor organoplatinum compound, an antitumor campthotecin derivative, an antitumor tyrosine kinase inhibitor, a monoclonal antibody, an interferon, a biological response modifier, a hormonal anti-tumor agent, an angiogenesis inhibitor, a differentiating agent, and a pharmaceutically acceptable salt of any of the foregoing. In certain embodiments, the at least one second therapeutic agent is selected from paclitaxel, docetaxel, cyclophosphamide, ribavirin, and bortezomib.

A second therapeutic agent can be administered prior to, concomitant with, or subsequent to administering a conjugate of Formula (II) or Formula (III) or pharmaceutical composition of any of the foregoing.

The conjugate compound of Formula (II) or Formula (III) can be cleaved under mild basic conditions and/or by esterases in vivo to release the pharmaceutical agent. In certain embodiments, the conjugate Formula (II) or Formula (III) can release the pharmaceutical agent in vivo from about pH 7.4 to about pH 10, from about pH 7.4 to about pH 9.0, and in certain embodiments from about pH 7.4 to about pH 8.5.

EXAMPLES

The following examples describe in detail methods of synthesizing crosslinkers, intermediates, and conjugates provided by the present disclosure, assays for characterizing crosslinkers and conjugates provided by the present disclosure, and methods of using crosslinkers and conjugates provided by the present disclosure. It will be apparent to those skilled in the art that many modifications, both to materials and methods, may be practiced without departing from the scope of the disclosure.

Example 1

Synthesis of Doxorubicin Conjugate (1)

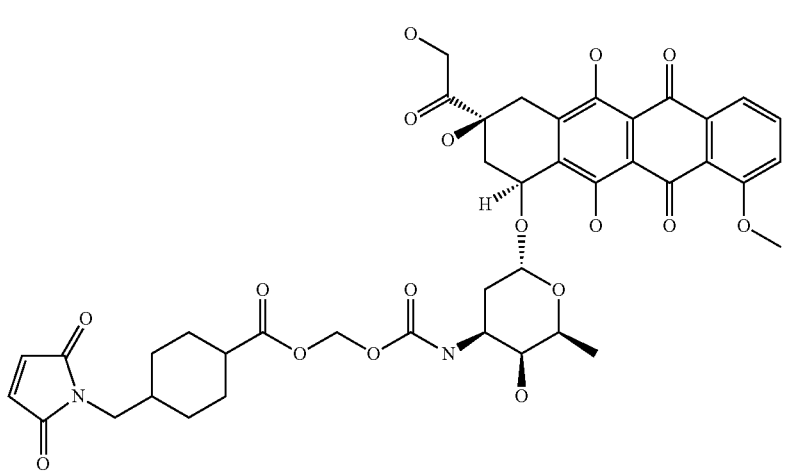

A mixture of 1-chloromethyl chloroformate (1.0 eq) and tetrabutylammonium bisulfate (0.20 eq) in dichloromethane was cooled to 0° C. with an ice-water bath. A 21% solution of sodium methanethiolate (1.0 eq) in water was added. The bilayer was stirred at 0° C. for 1 h and then at room temperature for 16 h. The reaction mixture was diluted with dichloromethane, washed with water, saturated bicarbonate solution and brine, then dried over $Na_2SO_4$, filtered and concentrated in vacuo to provide compound (1b) as a colorless liquid.

A mixture of 4-[(2,5-dioxopyrrol-1-yl)methyl]cyclohexanecarboxylic acid (1c), compound (1b) (1.0 eq), and triethylamine (1.0 eq) was stirred at 70° C. for 24 h. The reaction mixture was diluted with ethyl acetate, and washed with water, saturated bicarbonate solution and brine. The organic phase was separated, dried over $Na_2SO_4$, filtered and concentrated in vacuo to yield the crude product. The crude material was then purified by silica gel column chromatography using ethyl acetate and hexanes to yield compound (1d).

To a solution of compound (1d) (1.0 eq) in dichloromethane (10 mL) was added N-hydroxysuccinimide (NHS) (3.0 eq) and the reaction mixture cooled to 0° C. A solution of 32% (v/v) peracetic acid in acetic acid (3.0 eq) was added dropwise over a period of 10 mins, and the solution was stirred at 0° C. for 3 h and then at room temperature overnight. The reaction mixture was then diluted with dichloromethane and washed with water, saturated sodium bicarbonate solution and brine, then dried over $Na_2SO_4$, filtered and concentrated in vacuo to give the crude product. The crude material was then purified by silica gel column chromatography using ethyl acetate and hexanes to yield compound (1e).

A mixture of compound (1e) (25.25 mg) and doxorubicin HCl (1.0 eq) and TEA (1.0 eq) in DMF (0.40 mL) was stirred at room temperature for 1 h and then concentrated under vacuum. The crude was purified by reverse-phase C-18 High Performance Liquid Chromatography (HPLC) using acetonitrile/aqueous buffer as eluent to provide compound (1).

Example 2

Synthesis of Mitoxantrone Conjugate (2)

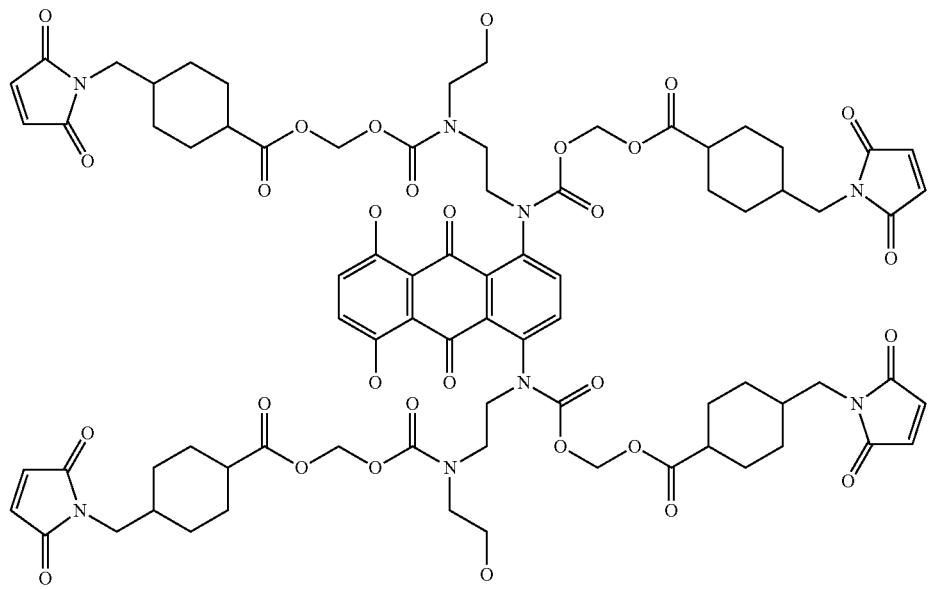

A mixture of compound (1e) (4.0 eq), mitoxantrone (1.0 eq), and TEA (5.0 eq) in acetonitrile/aqueous buffer is stirred at room temperature for 3 h and then concentrated under vacuum. The crude product is purified by reverse-phase C-18 High Performance Liquid Chromatography (HPLC) using acetonitrile/aqueous buffer as eluent to provide compound (2).

Example 3

Synthesis of MPEG-Maleimido-Doxorubicin Conjugate (3)

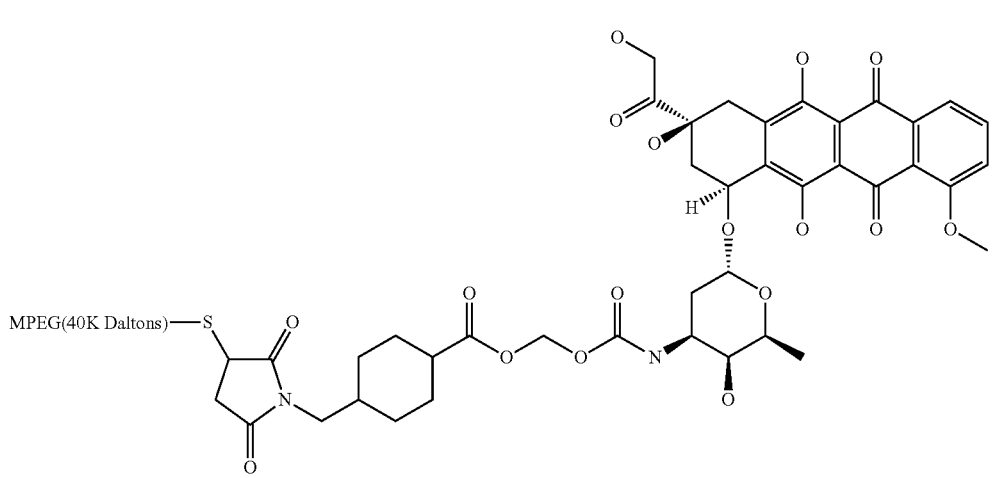

A mixture of compound (1) and MPEG-SH (average MW 40K Daltons) in DMSO/aqueous buffer is stirred at room temperature for 1 h and then concentrated under vacuum. The crude product is purified using size-exclusion chromatography to provide compound (3).

Example 4

Synthesis of Boc-Cysteine-Maleimido-Doxorubicin Conjugate (4)

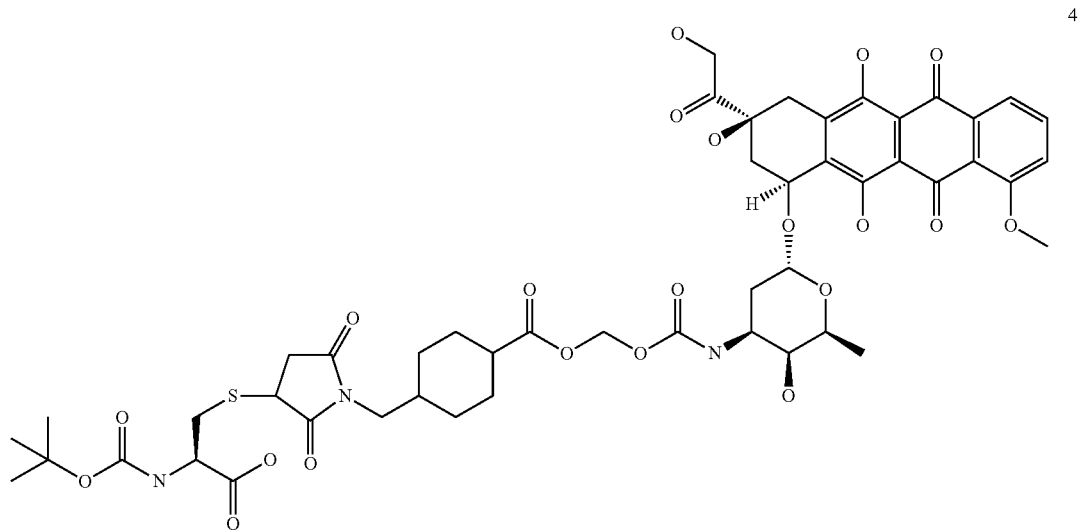 [SMILES: COc1cccc2c1C(=O)c1c(O)c3c(c(O)c1C2=O)C[C@@](O)(C(=O)CO)C[C@@H]3O[C@H]1C[C@H](NC(=O)OCOC(=O)C2CCC(CN3C(=O)CC(SC[C@H](NC(=O)OC(C)(C)C)C(=O)O)C3=O)CC2)[C@H](O)[C@H](C)O1]

A mixture of compound (1) (5.81 mg) and Boc-cysteine (1.23 mg) in acetonitrile/aqueous potassium phosphate buffer (1.6 mL, pH 7.4) was stirred at room temperature for 1 h to provide compound (4). Mass found: M+Na: 1080.

Example 5

Synthesis of L-Glutathione-Maleimido-Doxorubicin Conjugate (5)

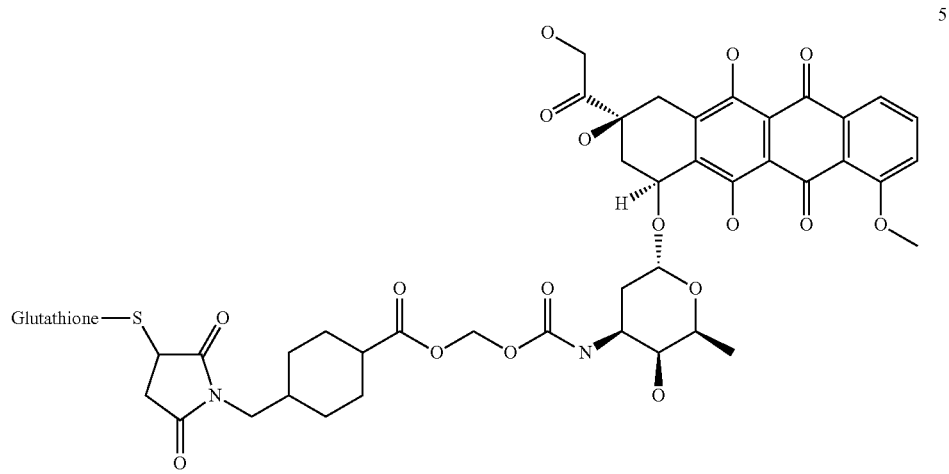

A mixture of compound (1) (8.37 mg) and L-glutathione (reduced) (9.94 mg) in acetonitrile/aqueous potassium phosphate buffer (2 mL, pH 7.4) was stirred at room temperature for 3 h to provide compound (5). Mass found: M+Na: 1167.

Example 6

Synthesis of Human Serum Albumin-Maleimido-Doxorubicin Conjugate (6)

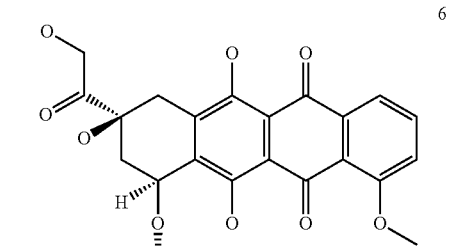
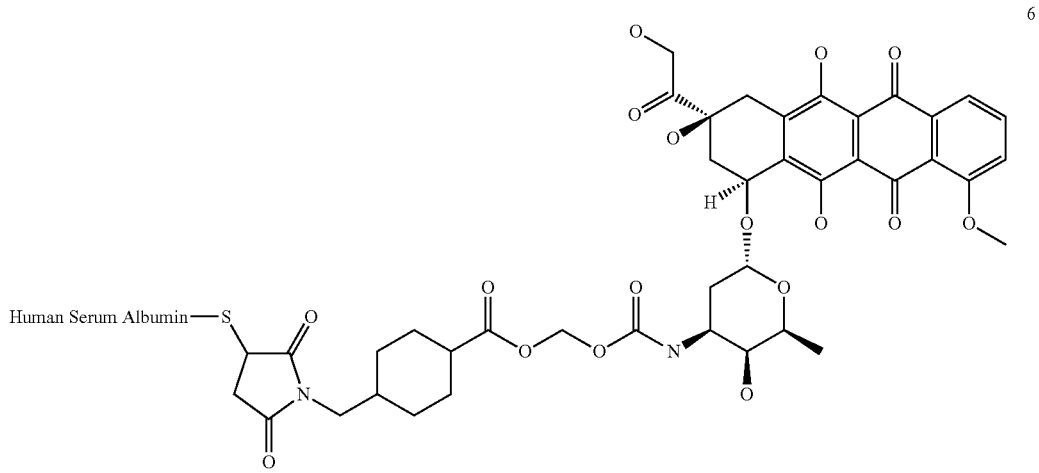

A mixture of compound (1) and human serum albumin in DMSO/aqueous potassium phosphate buffer was stirred at room temperature for 3 h to provide compound (6).

Example 7

Chemical Stability

For chemical stability studies, buffers are prepared at pH 2.0, pH 7.4 and pH 8.0. Compounds (1-500 µM) are incubated with buffers at 37° C. for 1 h in a temperature-controlled HPLC autosampler. Samples for analysis are extracted at zero time and 1 h post-addition. Samples are analyzed by HPLC, liquid chromatography-mass spectrometry (LC/MS), or by liquid chromatography-tandem mass spectrometry (LC/MS/MS).

Example 8

Metabolic Stability/Drug Release

Plasma Stability: Compounds (1-500 µM) are incubated with 10-100% mouse, rat or human serum or plasma at 37° C. for 1 hour to 10 days. Samples are obtained at zero, 1 hour, and up to 10 days post-addition and are immediately quenched with methanol or acetonitrile to prevent further conversion. Quenched samples are immediately analyzed or are frozen and maintained at −80° C. prior to analysis. Samples are analyzed by LC, LC/MS or LC/MS/MS.

Compound 4 (5 µL of a 10 mM DMSO solution) was incubated with a 50% rat serum (Aleken Biologics) in potassium phosphate buffer (pH 7.4) solution (195 µL). After 1 hour, the sample was quenched with acetonitrile (600 µL), centrifuged at 20,000×g, and the supernatant analyzed by LC at 220 nm. The ratio of doxorubicin released to compound 4 was 10:90.

Liver Homogenate: Compounds (1-500 µM) are incubated with rat or human liver S9 at 0.5 mg protein/mL in the presence of 1 mM NADPH at pH 7.4 and at 37° C. for 1 hour to 10 days. Samples are obtained at zero, 1 hour, and up to 10 days post-addition and are immediately quenched with methanol or acetonitrile to prevent further conversion. Quenched samples are immediately analyzed or are frozen and maintained at −80° C. prior to analysis. Samples are analyzed by LC, LC/MS or LC/MS/MS.

Caco-2 Cell Homogenate: Caco-2 cells are grown in flasks over 21 days. Cells are then rinsed/scraped into ice-cold 10 mM sodium phosphate/0.15 M potassium chloride, pH 7.4. Cells are lysed by sonication at 4° C. using a probe sonicator and centrifuged at 9,000×g for 20 min at 4° C. Aliquots of the resulting supernatant (Caco-2 cell homogenate S9 fraction) are transferred into 0.5 mL vials and stored at −80° C. prior to analysis. For stability studies, compounds (5 µM) are incubated with Caco-2 S9 (0.5 mg protein/mL) at pH 7.4 and 37° C. for 1 hour to 10 days. Samples are obtained at zero, 1 hour, and up to 10 days post-addition and are immediately quenched with methanol or acetonitrile to prevent further conversion. Quenched samples are immediately analyzed or are frozen and maintained at −80° C. prior to analysis. Samples are analyzed by LC, LC/MS or LC/MS/MS.

Pancreatin: Compounds (5 µM) are incubated with porcine pancreatin (10 mg/mL in pH 7.5 buffer) at 37° C. for 24 hour. Samples are obtained at zero, 1 hour, and up to 10 days post-addition and are immediately quenched with methanol or acetonitrile to prevent further conversion. Quenched samples are immediately analyzed or are frozen and maintained at −80° C. prior to analysis. Samples are analyzed by LC, LC/MS or LC/MS/MS.

Example 9

In Vitro Cytotoxicity

The effect of compounds provided by the present disclosure on cancer cell growth and viability is measured in a panel of human cancer cells grown in vitro. All cancer cell lines are obtained, for example, from the American Tissue Type Collection (ATTC). Cells are maintained in the following media: TUR, H69AR, Calu-6, ME180, and PC3 cells are grown in RPMI medium containing 4.5 g/L glucose, 10% FBS, 4 mM L-glutamine, and 1 mM sodium pyruvate); and HT29 cells are grown in DMEM with 4.5 g/L glucose, 10% FBS, and 6 mM/L-glutamine. All cells are grown at 37° C. in 5% $CO_2$ and passaged bi-weekly.

For cytoxicity studies, cells are seeded into 96-well clear-bottom microtiter plates at the following densities: TUR (7,500 cells/well), HT29 (5,000 cells/well), H69AR (10,000 cells/well), Calu-6 (15,000 cells/well), and ME180 (2,500 cells/well). Cells are maintained at 37° C. with 5% $CO_2$ for 24 hours prior to addition of a test compound. Each condition is measured in triplicate. For compounds dissolved in DMSO, the final DMSO concentration in each well and in the non-drug treated control cells is constant and below 1% in all studies. The number of viable cells is determined after 24, 48, and 72 hours using Alamar blue fluorescence. Briefly, Alamar blue (10 mM) is added to each well for 4 hours, and the number of viable cells estimated by measuring the fluorescence of reduced Alamar blue (530 nm excitation, 590 nm emission). To correct for background fluorescence, cells are treated with 100% DMSO to eliminate all viable cells. The effect of a test compound on cell growth is determined by calculating the fraction of live cells treated with the test compound compared to untreated cells: (Fl drug treated—Fl DMSO killed)/(Fl untreated—Fl DMSO killed). The half maximal growth inhibition value (GI50) is calculated using commercial curve-fitting software (e.g., Prism).

Example 10

Efficacy in Xenograph Model

Tumor xenograft studies are performed using nude athymic CD-1 mice (for example, from Charles River Laboratories). Human cancer cells ($5 \times 10^6$ PC3, $5 \times 10^6$ HT29, $10^7$ Calu-6, and $5 \times 10^6$ ME 180) are implanted in the hind flank of nude mice. Tumor growth is measured using calipers and tumor volume calculated using the formula: (width $2 \times$(length/2)). Tumor volume is measured 3 days per week. Animal weight is measured 3 days per week to assess compound toxicity.

Compounds are tested for in vivo tumor growth inhibition as follows. Animals bearing tumors (100-200 mg) are sorted into groups (5-8 animals) with similar average tumor mass per group. Drug doses are administered by intraperitoneal (IP) injection (0.5 mL). Test compounds are dissolved in phosphate buffered saline (PBS) with the concentration adjusted for animal weight. Actual drug concentrations in formulated doses are verified by quantitative nitrogen detection. Animals are dosed every 7 days for 21 days in most studies. In several studies, animals are dosed twice weekly (days 0, 4, 7, 10, 14, etc.). Tumor volume and animal weight are measured on days 0, 2, 4, 7, 9, 11, 14, 16, 18, 21, 23, 25, and 28. At the end of the study, animal blood is removed for analysis of liver and kidney function (BUN, creatine, AST and ALT; analytical measurements performed by Quality Clinical Labs). Tumor volume at the end of the study is calculated as a percentage of the tumor volume on day 0. The percent tumor growth inhibition is obtained from the ratio of the percentage tumor volume increase in drug treated animals to the percentage tumor volume increase in saline treated animals.

Finally, it should be noted that there are alternative ways of implementing the disclosures contained herein. Accordingly, the present embodiments are to be considered as illustrative and not restrictive, and the claims are not to be limited to the details given herein, but may be modified within the scope and equivalents thereof.

What is claimed is:

1. A compound of Formula (II):

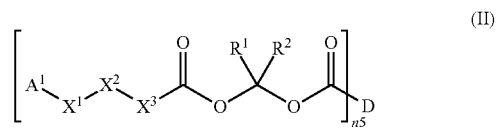

or a salt thereof, wherein:

each $A^1$ is independently a moiety selected from Formula ($A^1$a1), Formula ($A^1$a2), Formula ($A^1$a3), formula ($A^1$b1), Formula ($A^1$ $^b$2), Formula ($A^1$c1), Formula ($A^1$c2), Formula ($A^1$c3). Formula ($A^1$d1), Formula ($A^1$d2), Formula ($A^1$d3), Formula ($A^1$e1). Formula $A^1$f1 and Formula ($A^1$f2):

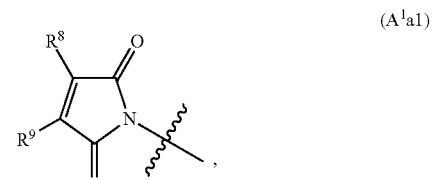

(A$^1$a1)

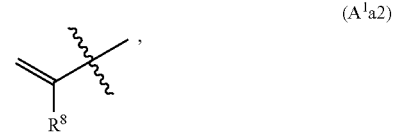

(A$^1$a2)

(A$^1$a3)

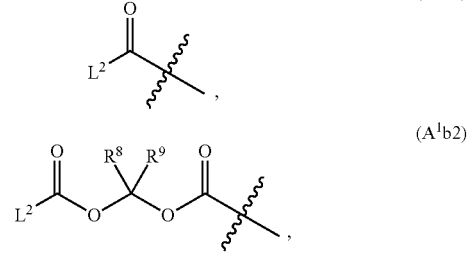

(A$^1$b1)

(A$^1$b2)

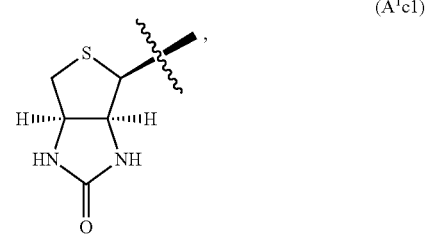

(A$^1$c1)

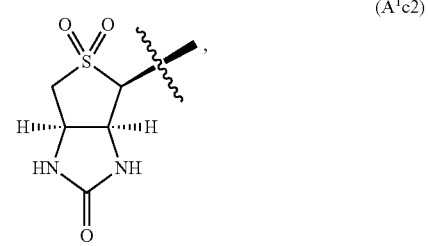

(A$^1$c2)

-continued

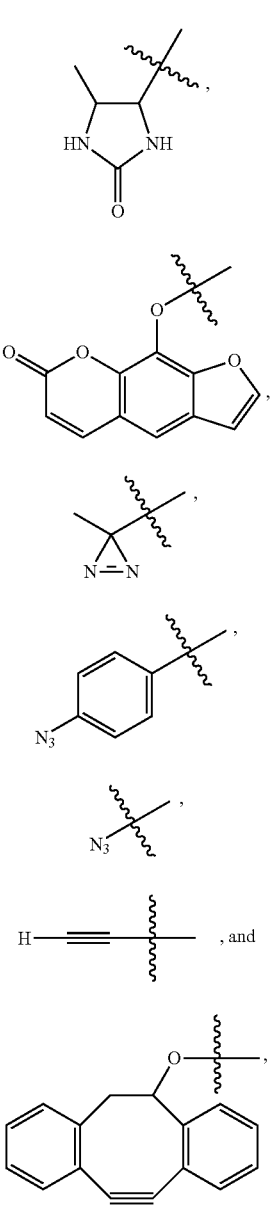

wherein:
each $R^8$ and $R^9$ is independently selected from hydrogen, methyl, ethyl, n-propyl, isopropyl, phenyl, and benzyl;
each E is selected from F, Cl, Br, and I; and
each $L^2$ is selected from halogen, N-hydroxysuccinimidyl, substituted N -hydroxvsuccinimidyl, phenol-yl, substituted phenol-yl, hydroxybenzotriazolyl, substituted hydroxybenzotriazolyl, imidazolyl, and substituted imidazolyl;
each $X^1$ and $X^3$ is independently selected from a covalent bond, $C_{1-20}$ alkanediyl, substituted $C_{1-20}$ alkanediyl, $C_{1-20}$ heteroalkanediyl, substituted $C_{1-20}$ heteroalkanediyl, $C_{3-12}$ cycloalkanediyl, substituted $C_{3-12}$ cycloalkanediyl, $C_{3-12}$ heterocycloalkanediyl, substituted $C^{hd\ 3-12}$ heterocycloalkanediyl, $C_{4-20}$ alkanecycloalkanediyl, substituted $C_{4-20}$ alkanecycloalkanediyl, $C_{4-20}$ heteroalkanecycloalkanediyl, substituted $C_{4-20}$ heteroalkanecycloalkanediyl, $C_{6-20}$ arenediyl, substituted $C_{6-20}$ arenediyl, $C_{6-20}$ heteroarenediyl, substituted $C_{6-20}$ heteroarenediyl, $C_{7-20}$ alkanearenediyl, substituted $C_{7-20}$ alkanearenediyl, $C_{6-20}$ heteroalkanearenediyl, substituted $C_{6-20}$ heteroalkanearenediyl, and —$(CH_2)_{n1}$—$(CH_2$-$CH_2$-$O)_{n2}$—$(CH_2)_{n3}$—, wherein:
each n1 and n3 is independently an integer selected from 0 to 5; and
each n2 is independently an integer selected from 1 to 25;
each $X^2$ is independently selected from a covalent bond, —O—, —S—, NH—, N=, —N=N—, N=CH—, —SO—, —SO$_2$—, SO$_2$NH—, —SS—, —C(O)—, —C(O)O—, —C(O)NH—, —C(O)S—, —C(O)NH—N=, —OP(O)(OH)O—, —OC(O)O—, —OC(O)NH—, —NHC(O)NH—, and —NHC(S)NH—;
each $R^1$ and $R^2$ is independently selected from hydrogen, $C_{1-6}$ alkyl, substituted $C_{1-6}$ alkyl, $C_{1-6}$, heteroalkyl, substituted $C_{1-6}$ heteroalkyl, $C_{6-10}$ aryl, substituted $C_{6-10}$ aryl, $C_{6-10}$ heteroaryl, and substituted $C_{6-10}$ heteroaryl;
D is selected from aminopterin, folitixorin. methotrexate, pemetrexed, ralatrexate, raltitrexed, pelitrexol, talotrexin. deoxycoformycin, cladribine, clofarabine, fludarabine, thioguanine, mercaptopurine, berubicin daunorubicin, doxorubicin, epirubicin, idarubicin, amrubicin, pirarubicin, zorubicin mitoxantrone, banoxantrone, ledoxantrone, nortoixantrone, pixantrone, piroxantrone, sabarubicin, topixantrone, monomethyl, auristatin E, monomethyl, auristatin F, monomethyl, dolastatin, 10, dolastatin 15, belotecan, atiratecan, camptopthecin, exatecan, irinotecan, namitecan, rubitecan, topotecan, demecolcine, duocarmycin A, duocarmycin SA, duocarmycin B, duocarmycin B1 ,abbeymycin, anthramycin, centanamycin, chicamycin, mazethramycin, porothrarnycin A, porothramycin B, sibanomycin, sibiromycm, trabectedin, calicheamicin γ1, calicheamicin T, esperamicin Al, esperamicin C, esperamicin D, dynemicin A, dynemicin H, dynemicin M, dynemicin N, dynemicin O, dynemicin p, dynemicin Q, dynemicin S, neocarzinostatin chromophore, uncialamycin, 21-aminoepothilone B, eribulin, hemiasterlin, HTI-286, kahalatide F, elsamitrucin, lucanthone, melphalan, mitoguazone, nimustine, procarbazine, dacarbazine, amsacrine 5-amino-4-oxo-pentanoic acid. methyl 5-amino-4-oxo -pentanoate, actimomycin D, 7-aminoactinomycin D, bleomycin, mitomycin, staurosporine, desacetylvinblastine hydrazide, vinblastine, vincristine, vindesine, vinflunine, vinorelbine, afatinib, apilimbd, balamanimod, barasertib, bosutinib, ceanertinib, cevipabulin, crizotinib, dacomitinib, dasatinib, denibulin. dilmapimod, dinaciclib, dovitiriib, dutacatib, duvoglustat, edotecarin, elisidepsin, entinostat, epetirimod, erlotinib, fingolimod, fostamatinib, gefitinib, golotimod, gusperimus, imatinib, imiquimod, intedanib, ispinesib, lapatinib, lenalidomide, linifanib, litronesib, losmapimod, metesind, mocetinostat, motesanib, masitinib, myriocin, neratinib, nilotinib, odanacatib, ombrabulin, pamapimod, panobinostat, pazopanib, plerixafor, pomalidomide, razupenem, resiquimod, sabarubicin, saracatinib, seliciclib, selumetinib, sotirimod, squalamine, tacedinaline, talabostat, taltobulin, telatinib, tipifarnib, tozasertib, vandetanib, vatalanib, veliparib, voreloxin, alvespimycin, amikacin, amphotericin B, arbekacin, astromicin, bacitracin, balofloxacin, bederocin, bekanamycin, besifloxacin, brodimoprim, ciprofloxacin, clinafloxacin, colistin, daptomycin, dibekacin, enoxacin, framycetin, garenoxacin, gatifloxacin, gemifloxacin, gentamicin, gentamicin, grepafloxacin, hamycin, hexetidine, hygromycin B, ibacitabine, iclaprim, isepamicin, kanamycin, lomefloxacin, lucimycin, lymecycline, mepartricin, moxifloxacin, natamycin, nemonoxacin, neomycin B, neomycin C, netilmicin, norfloxacin, nystatin, omadacycline, oritavancin, paromomycin, pazufloxacin, perimycin A, perimycin B, perimycin C, pipemidic acid, polymyxin B, puromycin, radezolid, retaspimycin, ribostamycin, rimocidin, sisomicin, sitafloxacin, sparfloxacin, spectinomycin, streptomycin, sulfacetamide, sulfadiazine, sulfadimethoxine, sulfadimidine, sulfafurazole, sulfalene, sulfamazone, sulfamerazine, sulfamethizole, sulfamethoxazole, sulfamethoxypyridazine, sulfametomidine, sulfametoxydiazine, sulfametrole, sulfamoxole, sulfanilamide, sulfaperin, sulfaphenazole, sulfapyridine, sulfathiazole, sulfathiourea, sulfisomidine, teicoplanin, televancin, tanespimycin, temafloxacin, tetroxoprim, tigecycline, tobramycin, tosufloxacin, trimethoprim, trimethoprim, trovafloxacin, tyrothricin, ulifloxacin, valnemulin, vancomycin, verdamicin, and zabofloxacin; and n5 is an interger selected from 1to 20.

2. The compound of claim 1, wherein each $A^1$ is independently a moiety selected from Formula ($A^1$a1a), Formula ($A^1$a2a), Formula ($A^1$a2b), Formula ($A^1$ a3a), Formula ($A^1$a3b), Formula ($A^1$b 1a), Formula ($A^1$b1b), Formula ($A^1$b1c), Formula ($A^1$ b2a), Formula ($A^1$b2b), Formula ($A^{1\,b}$2c), Formula ($A^1$ c I), Formula ($A^1$c2), Formula ($A^1$c3), Formula ($A^1$d1), Formula ($A^1$d2), Formula ($A^1$d3), Formula ($A^1$c1), Formula ($A^1$f1), and Formula ($A^1$f2):

(A¹a1a)
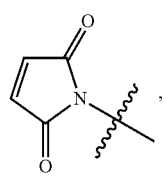

(A¹a2a)
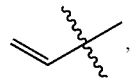

(A¹a2b)
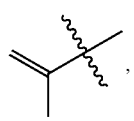

(A¹a3a)
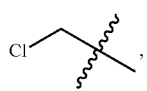

(A¹a3ba)
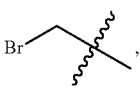

(A¹b1a)
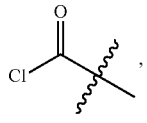

-continued (A¹b1b)
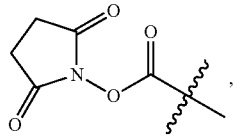

(A¹b1c)
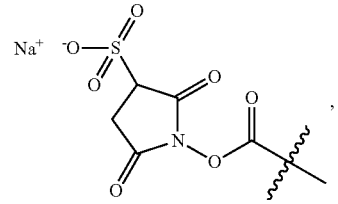

(A¹b2a)
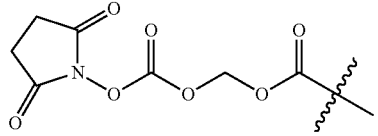

(A¹b2b)
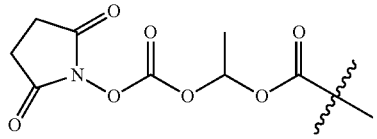

(A¹b2c)
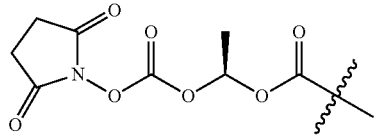

(A¹c1)
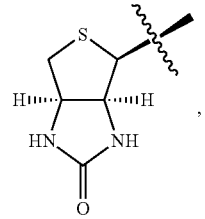

(A¹c2)
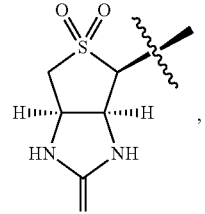

(A¹c3)
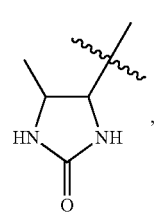

-continued

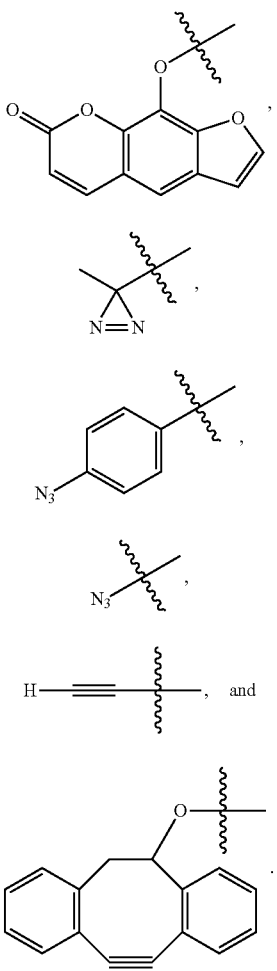

(A¹d1)

(A¹d2)

(A¹d3)

(A¹e1)

(A¹f1)

(A¹f2)

3. The compound of claim 1. wherein each $X^1$ and $X^3$ is independently selected from a covalent bond, $C_{1-20}$alkanediyl, $C_{1-20}$ cycloalkanediyl, $C_{6-10}$ arenediyl, $C_{7-20}$ alkanearenediyl, and —$(CH_2)_{n1}$—$(CH_2$—$CH_2$—$O)_{n2}$—$(CH_2)_{n3}$—, wherein each n1 and n3 is independently an integer selected from 0 to 5 and each n2 is independently an integer selected from 1 to 25.

4. The compound of claim 1, wherein each $X^1$ and $X^3$ is independently selected from a covalent bond, methane-diyl, ethane-1,2-diyl, propane-1,3-diyl, butane-1,4-diyl, pentane-1,5-diyl, hexane-1,6-diyl, benzene-diyl, methylbenzene-diyl, ethylbenzene-diyl, propylbenzcne-diyl, methylcyclohexane-diyl, —$(CH_2)_2$—$(CH_2$—$CH_2$—$O)$—, —$(CH_2)^2$—$(CH_2$—$CH_2$—$O)_2$—$(CH_2)$—, and —$(CH_2)_2$—$(CH^2$—$CH_2$—$O)_3$—$(CH_2)_2$—.

5. The compound of claim 1, wherein each $X^2$ is selected from a covalent bond, —O—, —S—, —SO—, —$SO_2$—, —$SO,NH$— —SS—, —C(O)—, —C(O)O—, —C(O)NH—, C(O)NH—N=, —OC(O)NH—, and —NHC(O)NH—.

6. The compound of claim 1, wherein each. $X^2$ is selected from a covalent bond, —O—, —$SO_2NH$—, —SS—, —C(O)—, —C(O)O—, and —C(O)NH—.

7. The compound of claim 1, wherein each $R^1$ and $R^2$ is independently selected from hydrogen, methyl, ethyl, propyl, isopropyl, and phenyl.

8. The compound of claim 1, wherein the compound is selected from the compound of Formula (II-A-1), Formula (II-A-2), Formula (II-A-3), Formula (II-A-4), Formula (II-A-5), Formula (II-A-6), Formula (II-A-7), Formula (II-A-8), Formula (II-A-9), and Formula (II-A-10):

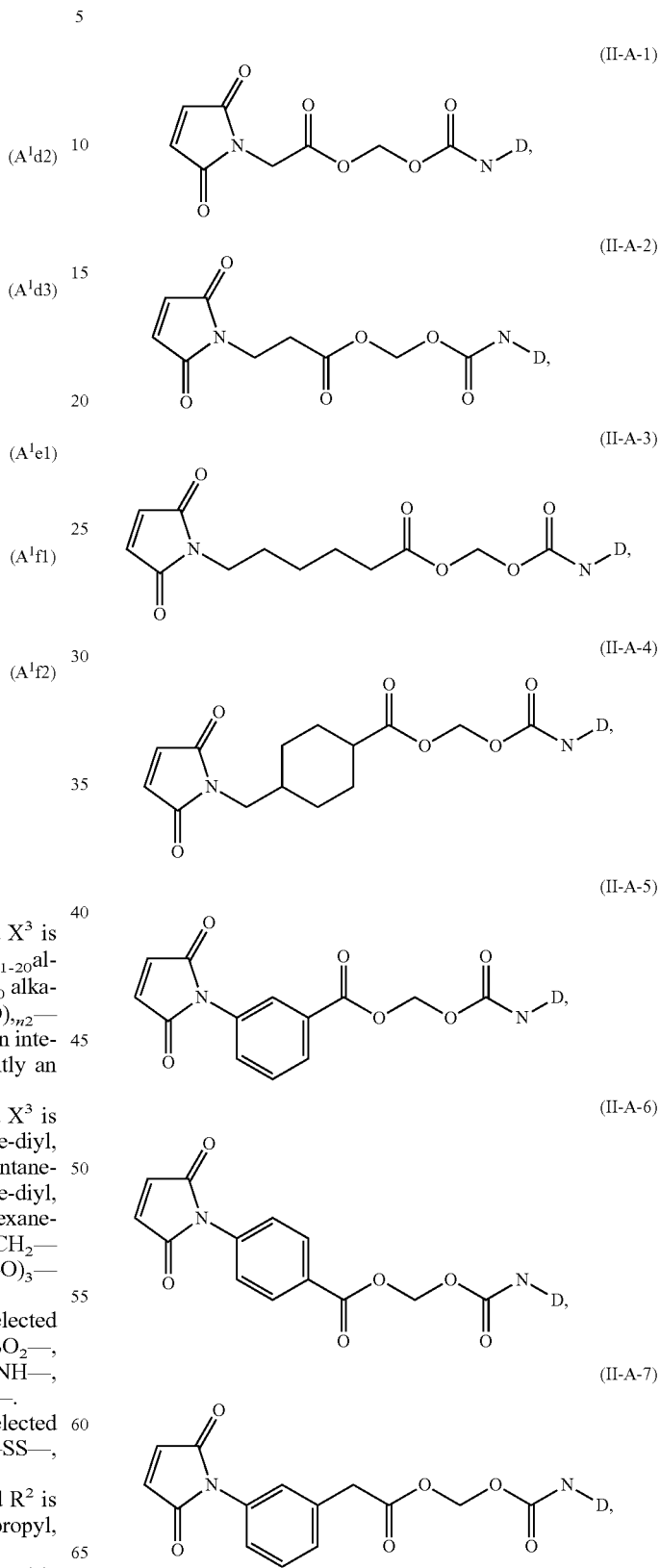

131
-continued
(II-A-8)
(II-A-9)
(II-A-10)
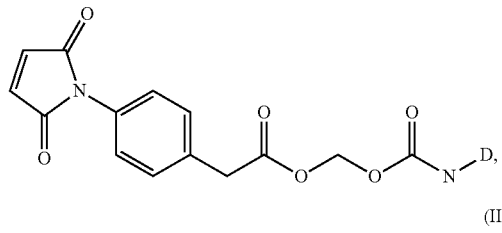
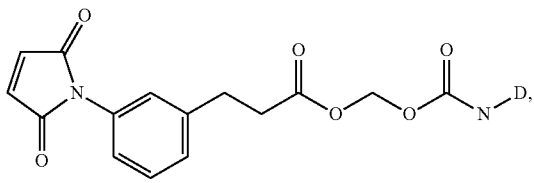
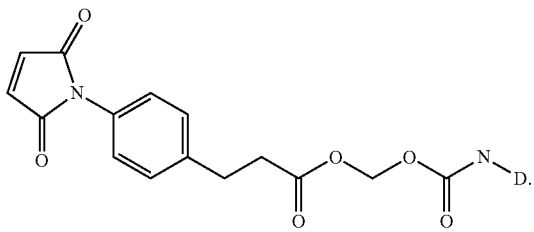
and
9. The compound of claim 1, wherein the compound is selected from the compound of Formula (II-B-1), Formula (II-B-2), Formula (II-B-3 ), Formula (II-B-4), Formula (II-B-5), Formula (II-B-6), Formula (II-B-7), Formula (II-B-8), Formula (II-B-9), Formula (II-B-10). Formula (II-B-1 1), Formula (II-13-1 and Formula (II-B-13):
132
-continued
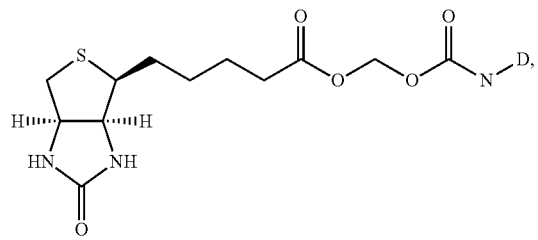
(II-B-1)
(II-B-2)
(II-B-3)
(II-B-4)
(II-B-5)
(II-B-6)
(II-B-7)
(II-B-8)
(II-B-9)
(II-B-10)
(II-B-11)
(II-B-12)
and (II-B-13)

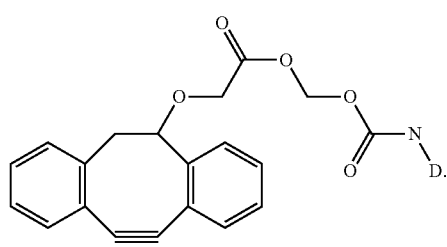

10. The compound of claim 1, wherein the compound is selected from Formula (II-a), Formula (II-b), Formula (II-c), Formula (II-d), Formula (II-e), Formula (II-f), Formula (II-g), Formula (II-h), Formula (II-i), Formula (II-j), Formula (II-k), Formula (II-l). Formula (II-m), Formula (II-n), Formula (II-o), Formula (II-p), Formula (II-q), Formula (II-r ), Formula (II-s), Formula (II-t), Formula (II-u), Formula (II-v), Formula (II-w), Formula (II-x), Formula (II-y), Formula (II-z), Formula (II-aa), Formula (II-ab), and Formula (II-ac), or a salt of any of the foregoing:

(II-a)

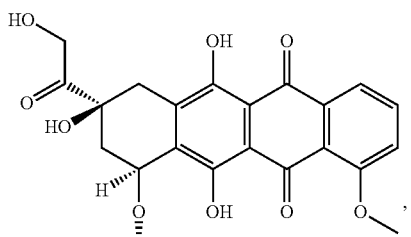

(II-b)

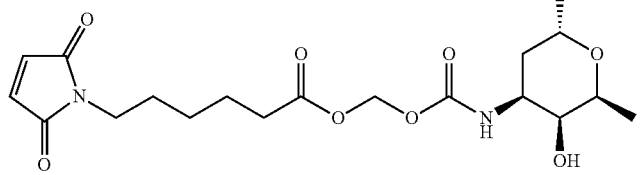

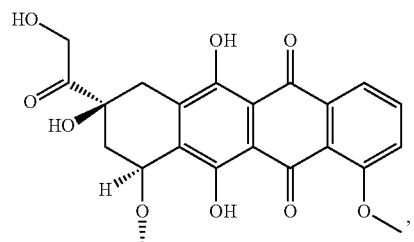

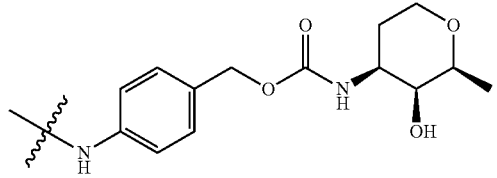

(II-c)

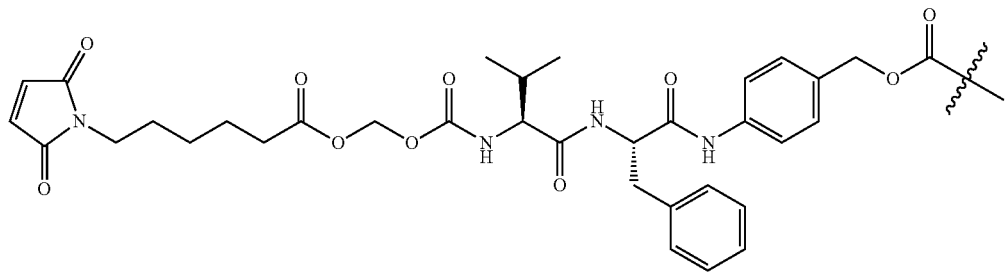

-continued
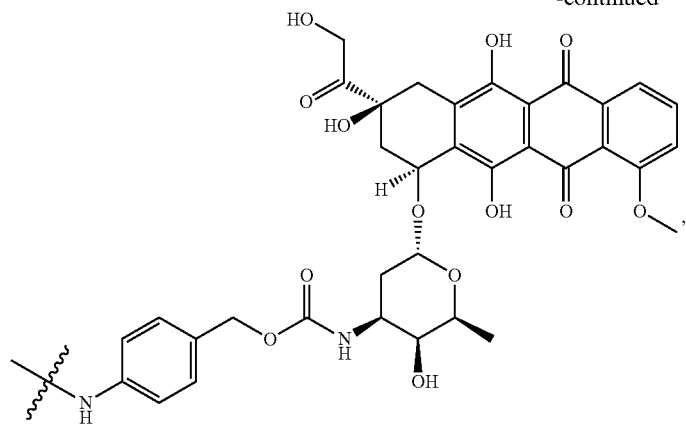
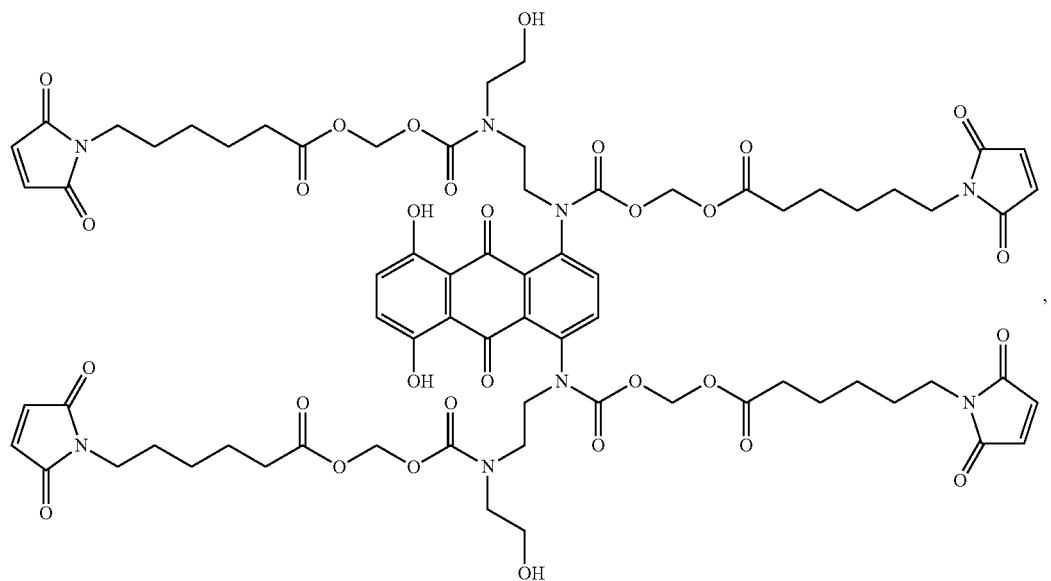
(II-d)
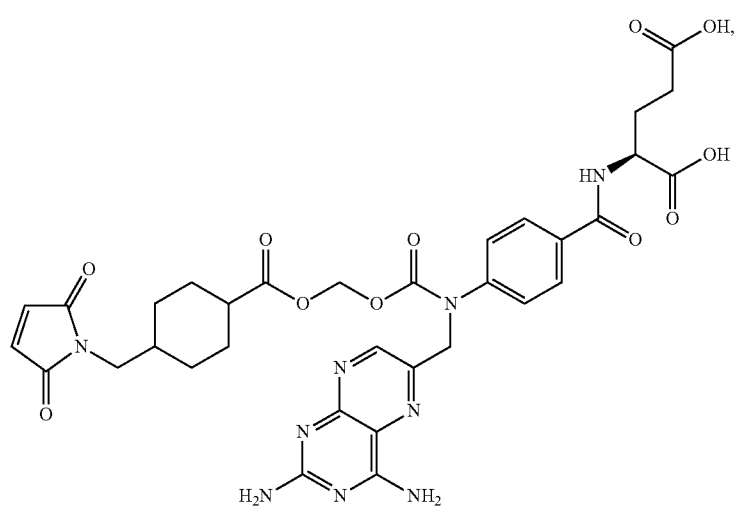
(II-e)

-continued
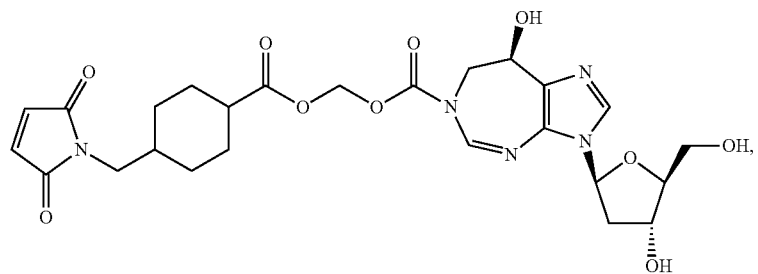
(II-f)
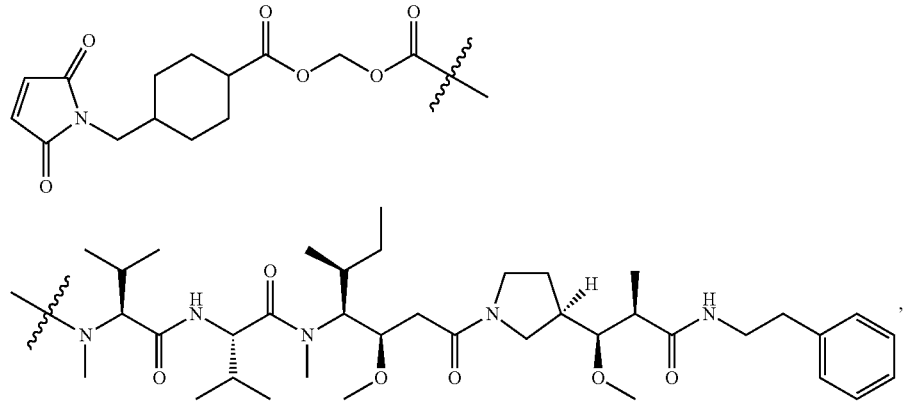
(II-g)
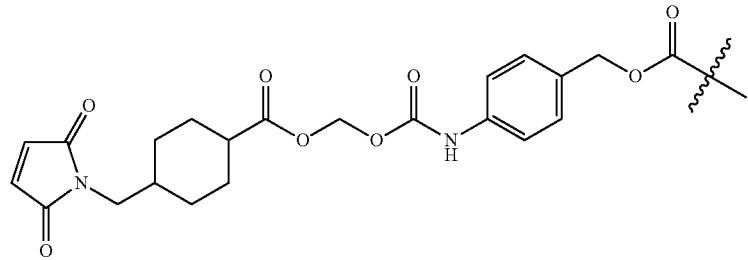
(II-h)
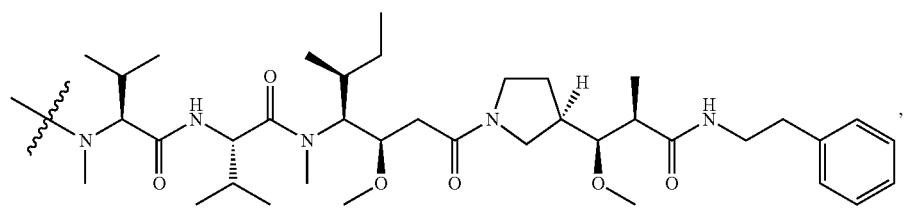
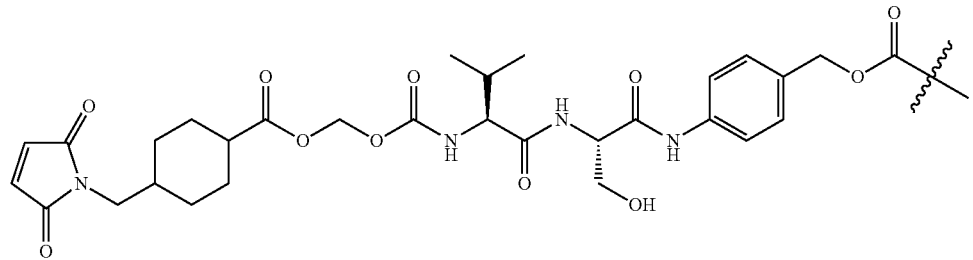
(II-i)
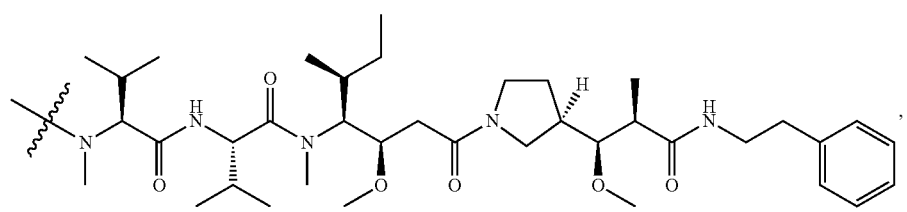

(II-j)
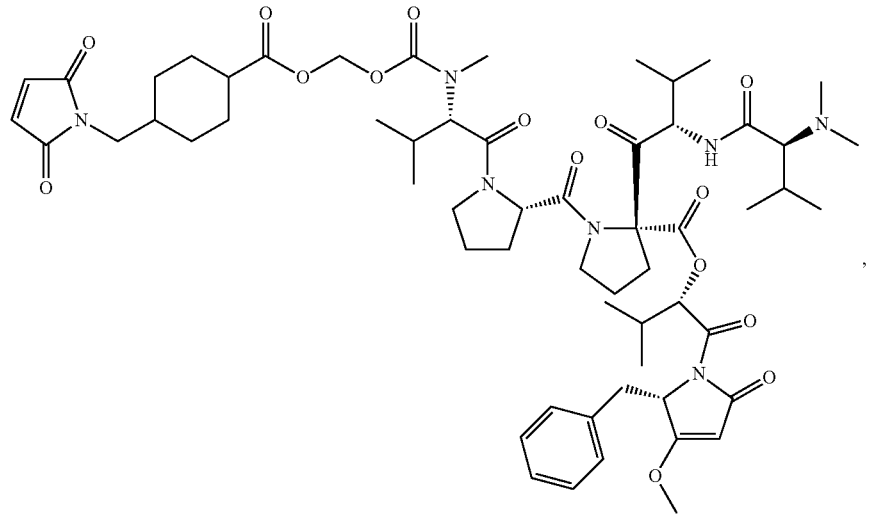
(II-k)
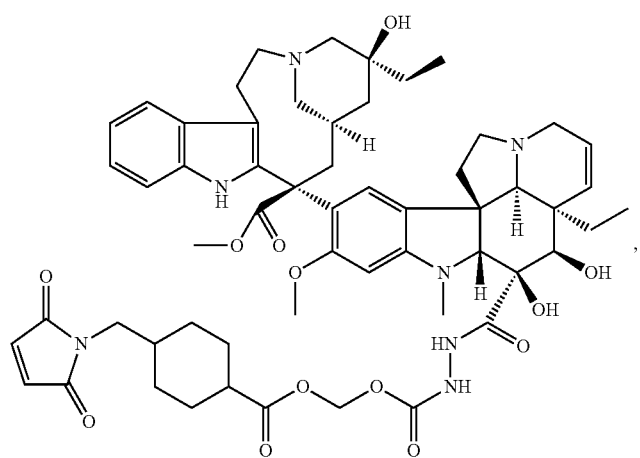
(II-l)
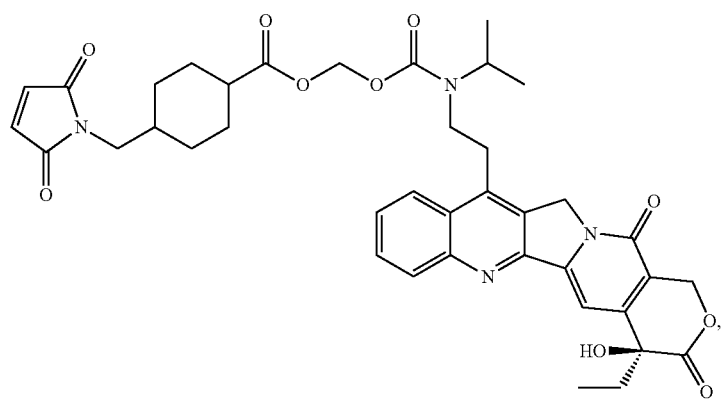

(II-m)
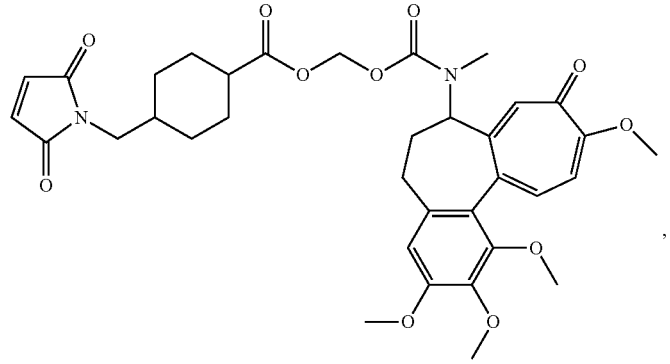
(II-n)
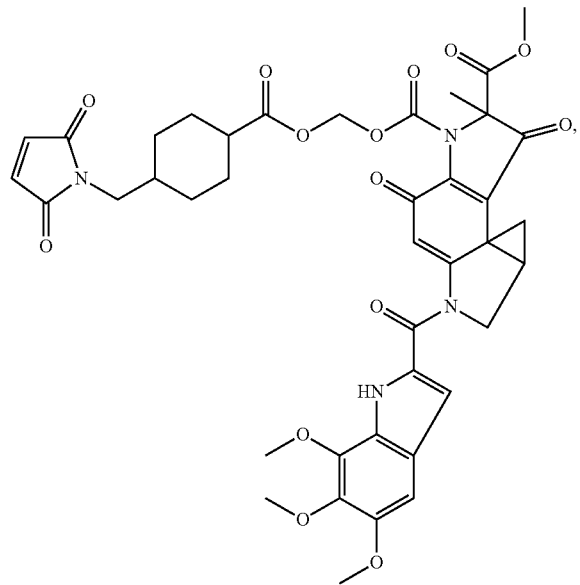
(II-o)
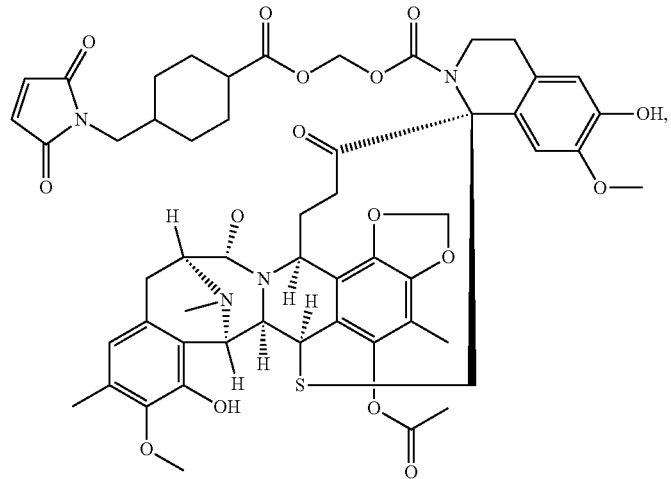

(II-p)
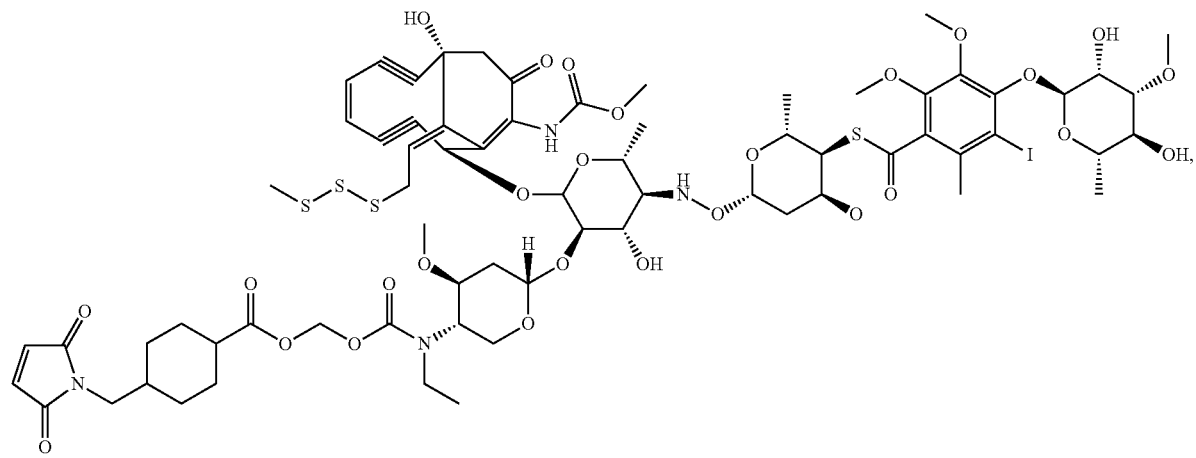
(II-q)
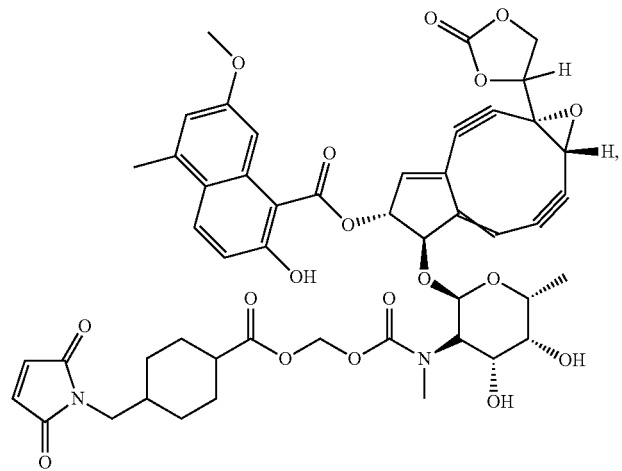
(II-r)
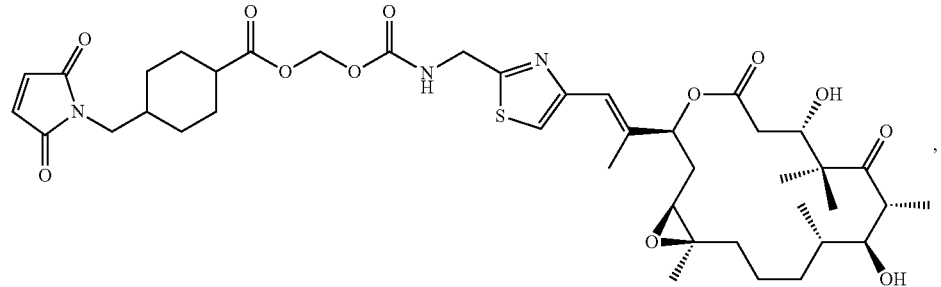

(II-s)
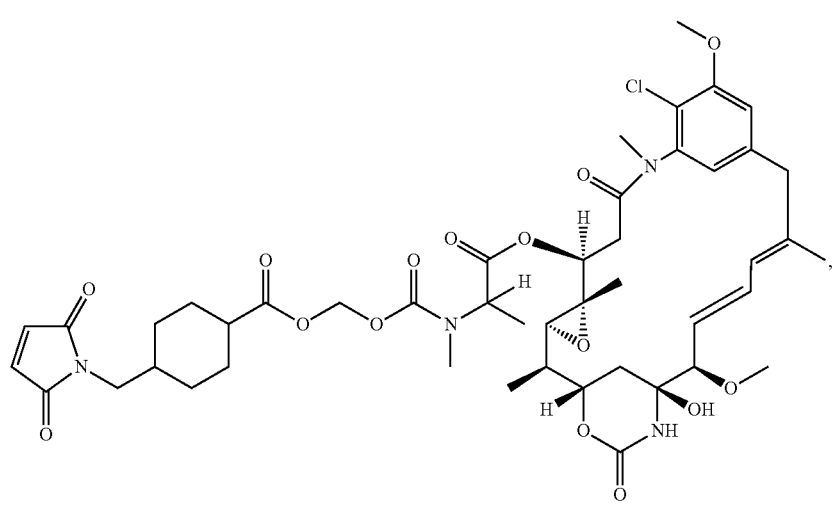
(II-t)
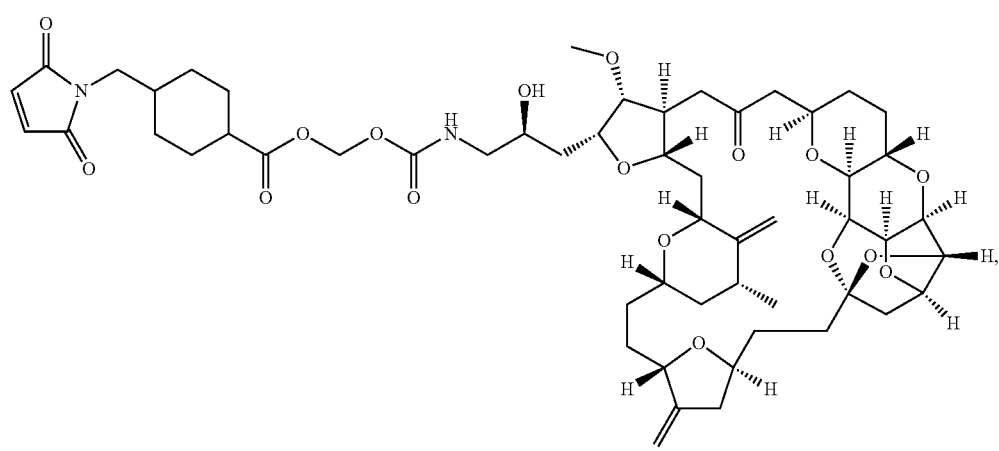
(II-u)
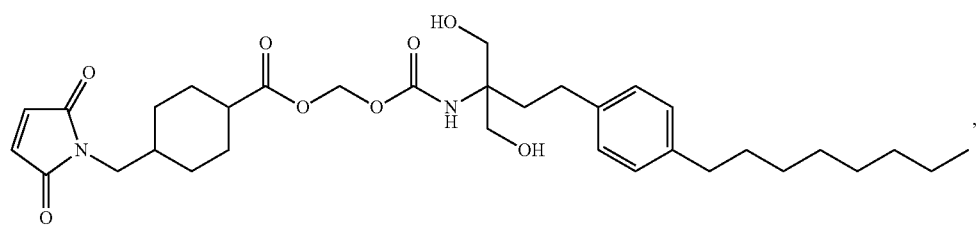
(II-v)
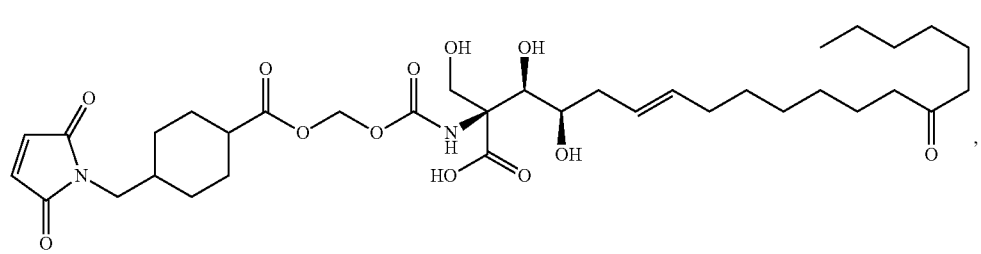

(II-w)
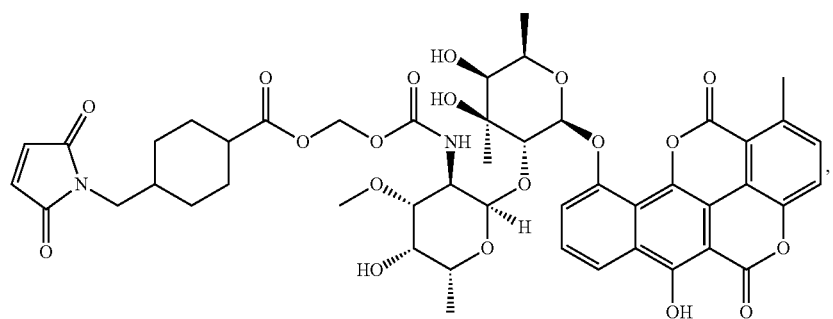
(II-x)
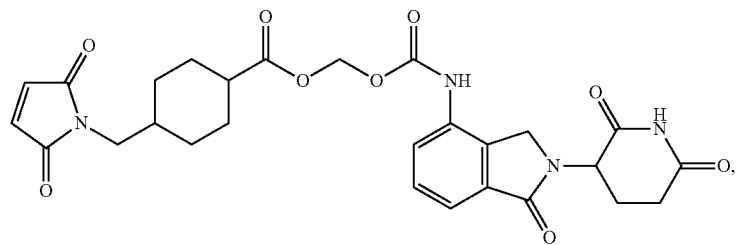
(II-y)
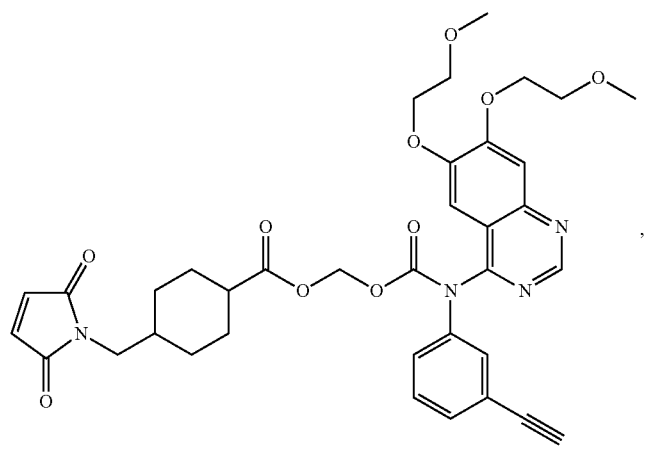
(II-z)
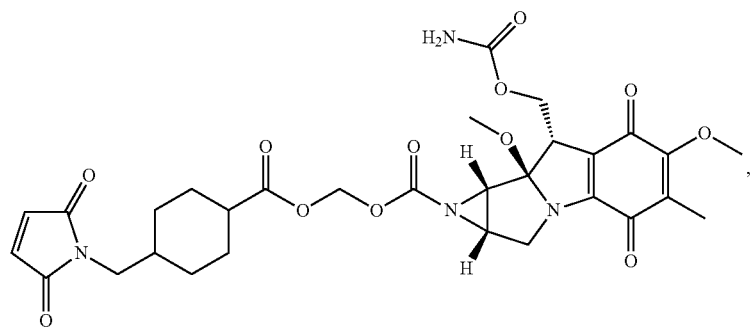

-continued
(II-aa)
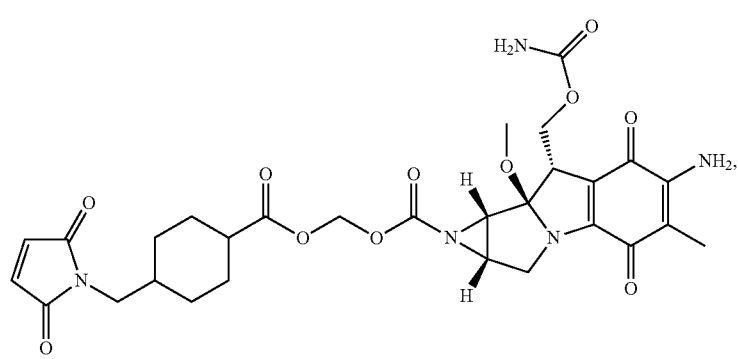
(II-ab)
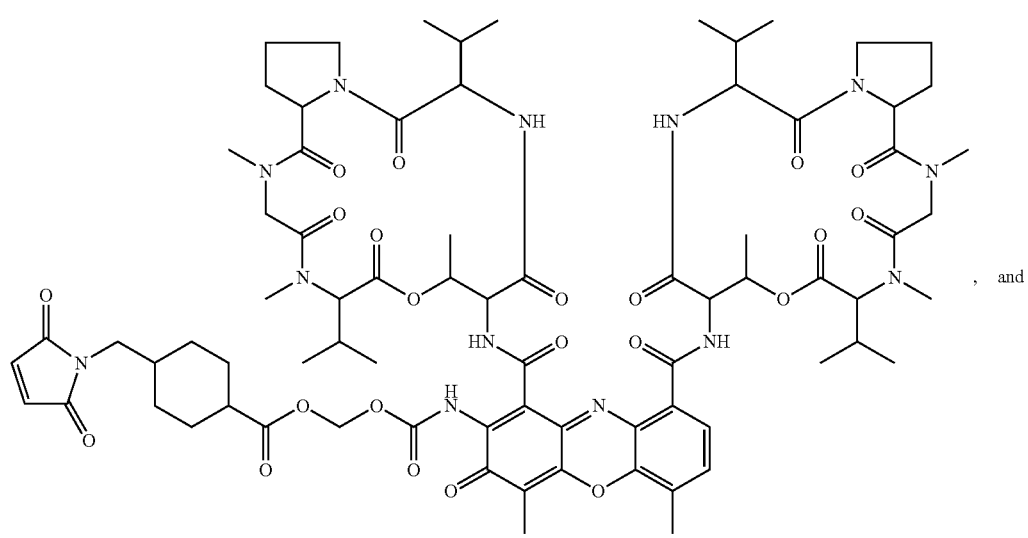
, and
(II-ac)
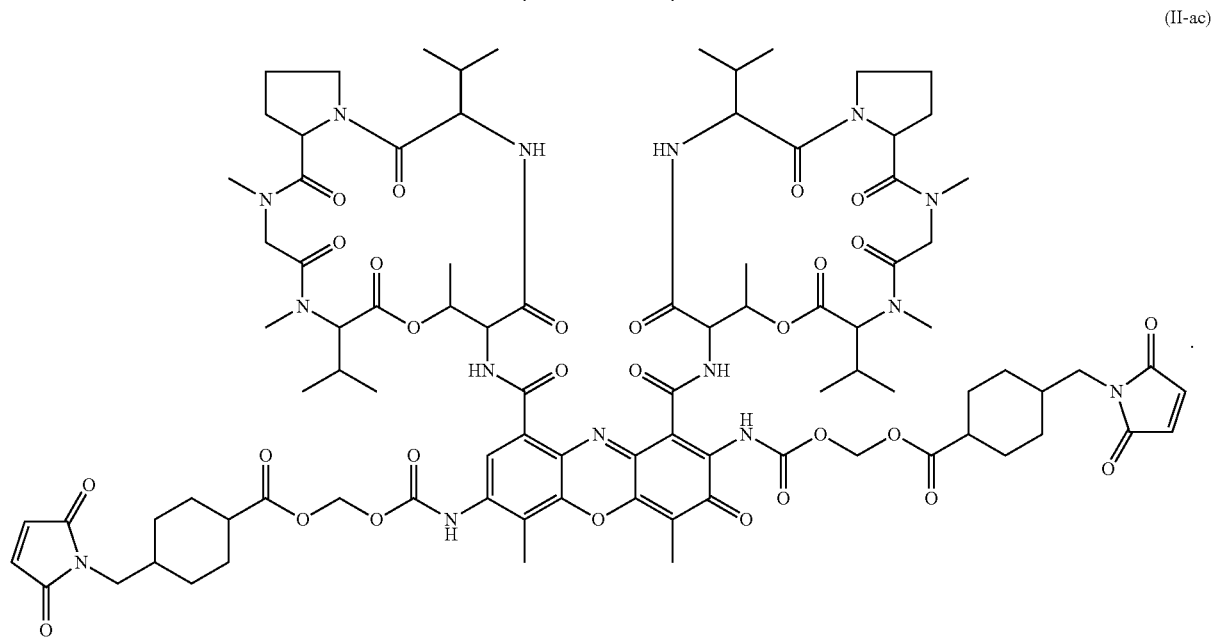
* * * * *